(12) United States Patent
Grandfield et al.

(10) Patent No.: US 9,072,537 B2
(45) Date of Patent: Jul. 7, 2015

(54) VASCULAR AND BODILY DUCT TREATMENT DEVICES AND METHODS

(75) Inventors: Ryan M. Grandfield, Livermore, CA (US); Scott D. Wilson, Redwood City, CA (US); Elliot H. Sanders, Hilo, HI (US)

(73) Assignee: Concentric Medical, Inc., Mountain View, CA (US)

( * ) Notice: Subject to any disclaimer, the term of this patent is extended or adjusted under 35 U.S.C. 154(b) by 630 days.

(21) Appl. No.: 13/365,884

(22) Filed: Feb. 3, 2012

(65) Prior Publication Data

US 2012/0209311 A1 Aug. 16, 2012

Related U.S. Application Data

(63) Continuation-in-part of application No. 13/303,890, filed on Nov. 23, 2011, now Pat. No. 8,529,596, which is a continuation-in-part of application No. 13/021,364, filed on Feb. 4, 2011, now Pat. No.

(Continued)

(51) Int. Cl.
*A61F 2/01* (2006.01)
*A61B 17/221* (2006.01)
(Continued)

(52) U.S. Cl.
CPC ........... *A61B 17/221* (2013.01); *A61B 17/3207* (2013.01); *A61B 17/320725* (2013.01);
(Continued)

(58) Field of Classification Search
CPC ......... A61F 2/01; A61F 2/013; A61B 17/221; A61B 2017/2215
USPC ................. 606/127, 159, 200; 623/1.15, 1.16
See application file for complete search history.

(56) References Cited

U.S. PATENT DOCUMENTS

| | | |
|---|---|---|
| 4,347,846 A | 9/1982 | Dormia |
| 4,706,671 A | 11/1987 | Weinrib |

(Continued)

FOREIGN PATENT DOCUMENTS

| | | |
|---|---|---|
| AU | 2003254553 A1 | 2/2004 |
| CA | 2492978 A1 | 1/2004 |

(Continued)

OTHER PUBLICATIONS

PCT International Preliminary Report on Patentability for PCT International Application No. PCT/US2012/023858 issued Oct. 8, 2013, IB of WIPO, Geneva Switzerland, containing the written opinion of the US Patent Office for PCT/US2012/023858 issued Jun. 4, 2012.

(Continued)

*Primary Examiner* — Kathleen Holwerda
(74) *Attorney, Agent, or Firm* — Tim L. Kitchen; Peter B. Scull; Hamilton, DeSanctis & Cha, LLP

(57) ABSTRACT

Devices including, but not limited to, a self-expandable member having a proximal end portion and a main body portion. The self-expandable member is movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient. The expandable member includes a plurality of cell structures with the cell structures in the main body portion extending circumferentially around a longitudinal axis of the expandable member and the cell structures in the proximal end portion extending less than circumferentially around the longitudinal axis of the expandable member.

23 Claims, 91 Drawing Sheets

Related U.S. Application Data 8,357,179, which is a continuation-in-part of application No. 12/832,857, filed on Jul. 8, 2010, now Pat. No. 8,357,178, which is a continuation-in-part of application No. 12/643,942, filed on Dec. 21, 2009, now abandoned, which is a continuation-in-part of application No. 12/573,676, filed on Oct. 5, 2009, now Pat. No. 8,795,345, which is a continuation-in-part of application No. 12/499,713, filed on Jul. 8, 2009, now Pat. No. 8,795,317.

(51) Int. Cl.
| | |
|---|---|
| A61B 17/3207 | (2006.01) |
| A61B 17/00 | (2006.01) |
| A61B 17/22 | (2006.01) |
| A61F 2/915 | (2013.01) |
| A61F 2/82 | (2013.01) |

(52) U.S. Cl.
CPC . *A61B17/32075* (2013.01); *A61B 2017/00778* (2013.01); *A61B 2017/22045* (2013.01); *A61B 2017/2215* (2013.01); *A61F 2/01* (2013.01); *A61F 2/915* (2013.01); *A61F 2002/018* (2013.01); *A61F 2002/825* (2013.01); *A61F 2002/016* (2013.01); *A61F 2230/0006* (2013.01); *A61F 2230/0069* (2013.01); *A61F 2230/0097* (2013.01)

(56) References Cited

U.S. PATENT DOCUMENTS

| | | | |
|---|---|---|---|
| 4,776,337 A | 10/1988 | Palmaz | |
| 4,886,062 A | 12/1989 | Wiktor | |
| 5,011,488 A | 4/1991 | Ginsburg | |
| 5,192,286 A | 3/1993 | Phan et al. | |
| 5,354,308 A | 10/1994 | Simon et al. | |
| 5,370,653 A | 12/1994 | Cragg | |
| 5,370,683 A | 12/1994 | Fontaine | |
| 5,456,667 A | 10/1995 | Ham et al. | |
| 5,496,365 A | 3/1996 | Sgro | |
| 5,643,312 A | 7/1997 | Fischell et al. | |
| 5,667,486 A | 9/1997 | Mikulich et al. | |
| 5,681,335 A | 10/1997 | Serra et al. | |
| 5,795,331 A | 8/1998 | Cragg et al. | |
| 5,800,519 A | 9/1998 | Sandock | |
| 5,800,520 A * | 9/1998 | Fogarty et al. | 623/1.37 |
| 5,800,525 A | 9/1998 | Bachinski et al. | |
| 5,810,872 A | 9/1998 | Kanesaka et al. | |
| 5,827,321 A * | 10/1998 | Roubin et al. | 623/1.16 |
| 5,836,966 A | 11/1998 | St. Germain | |
| 5,843,117 A | 12/1998 | Alt et al. | |
| 5,855,600 A | 1/1999 | Alt | |
| 5,876,449 A | 3/1999 | Starck et al. | |
| 5,879,370 A | 3/1999 | Fischell et al. | |
| 5,895,398 A | 4/1999 | Wensel et al. | |
| 5,895,406 A | 4/1999 | Gray et al. | |
| 5,911,754 A | 6/1999 | Kanesaka et al. | |
| 5,913,895 A | 6/1999 | Burpee et al. | |
| 5,968,088 A | 10/1999 | Hansen et al. | |
| 5,972,018 A | 10/1999 | Israel et al. | |
| 5,984,929 A * | 11/1999 | Bashiri et al. | 606/108 |
| 6,027,526 A | 2/2000 | Limon et al. | |
| 6,030,397 A | 2/2000 | Monetti et al. | |
| 6,042,597 A | 3/2000 | Kveen et al. | |
| 6,059,822 A | 5/2000 | Kanesaka et al. | |
| 6,066,149 A | 5/2000 | Samson et al. | |
| 6,066,158 A | 5/2000 | Engelson et al. | |
| 6,106,548 A | 8/2000 | Roubin et al. | |
| 6,146,403 A | 11/2000 | St. Germain | |
| 6,200,335 B1 | 3/2001 | Igaki | |
| 6,206,911 B1 | 3/2001 | Milo | |
| 6,217,608 B1 | 4/2001 | Penn et al. | |
| 6,273,910 B1 | 8/2001 | Limon | |
| 6,309,414 B1 | 10/2001 | Rolando et al. | |
| 6,350,271 B1 | 2/2002 | Kurz et al. | |
| 6,398,805 B1 | 6/2002 | Alt | |
| 6,402,431 B1 | 6/2002 | Nish | |
| 6,402,771 B1 | 6/2002 | Palmer et al. | |
| 6,409,754 B1 | 6/2002 | Smith et al. | |
| 6,423,091 B1 | 7/2002 | Hojeibane | |
| 6,468,301 B1 | 10/2002 | Amplatz et al. | |
| 6,468,302 B2 * | 10/2002 | Cox et al. | 623/1.15 |
| 6,475,236 B1 | 11/2002 | Roubin et al. | |
| 6,478,816 B1 | 11/2002 | Kveen et al. | |
| 6,482,217 B1 | 11/2002 | Pintor et al. | |
| 6,488,703 B1 | 12/2002 | Kveen et al. | |
| 6,491,719 B1 | 12/2002 | Fogarty et al. | |
| 6,514,273 B1 | 2/2003 | Voss et al. | |
| 6,551,342 B1 | 4/2003 | Shen et al. | |
| 6,575,995 B1 | 6/2003 | Huter et al. | |
| 6,582,447 B1 * | 6/2003 | Patel et al. | 606/200 |
| 6,626,936 B2 * | 9/2003 | Stinson | 623/1.15 |
| 6,641,590 B1 | 11/2003 | Palmer et al. | |
| 6,660,021 B1 | 12/2003 | Palmer et al. | |
| 6,679,893 B1 | 1/2004 | Tran | |
| 6,692,504 B2 | 2/2004 | Kurz et al. | |
| 6,706,054 B2 | 3/2004 | Wessman et al. | |
| 6,716,240 B2 | 4/2004 | Fischell et al. | |
| 6,818,013 B2 | 11/2004 | Mitelberg et al. | |
| 6,818,613 B2 | 11/2004 | Sharma et al. | |
| 6,881,222 B2 | 4/2005 | White et al. | |
| 6,949,120 B2 | 9/2005 | Kveen et al. | |
| 6,960,228 B2 | 11/2005 | Mitelberg et al. | |
| 7,008,434 B2 | 3/2006 | Kurz et al. | |
| 7,037,321 B2 | 5/2006 | Sachdeva | |
| 7,037,331 B2 | 5/2006 | Mitelberg et al. | |
| 7,081,130 B2 | 7/2006 | Jang | |
| 7,108,714 B1 | 9/2006 | Becker | |
| 7,195,648 B2 | 3/2007 | Jones et al. | |
| 7,291,166 B2 | 11/2007 | Cheng et al. | |
| 7,300,458 B2 | 11/2007 | Henkes et al. | |
| 7,311,726 B2 | 12/2007 | Mitelberg et al. | |
| 7,316,692 B2 | 1/2008 | Huffmaster | |
| 7,485,130 B2 | 2/2009 | St. Germain | |
| 7,651,513 B2 | 1/2010 | Teoh et al. | |
| 7,655,033 B2 | 2/2010 | Feller, III et al. | |
| 7,678,119 B2 | 3/2010 | Little et al. | |
| 7,811,300 B2 | 10/2010 | Feller, III et al. | |
| 7,875,044 B2 | 1/2011 | Feller, III et al. | |
| 7,887,560 B2 | 2/2011 | Kusleika | |
| 8,062,347 B2 * | 11/2011 | Tenne | 623/1.15 |
| 8,357,178 B2 | 1/2013 | Grandfield et al. | |
| 8,357,179 B2 | 1/2013 | Grandfield et al. | |
| 8,529,596 B2 | 9/2013 | Grandfield et al. | |
| 8,795,317 B2 | 8/2014 | Grandfield et al. | |
| 8,795,345 B2 | 8/2014 | Grandfield et al. | |
| 2001/0047200 A1 | 11/2001 | White et al. | |
| 2003/0004567 A1 | 1/2003 | Boyle et al. | |
| 2003/0100917 A1 | 5/2003 | Boyle et al. | |
| 2003/0116751 A1 | 6/2003 | Elman | |
| 2003/0176914 A1 * | 9/2003 | Rabkin et al. | 623/1.15 |
| 2003/0199921 A1 | 10/2003 | Palmer et al. | |
| 2004/0068314 A1 | 4/2004 | Jones et al. | |
| 2004/0199175 A1 | 10/2004 | Jaeger et al. | |
| 2004/0236368 A1 | 11/2004 | McGuckin, Jr. et al. | |
| 2005/0209678 A1 | 9/2005 | Henkes et al. | |
| 2005/0267491 A1 | 12/2005 | Kellett et al. | |
| 2006/0116751 A1 | 6/2006 | Bayle et al. | |
| 2006/0265048 A1 | 11/2006 | Cheng et al. | |
| 2006/0287701 A1 | 12/2006 | Pal | |
| 2007/0038178 A1 | 2/2007 | Kusleika | |
| 2007/0190866 A1 | 8/2007 | Zart et al. | |
| 2007/0191866 A1 | 8/2007 | Palmer et al. | |
| 2007/0198051 A1 | 8/2007 | Clubb et al. | |
| 2007/0225739 A1 | 9/2007 | Pintor et al. | |
| 2007/0280367 A1 | 12/2007 | Nakao et al. | |
| 2007/0288054 A1 | 12/2007 | Tanaka et al. | |
| 2008/0125855 A1 | 5/2008 | Henkes et al. | |
| 2008/0208244 A1 | 8/2008 | Boylan et al. | |
| 2008/0262487 A1 | 10/2008 | Wensel et al. | |
| 2009/0105722 A1 | 4/2009 | Fulkerson et al. | |
| 2009/0105737 A1 | 4/2009 | Fulkerson et al. | |

(56) References Cited

U.S. PATENT DOCUMENTS

| | | |
|---|---|---|
| 2010/0100106 A1 | 4/2010 | Ferrera |
| 2010/0114135 A1 | 5/2010 | Wilson et al. |
| 2010/0161034 A1 | 6/2010 | Leanna et al. |
| 2010/0174309 A1 | 7/2010 | Fulkerson et al. |
| 2010/0318097 A1 | 12/2010 | Ferrera et al. |
| 2010/0331853 A1 | 12/2010 | Garcia et al. |
| 2011/0009875 A1 | 1/2011 | Grandfield et al. |
| 2011/0009940 A1 | 1/2011 | Grandfield et al. |
| 2011/0009941 A1 | 1/2011 | Grandfield et al. |
| 2011/0009950 A1 | 1/2011 | Grandfield et al. |
| 2011/0130784 A1 | 6/2011 | Kusleika |
| 2011/0184456 A1 | 7/2011 | Grandfield et al. |
| 2011/0196414 A1 | 8/2011 | Porter et al. |
| 2012/0123466 A1 | 5/2012 | Porter et al. |
| 2012/0215250 A1 | 8/2012 | Grandfield et al. |
| 2014/0046338 A1 | 2/2014 | Grandfield et al. |

FOREIGN PATENT DOCUMENTS

| | | |
|---|---|---|
| DE | 4032759 A1 | 4/1992 |
| DE | 19834956 A1 | 5/1999 |
| DE | 10233085 A1 | 1/2004 |
| DE | 10301850 A1 | 7/2004 |
| EP | 0897698 A2 | 2/1999 |
| EP | 0914807 A2 | 5/1999 |
| EP | 0916362 A1 | 5/1999 |
| EP | 1266640 A2 | 12/2002 |
| EP | 1266640 A3 | 12/2002 |
| EP | 1266640 B1 | 12/2002 |
| EP | 1362564 A1 | 11/2003 |
| EP | 1534178 B1 | 10/2007 |
| EP | 1351626 B1 | 2/2008 |
| EP | 1542617 | 1/2011 |
| EP | 1542617 A1 | 1/2011 |
| GB | 2463592 A | 3/2010 |
| JP | 62049841 A | 3/1987 |
| JP | 7124251 A | 5/1995 |
| JP | 2001511030 | 8/2001 |
| JP | 2003512887 | 4/2003 |
| JP | 2004536666 | 12/2004 |
| JP | 2005532887 | 11/2005 |
| JP | 2006521865 | 9/2006 |
| JP | 2008512207 | 4/2008 |
| JP | 2008519668 | 6/2008 |
| JP | 2008522757 | 7/2008 |
| JP | 2010264261 A | 11/2010 |
| WO | WO9704711 A1 | 2/1997 |
| WO | WO9725000 A1 | 7/1997 |
| WO | WO9832412 A2 | 7/1998 |
| WO | WO0132099 A2 | 5/2001 |
| WO | WO0145592 A1 | 6/2001 |
| WO | WO03011188 A1 | 2/2003 |
| WO | WO2004006804 A1 | 1/2004 |
| WO | WO2004008991 A1 | 1/2004 |
| WO | WO2004093696 A1 | 11/2004 |
| WO | WO2006029321 A1 | 3/2006 |
| WO | WO2006053270 A2 | 5/2006 |
| WO | WO2006063222 A1 | 6/2006 |
| WO | WO2008063156 A2 | 5/2008 |
| WO | WO2010010545 A1 | 1/2010 |

OTHER PUBLICATIONS

Extended and Supplementary European Search Report for PCT/US2012/023858 issued by the European Patent Office, Rijswijk, Netherlands dated Jan. 20, 2014.

International Search Report and Written Opinion for PCT International Application No. PCT/US2012/023858 issued by the ISA dated Jun. 4, 2012.

PCT International Preliminary Report on Patentability for PCT/US2010/041434, issued Jan. 10, 2012, IB of WIPO, Geneva Switzerland, containing the written opinion of the US Patent Office for PCT/US2010/041434, issued Sep. 8, 2010, Alexandria, VA, USA.

EV3, Fully Deployable. Completely Retrievable. Solitaire AB Neurovascular Remodeling Device, Solitaire AB Brochure, www.ev3.net, accessed on Jul. 16, 2009.

International Search Report and Written Opinion for PCT International Application No. PCT/US2010/041434 issued by the ISA dated Sep. 8, 2010, Virginia, US.

Wilson, Scott et al., Devices and Methods for Temporarily Opening a Blood Vessel, U.S. Patent Application, Oct. 31, 2008.

* cited by examiner

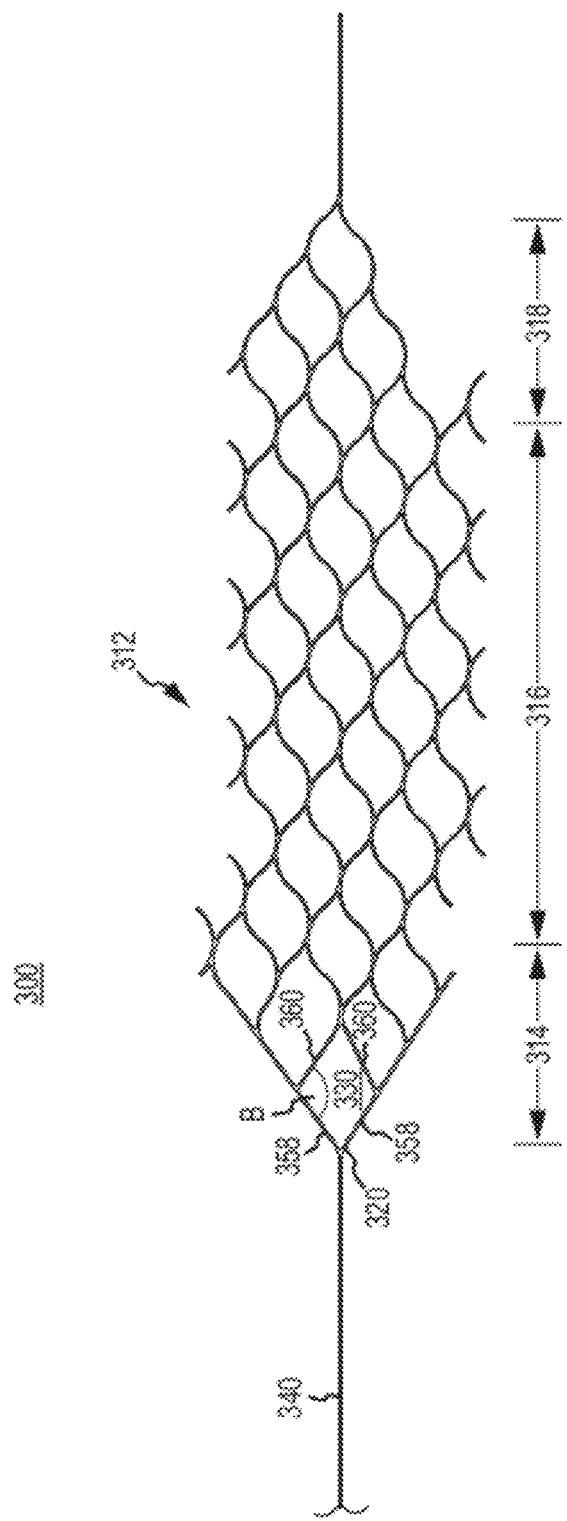

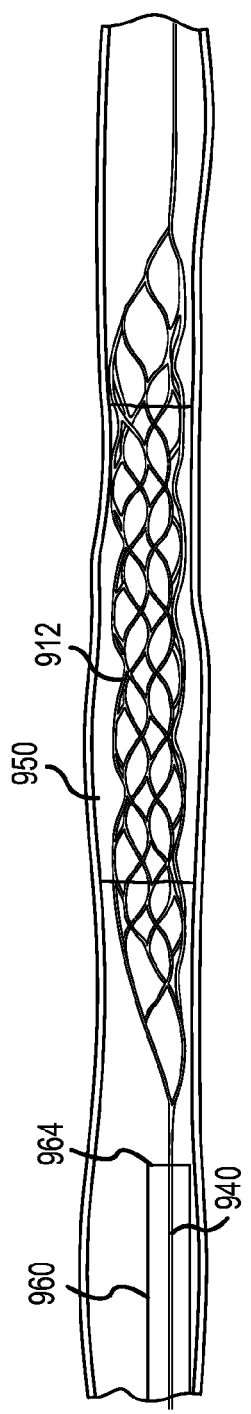

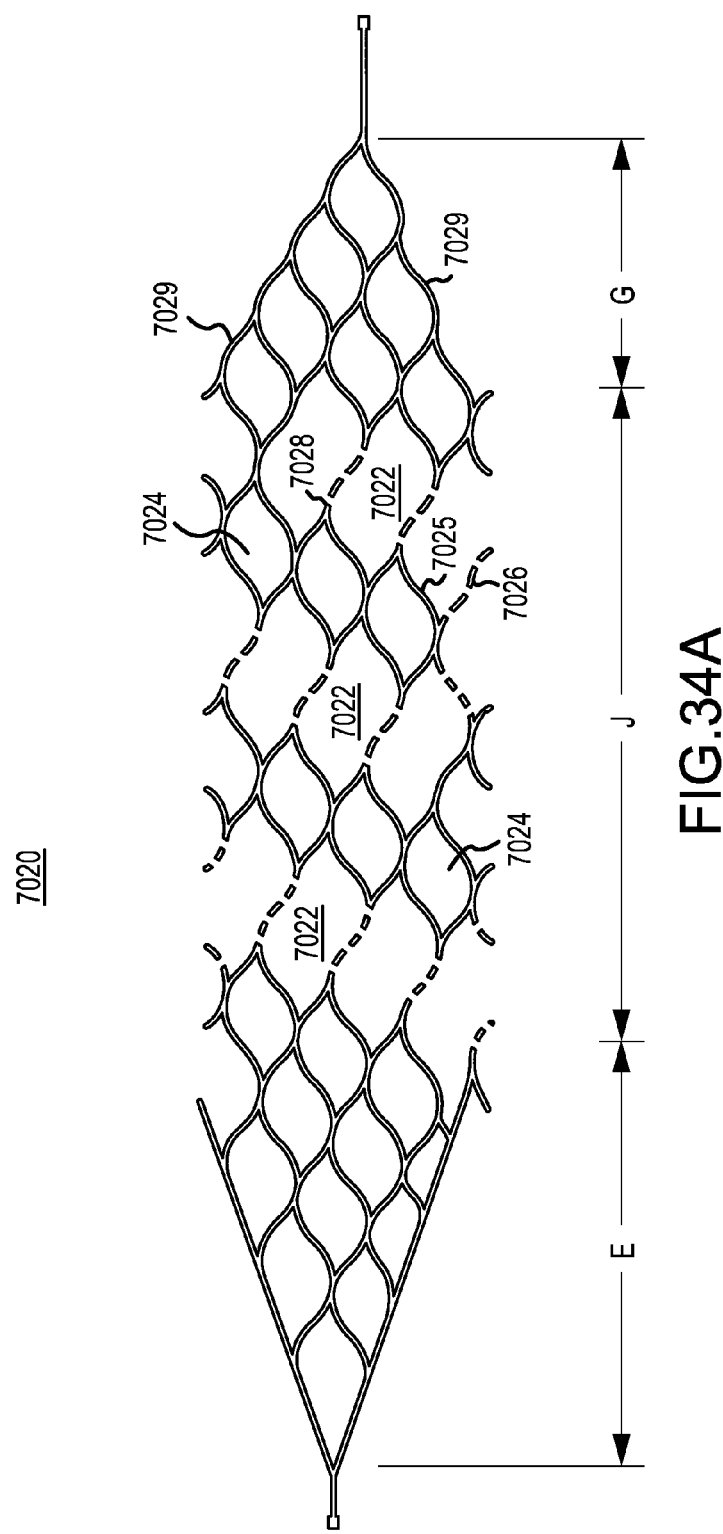

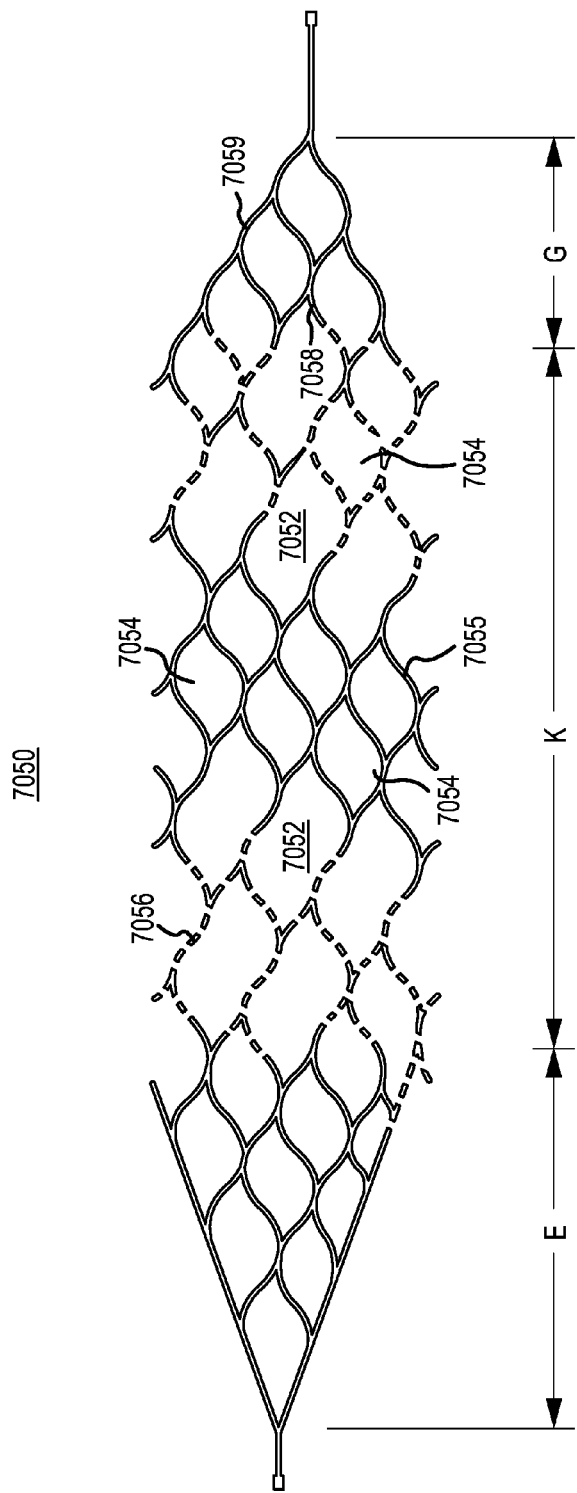

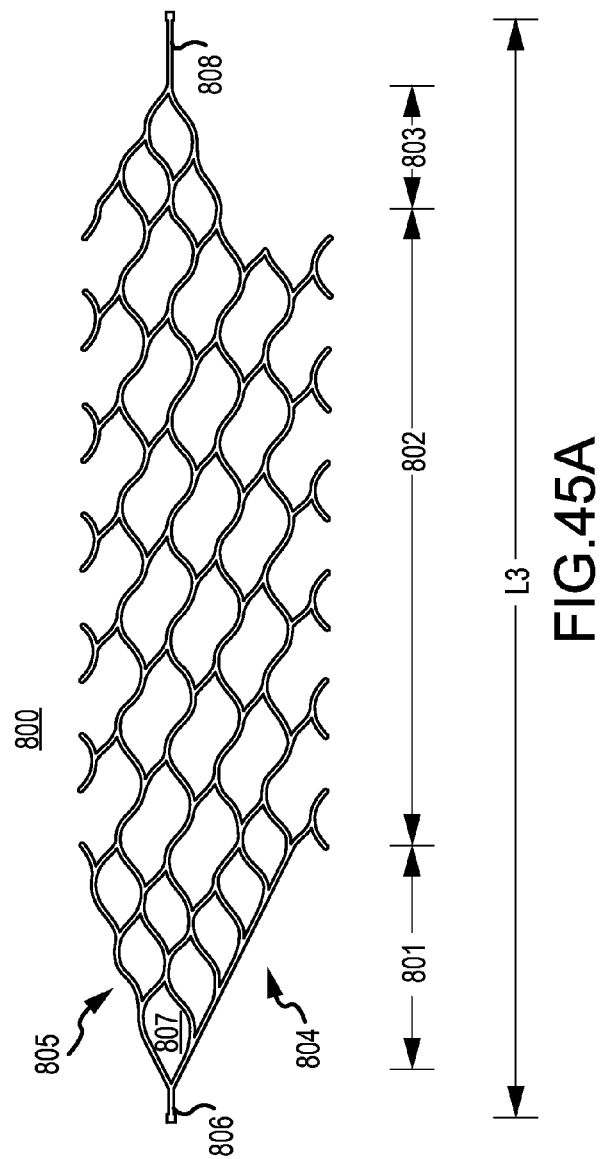

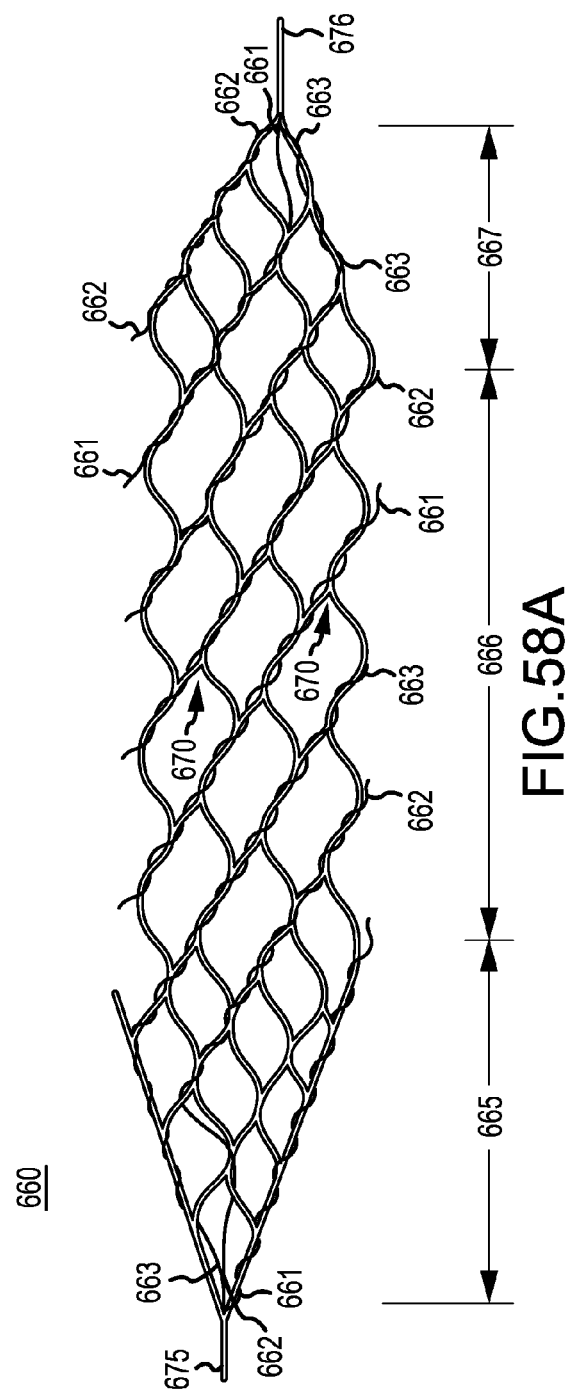

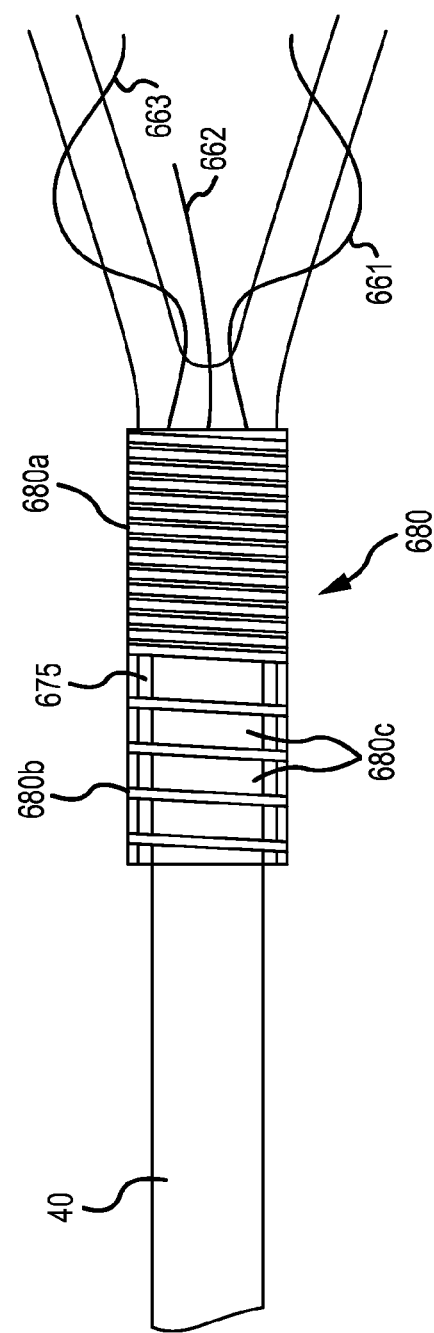

VASCULAR AND BODILY DUCT TREATMENT DEVICES AND METHODS

RELATED APPLICATION

This application claims the benefit to and is a continuation-in-part of U.S. patent application Ser. No. 13/303,890, filed Nov. 23, 2011, which is a continuation-in-part of U.S. patent application Ser. No. 13/021,364, filed Feb. 4, 2011, which is a continuation-in-part of U.S. patent application Ser. No. 12/832,857, filed Jul. 8, 2010, which is a a continuation-in-part of U.S. patent application Ser. No. 12/643,942, filed Dec. 21, 2009, which is a continuation-in-part of U.S. patent application Ser. No. 12/573,676, filed Oct. 5, 2009, which is a continuation-in-part of U.S. patent application Ser. No. 12/499,713, filed Jul. 8, 2009.

TECHNICAL FIELD

This application relates to devices and methods for treating the vasculature and other ducts within the body.

BACKGROUND

Self-expanding prostheses, such as stents, covered stents, vascular grafts, flow diverters, and the like have been developed to treat ducts within the body. Many of the prostheses have been developed to treat blockages within the vasculature and also aneurysms that occur in the brain. What are needed are improved treatment methods and devices for treating the vasculature and other body ducts, such as, for example, aneurysms, stenoses, embolic obstructions, and the like.

SUMMARY OF THE DISCLOSURE

In accordance with one implementation a vascular or bodily duct treatment device is provided that comprises an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of cell structures, the expandable member having a proximal end portion with a proximal end, a cylindrical main body portion and a distal end portion with a distal end, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a distal position at or near the cylindrical main body portion. In one implementation the self-expandable member has a longitudinal slit extending along at least a portion of the length of the self-expandable member between the proximal end and the distal end.

In accordance with another implementation a kit is provided that comprises an elongate flexible wire having a proximal end and a distal end with an elongate self-expandable member coupled to the distal end, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment in the bodily duct or vasculature of a patient, the self-expandable member comprising a plurality of cell structures, the self-expandable member having a proximal end portion with a proximal end, a cylindrical main body portion and a distal end portion with a distal end, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a distal position at or near the cylindrical main body portion, the elongate wire with the expandable member having a first length; and a delivery catheter having a second length and sufficient flexibility to navigate the vasculature or bodily duct of the patient, the delivery catheter having a proximal end, a distal end and an inner lumen, the inner lumen having a diameter sufficient to receive the self-expandable member in its unexpanded position and for advancing the unexpanded member from the proximal end to the distal end of the catheter, the second length being less than the first length to allow distal advancement of the self-expandable member beyond the distal end of the catheter to permit the expandable member to deploy toward its expanded position, the distal end of the catheter and the self-expandable member configured to permit proximal retraction of the self-expandable member into the lumen of the catheter when the self-expandable member is partially or fully deployed outside the distal end of the catheter. In one implementation, the self-expandable member has a longitudinal slit extending along at least a portion of the length of the self-expandable member between the proximal end and the distal end.

In accordance with one implementation, a bodily duct or vascular treatment device is provided having an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion. In one implementation, connected to the proximal-most end of the expandable member is a proximally extending elongate flexible wire having a length and flexibility sufficient for navigating and accessing the vasculature or bodily duct of the patient.

In accordance with another implementation, a vascular treatment device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the vasculature of a patient, the expandable member comprising a plurality of generally longitudinal undulating elements with adjacent undulating elements being interconnected in a manner to form a plurality of cell structures that are arranged to induce twisting of the expandable member as the expandable member transitions from the unexpanded position to the expanded position, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that form first and second substantially linear rail segments that each extend from a position at or near the proximal-most end of the expandable member to a position at or near the cylindrical main body portion. In one implementation, connected to the proximal-most end of the expandable member is a proximally extending elongate flexible wire having a length and flexibility sufficient for navigating and accessing the vasculature or bodily duct of the patient.

In accordance with another implementation, a bodily duct or vascular treatment device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected to form a plurality of diagonally disposed cell structures, the expandable member having a cylindrical portion and a distal end portion, the cell structures in the cylindrical portion extending circumferentially around a longitudinal axis of the expandable member, the cell structures in the distal end portion extending less than circumferentially around the longitudinal axis of the expandable member, the proximal-most cell structures in the main body portion having proximal-most end points. One or more of the proximal-most end points of the expandable member have a proximally extending elongate flexible wire having a length and flexibility sufficient for navigating and accessing the vasculature or bodily duct of the patient.

In accordance with another implementation, a kit is provided that includes an elongate flexible wire having a proximal end and a distal end with an elongate self-expandable member attached to the distal end, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion, the elongate wire and expandable member having a first length, and a delivery catheter having a second length and sufficient flexibility to navigate the vasculature or bodily duct of a patient, the delivery catheter having a proximal end, a distal end and an inner diameter, the inner diameter sufficient to receive the expandable member in its unexpanded position and for advancing the unexpanded member from the proximal end to the distal end of the catheter, the second length being less that the first length to allow distal advancement of the expandable member beyond the distal end of the catheter to permit the expandable member to deploy toward its expanded position, the distal end of the catheter and the expandable member configured to permit proximal retraction of the expandable member into the catheter when the expandable member is partially or fully deployed outside the distal end of the catheter.

In accordance with another implementation, a method for removing an embolic obstruction from a vessel of a patient is provided that includes (a) advancing a delivery catheter having an inner lumen with proximal end and a distal end to the site of an embolic obstruction in the intracranial vasculature of a patient so that the distal end of the inner lumen is positioned distal to the embolic obstruction, the inner lumen having a first length, (b) introducing an embolic obstruction retrieval device comprising an elongate flexible wire having a proximal end and a distal end with an elongate self-expandable member attached to the distal end into the proximal end of the inner lumen of the catheter and advancing the self-expandable member to the distal end of the lumen, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer cell structures in the proximal end portion having proximal linear wall segments that, in a two-dimensional view, form first and second substantially linear rail segments that each extend from a position at or near the proximal end of the expandable member to a position at or near the cylindrical main body portion, the elongate wire and expandable member in combination having a second length longer than the first length, (c) proximally retracting the delivery catheter sufficient to deploy the self-expandable device so that the one or more of the cell structures entrap at least a portion of the embolic obstruction, and (d) proximally retracting the delivery catheter and self-expandable device to outside the patient. In an alternative implementation, the self-expandable member is partially or fully retracted into the inner lumen of the delivery catheter prior to proximally retracting the delivery catheter and self-expandable device to outside the patient.

In accordance with another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the cell structures in the main body portion comprise a first plurality of intersecting struts and extend circumferentially around a longitudinal axis of the expandable member, the cell structures in the proximal end portion comprise a second plurality of intersecting struts and extend less than circumferentially around the longitudinal axis of the expandable member, at least some of the first plurality of intersecting struts having a thickness to width ratio of greater than one.

In accordance with yet another implementation, a device is provided comprising a delivery wire, an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the proximal end having an integrally formed wire segment extending therefrom with a coil positioned about the wire segment, the coil comprising a first closely wound segment and a second loosely wound segment that contains at least one gap, the cell structures in the main body portion extending circumferentially around a longitudinal axis of the expandable member, the cell structures in the proximal end portion extending less than circumferentially around the longitudinal axis of the expandable member, a proximal end of the wire segment attached to a distal end of the delivery wire by a bonding agent within the second loosely wound segment of the coil.

In accordance with yet another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the cell structures in the main body portion extending circumferentially around a longitudinal axis of the expandable member, the cell structures in the proximal end portion extending less than circumferentially around the longitudinal axis of the expandable member, the cell structures having dimensional and material characteristics that result in about a $-1.5N$ to a about a $-3.5N$ overall reduction in radial force along the length of the expandable member per millimeter of expansion during about an initial 0.50 mm diametric range of expansion from the nominal diameter and that results in about a $-0.10N$ to about a $-0.50N$ overall reduction in radial force along the length of the expandable member per millimeter of expansion during subsequent diametric ranges of expansion. In one implementation the elongate self-expandable member has a designated maximum second nominal diameter, the radial force exerted by the elongate self-expandable member being greater than zero when expanded to the maximum second nominal diameter.

In accordance with yet another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the cell structures in the proximal end portion extending less than circumferentially around the longitudinal axis of the expandable member, the cell structures having dimensional and material characteristics that result in about a $-1.5N$ to a about a $-3.5N$ overall reduction in radial force along the length of the expandable member per millimeter of expansion during about an initial 0.50 mm diametric range of expansion from the first nominal diameter and that results in about a $-0.10N$ to about a $-0.50N$ overall reduction in radial force along the length of the expandable member per millimeter of expansion during subsequent diametric ranges of expansion. In one implementation the elongate self-expandable member has a designated maximum second nominal diameter, the radial force exerted by the elongate self-expandable member being greater than zero when expanded to the maximum second nominal diameter.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion and a cylindrical main body portion, the cell structures in the main body portion extending circumferentially around a longitudinal axis of the expandable member, the cell structures in the proximal end portion extending less than circumferentially around the longitudinal axis of the expandable member to form first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension. In one implementation the first and second peripheral rails are devoid of undulations and the percentage change between the first width dimension and second width dimension is between about 20.0% and about 50.0%.

In another implementations a clot retrieval devices is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion and a cylindrical main body portion, the cell structures in the main body portion extending circumferentially around a longitudinal axis of the expandable member, the cell structures in the proximal end portion extending less than circumferentially around the longitudinal axis of the expandable member to form first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the percentage change between the first width dimension and second width dimension is between about 20.0% and about 50.0%, the third set of cell structures comprising struts having a third width dimensions less than the second width dimension, the fourth set of cell structures comprising struts having a fourth width dimensions less than the second width dimension, the percentage difference between the second width dimension and the third width dimension being between about 10.0% and about 25.0%, the percentage difference between the second width dimension and the fourth width dimension being between about 10.0% and about 25.0%.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion and a cylindrical main body portion, the cell structures in the main body portion extending circumferentially around a longitudinal axis of the expandable member, the cell structures in the proximal end portion extending less than circumferentially around the longitudinal axis of the expandable member to form first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the percentage change between the first width dimension and second width dimension is between about 20.0% and about 50.0%, the third set of cell structures comprising struts having a third width dimension less than the second width dimension, the fourth set of cell structures comprising struts having a fourth width dimension substantially the same as the second width dimension, the percentage difference between the second width dimension and the third width dimension being between about 10.0% and about 25.0%.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion and a cylindrical main body portion, the cell structures in the main body portion extending circumferentially around a longitudinal axis of the expandable member, the cell structures in the proximal end portion extending less than circumferentially around the longitudinal axis of the expandable member to form first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth and fifth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the size of the cell structures in the third and fifth set of cell structures being substantially the same, the size of the cell structures in the fourth set of cell structures being greater than the size of the cell structures in the third set of cell structures, the cell structures in the third, fourth and fifth set of cell structures comprising third, fourth and fifth struts, respectively, at least some of the fourth and fifth struts, or segments thereof, having a width dimension that is greater than the width dimension of the third struts.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion and a cylindrical main body portion, the cell structures in the main body portion extending circumferentially around a longitudinal axis of the expandable member, the cell structures in the proximal end portion extending less than circumferentially around the longitudinal axis of the expandable member to form first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth and fifth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the size of the cell structures in the third and fifth set of cell structures being substantially the same, the size of the cell structures in the fourth set of cell structures being greater than the size of the cell structures in the third set of cell structures, the cell structures in the third, fourth and fifth set of cell structures comprising third, fourth and fifth struts, respectively, the width dimension of the third struts being less than the second width dimension, at least some of the fourth and fifth struts, or segments thereof, having a width dimension substantially equal to the second width dimension.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the cell structures in the proximal end portion forming first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth set of cell structures, the cell structures in the distal end portion comprising a sixth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension. In one implementation the first and second peripheral rails are devoid of undulations and the percentage change between the first width dimension and second width dimension is between about 20.0% and about 50.0%.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the cell structures in the proximal end portion forming first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth and fifth set of cell structures, the cell structures in the distal end portion comprising a sixth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the size of the cell structures in the third, fifth and sixth set of cell structures being substantially the same, the size of the cell structures in the fourth set of cell structures being greater than the size of the cell structures in the third, fifth and sixth set of cell structures, the cell structures in the third, fourth, fifth and sixth set of cell structures comprising third, fourth, fifth and sixth struts, respectively, at least some of the fourth and fifth struts, or segments thereof, having a width dimension that is greater than the width dimension of the third and sixth struts.

In another implementation a clot retrieval device is provided comprising: an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the cell structures in the proximal end portion forming first and second peripheral rails having proximal and distal end segments, the cell structures in the proximal end portion comprising a first set of cell structures arranged to form the first peripheral rail, a second set of cell structures arranged to form the second peripheral rail and a third set of cell structures located between the first and second set of cell structures, the first and second set of cell structures having in common a proximal-most cell structure, the cell structures in the main body portion comprising a fourth and fifth set of cell structures, the cell structures in the distal end portion comprising a sixth set of cell structures, the proximal-most cell structure and the first set of cell structures having circumferential outer-most strut members that define the first peripheral rail, the proximal-most cell structure and the second set of cell structures having circumferential outer-most strut members that define the second peripheral rail, at least some of the circumferential outer-most strut members having different width dimensions and arranged so that the first and second peripheral rails vary between a first width dimension at the proximal end segment to second width dimension at the distal end segment, the second width dimension less than the first width dimension, the size of the cell structures in the third, fifth and sixth set of cell structures being substantially the same, the size of the cell structures in the fourth set of cell structures being greater than the size of the cell structures in the third, fifth and sixth set of cell structures, the cell structures in the third, fourth, fifth and sixth set of cell structures comprising third, fourth, fifth and sixth struts, respectively, the width dimension of the third and sixth struts being less than the second width dimension, at least some of the fourth and fifth struts, or segments thereof, having a width dimension substantially equal to the second width dimension.

In other implementations embolic obstruction retrieval devices are provided comprising; an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most wall segments that form first and second rail segments that each extend from a position at or near the proximal-most end of the expandable member to a position at or near the cylindrical main body portion, the proximal-most cell structure of the proximal end portion comprising first and second outer struts that extend distally from the proximal antenna, in a two-dimensional layout at least a portion of each of the first and second outer struts comprise a straight segment, each of the straight segment being coextensive to the proximal antenna.

In other implementations embolic obstruction retrieval devices are provided comprising; an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion, the cell structures in the main body portion extending circumferentially around a longitudinal axis of the expandable member, the cell structures in the proximal and distal end portions extending less than circumferentially around the longitudinal axis of the expandable member, a first set of outer-most cell structures in the proximal end portion having proximal-most wall segments that form a non-undulating rail segment that extends from a position at or near the proximal-most end of the expandable member to a position at or near the cylindrical main body portion, and a second set of outer-most cell structures in the proximal end portion having proximal-most wall segments that form an undulating rail segment that extends from a position at or near the proximal-most end of the expandable member to a position at or near the cylindrical main body portion.

In other implementations embolic obstruction retrieval devices are provided comprising; an elongate self-expandable member having a radially expanded configuration and a radially unexpanded configuration, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion comprising a proximal section and a distal section, the cell structures in the cylindrical main body portion extending circumferentially around a longitudinal axis of the expandable member, the cell structures in the proximal end portion extending less than circumferentially around the longitudinal axis of the expandable member, in the expanded configuration the distal section of the cylindrical main body portion having an average diameter greater than the average diameter of the proximal section of the cylindrical main body portion. In some implementations the average length of the cell structures in the distal section of the cylindrical main body portion is greater than the average length of the cell structures in the proximal section of the cylindrical main body portion, the average length of the cell structures in the proximal section of the cylindrical main body portion being greater than the average length of the cell structures in the proximal end portion, the average length to width ratio of the cell structures in the proximal end portion and cylindrical main body portion being greater than one when the self-expandable member is in the constrained and unconstrained configuration.

In other implementations embolic obstruction retrieval devices are provided comprising; an elongate self-expandable member having a radially expanded configuration and a radially unexpanded configuration, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion comprising a proximal section and a distal section, the cell structures in the cylindrical main body portion extending circumferentially around a longitudinal axis of the expandable member, the cell structures in the proximal end portion extending less than circumferentially around the longitudinal axis of the expandable member, the average length to width ratio of the cell structures in the distal section of the cylindrical main body portion being greater than the average length to width ratio of the cell structures in the proximal section of the cylindrical main body portion, the average length to width ratio of the cell structures in the proximal section of the cylindrical main body portion being greater than the average length to width ratio of the cell structures in the proximal end portion, the average length to width ratio of the cell structures in the proximal end portion being greater than one when the self-expandable member is in the unexpanded and expanded configuration.

In other implementations embolic obstruction retrieval devices are provided comprising; an elongate self-expandable member having a radially expanded configuration and a radially unexpanded configuration, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion, the cell structures in the cylindrical main body portion extending circumferentially around a longitudinal axis of the expandable member, the cell structures in the proximal end portion extending less than circumferentially around the longitudinal axis of the expandable member, the cell structures in the cylindrical main body portion comprising proximal and distal facing V-like structures that are interconnected by a pair of diagonally extending and circumferentially spaced-apart struts, the proximal and distal V-like structures having a first average width dimension and the pair of diagonally extending and circumferentially spaced-apart struts having a second average width dimension that is greater than the first average width dimension.

In other implementations embolic obstruction retrieval devices are provided comprising; an elongate self-expandable member having a radially expanded configuration and a radially unexpanded configuration, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion comprising a proximal section and a distal section, the cell structures in the cylindrical main body portion extending circumferentially around a longitudinal axis of the expandable member, the cell structures in the proximal end portion extending less than circumferentially around the longitudinal axis of the expandable member, the cell structures in the cylindrical main body portion comprising proximal and distal facing V-like structures that are interconnected by a pair of diagonally extending and circumferentially spaced-apart struts, the diagonally extending and circumferentially spaced-apart struts comprising first end segments, second end segments, and a middle segment disposed between the first and second end segments, the first end segments being coupled to the proximal V-like structure and the second end segments being coupled to the distal V-like structure, the proximal and distal V-like structures having a first average width dimension, the middle segments of the diagonally extending and circumferentially spaced-apart struts having a second average width dimension that is greater than the first average width dimension, the first and second end segments of the diagonally extending and circumferentially spaced-apart struts having a third average width dimension that is greater than the first average width dimension and less than the second average width dimension.

In other implementations embolic obstruction retrieval devices are provided comprising; an elongate self-expandable member having a radially expanded configuration and a radially unexpanded configuration, the expandable member comprising a plurality of generally longitudinal undulating elements with adjacent undulating elements being interconnected in a manner to form a plurality of diagonally disposed cell structures, the expandable member having a proximal antenna, a proximal end portion and a cylindrical main body portion comprising a proximal section and a distal section, the cell structures in the cylindrical main body portion extending circumferentially around a longitudinal axis of the expandable member, the cell structures in the proximal end portion extending less than circumferentially around the longitudinal axis of the expandable member, the cell structures in the cylindrical main body portion comprising proximal and distal V-like structures that are interconnected by a pair of diagonally extending and circumferentially spaced-apart struts, at least some of the diagonally extending and circumferentially spaced-apart struts having one or more wires or ribbons wound thereabout so as to enhance the average deflection stiffness of all or a portion of the cylindrical main body portion when the self-expandable member is in the radially expanded configuration.

BRIEF DESCRIPTION OF THE DRAWINGS

Alternative implementations of the present disclosure are described herein with reference to the drawings wherein:

FIG. 7A illustrates a two-dimensional plane view of an expandable member of a treatment device in another embodiment.

FIGS. 13A through 13C illustrate a method for retrieving an embolic obstruction in accordance with one implementation.

FIG. 34A illustrates a two-dimensional plane view of clot retrieval devices according some implementations.

FIG. 35A illustrates a two-dimensional plane view of clot retrieval devices according some implementations.

FIGS. 45A-C illustrate two-dimensional plane views of clot retrieval devices according some implementations.

FIG. 58A illustrates a two-dimensional plane view of a retrieval device according to some implementations.

FIG. 59A illustrates a side view of a joint member according to one implementation.

DETAILED DESCRIPTION

Figure 1A:
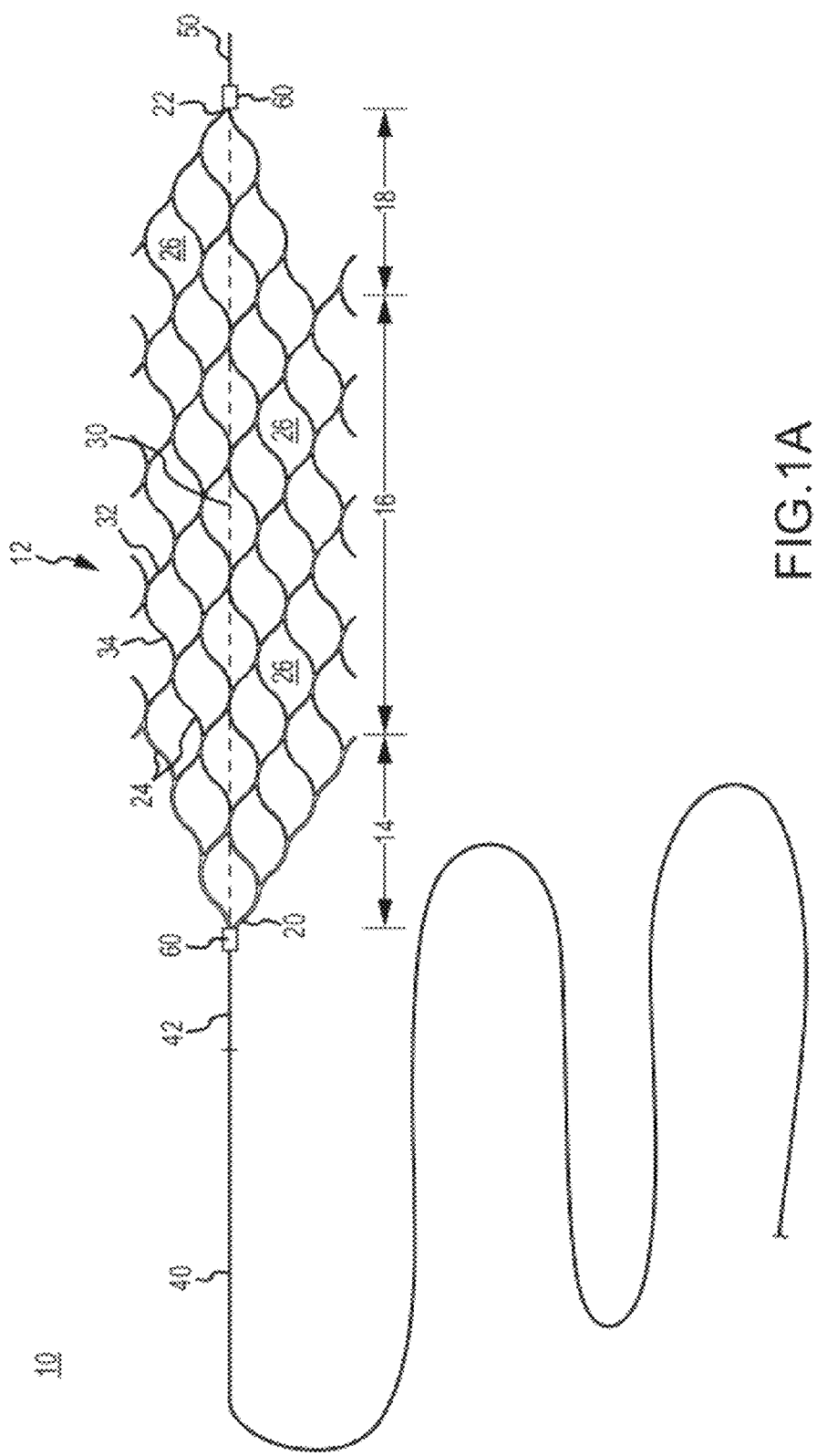
FIG. 1A illustrates a two-dimensional plane view of an expandable member of a treatment device in one embodiment.
Figure 1B:
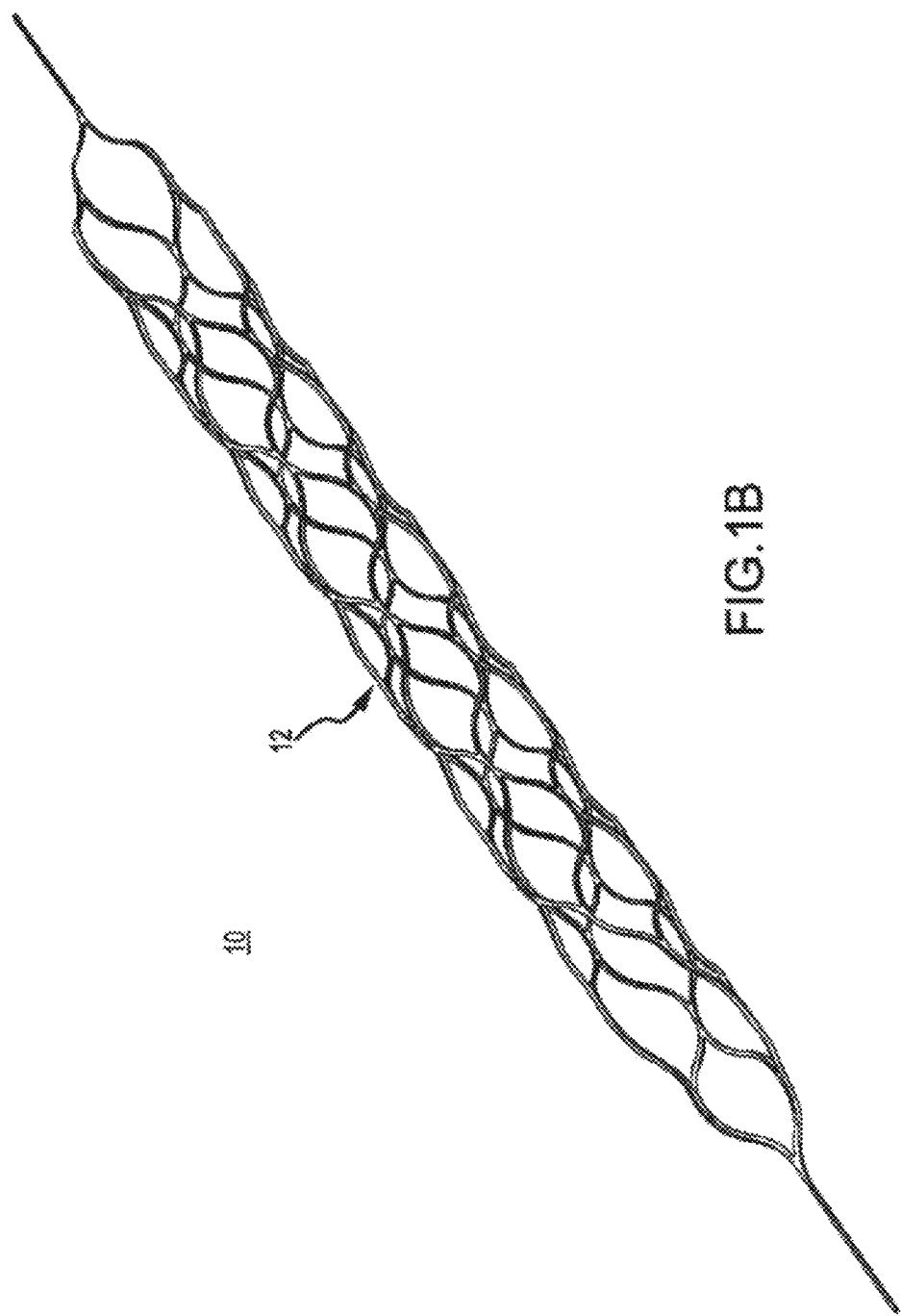
FIG. 1B is an isometric view of the expandable member illustrated in FIG. 1A

FIGS. 1A and 1B illustrate a vascular or bodily duct treatment device 10 in accordance with one embodiment of the present invention. Device 10 is particularly suited for accessing and treating the intracranial vascular of a patient, such as for example treating aneurysms or capturing and removing embolic obstructions. It is appreciated however, that device 10 may be used for accessing and treating other locations within the vasculature and also other bodily ducts. Other uses include, for example, treating stenoses and other types of vascular diseases and abnormalities. FIG. 1A depicts device 10 in a two-dimensional plane view as if the device were cut and laid flat on a surface. FIG. 1B depicts the device in its manufactured and/or expanded tubular configuration. Device 10 includes a self-expandable member 12 that is attached or otherwise coupled to an elongate flexible wire 40 that extends proximally from the expandable member 12. In one embodiment, the expandable member 12 is made of shape memory material, such as Nitinol, and is preferably laser cut from a tube. In one embodiment, the expandable member 12 has an integrally formed proximally extending wire segment 42 that is used to join the elongate flexible wire 40 to the expandable member 12. In such an embodiment, flexible wire 40 may be joined to wire segment 42 by the use of solder, a weld, an adhesive, or other known attachment method. In an alternative embodiment, the distal end of flexible wire 40 is attached directly to a proximal end 20 of the expandable member 12. In one embodiment, the distal end of wire 40 has a flat profile with a width of about 0.005 inches with the width and thickness of the wire segment 42 being about 0.0063 and about 0.0035 inches, respectively.

Figure 25:
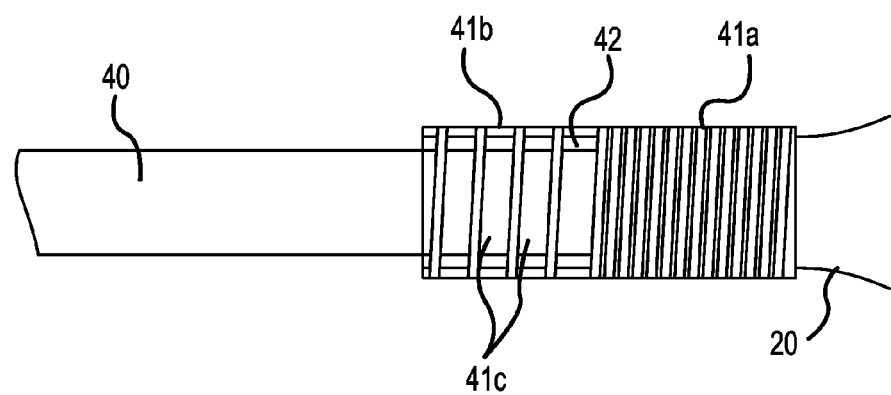
FIG. 25 illustrates a manner in which the proximal extending wire segment of an expandable device is attached to a delivery wire in one embodiment.

In one embodiment, the distal end of wire 40 is attached to the proximally extending wire segment 42 by the following method, resulting in the joint illustrated in FIG. 25. In one implementation, a coil 41 is positioned over wire segment 42, the coil having a closely wrapped segment 41a abutting the proximal end of expandable member 12, and a loosely wrapped segment 41b that includes one or more gaps 41c. The size of the one or more gaps 41c being sufficient to introduce a bonding agent into at least the inner cavity of coil segment 41b. In one embodiment, the length of wire segment 42 and the coil 41 are equal. In one embodiment the length of the wire segment 42 is 4.0 millimeters with the coil 41 being of equal length. Once the coil 41 has been placed over the wire segment 42, the distal end of wire 40 is placed within coil segment 41b so that it makes contact with and overlaps the proximal end portion of wire segment 42. A bonding agent is then applied through the gaps 41c of coil 41 to bond the wire 40 with wire segment 41. The bonding agent may be an adhesive, solder, or any other suitable bonding agent. When the bonding agent is a solder, a preceding step in the process involves coating the distal end portion of wire 40 and the proximal end portion of wire segment 42 with tin or another suitable wetting agent. In one implementation the solder is gold and is used to enhance the radiopacity of the joint so that the joint may serve as a proximal radiopaque marker. In addition to the use of gold, all or portions of the coil may be made of a radiopaque material to further enhance the radiopacity of the joint. According to one embodiment, the length of overlap between the wire 40 and wire segment 42 is between 0.75 and 1.0 millimeters. In the same implementation or in other implementations, the length of coil segment 41b is equal, or substantially equal, to the overlap length of the wire 40 and wire segment 42. In an alternative embodiment, in lieu of the use of a single coil 41, two or more coils in abutting relationship are used with, for example, a first closely wound coil abutting the proximal end 20 of the expandable member 12 and a second loosely wound coil with gaps situated proximal to the closely wound coil. Although not shown in the figures, in one embodiment a distal end length of wire 40 is tapers in the distal direction from a nominal diameter to a reduced profile. Along this length is provided a distal wire coil of a constant outer diameter with no taper. In accordance with one implementation, the diameter of coil 41 has the same outer diameter as the distal wire coil.

One advantage of the joint construction is that it is resistant to buckling while the device is being pushed through a delivery catheter while at the same time being sufficiently flexible to enable the device to be delivered through the tortuous anatomy of a patient. In addition, the joint is able to withstand high tensile and torque loads without breaking Load test have shown the joint of the previously described embodiment can withstand in excess of 2 pounds of tensile stress. In one embodiment, coil 41 is made of a radiopaque material to also function as a proximal radiopaque marker.

Figure 28A:
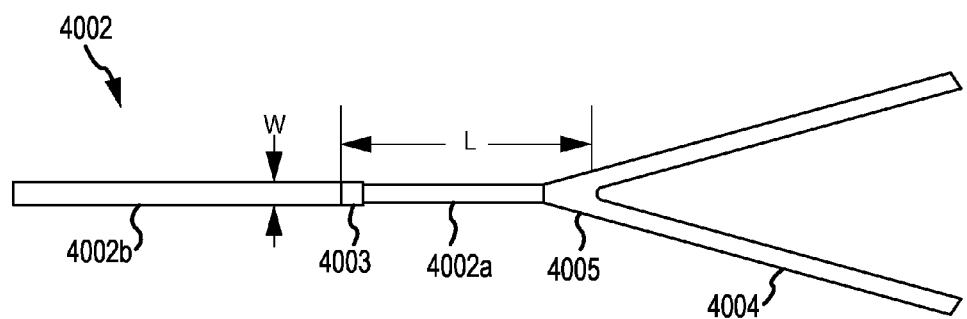
FIGS. 28A and 28B illustrate a proximal wire segment and a distal wire segment, respectively, of an expandable member in one implementation.

FIG. 28A depicts an alternative proximal wire segment construction. As shown, the proximal wire segment 4002 comprises a first section 4002a and a second section 4002b, with the second section 4002b having a width W greater than the width of the first section. In one implementation a tapered transition section 4003 joins the first and second sections 4002a and 4002b. In one implementation the width of the first section 4002a is about 0.0063 inches while the width W of the second section is between about 0.0085 inches and about 0.0105 inches. In one implementation the length L between the proximal end 4005 of the expandable member 4004 and second section 4002b of the wire segment 4002 is between about 0.017 inches and about 0.022 inches. An advantage of the inclusion of the second section 4002b is that the greater width dimension provides a larger surface area for bonding the wire segment 4002 to the elongate wire 40 used in the delivery and retraction of the elongate member from a duct of a patient. In one implementation the first section 4002a has a circular or substantially circular construction and the second section 4002b has a flat profile formed by a pressing/coining operation.

In the embodiment of FIGS. 1A and 1B, expandable member 12 includes a plurality of generally longitudinal undulating elements 24 with adjacent undulating elements being out-of-phase with one another and connected in a manner to form a plurality of diagonally disposed cell structures 26. The expandable member 12 includes a proximal end portion 14, a cylindrical main body portion 16 and a distal end portion 18 with the cell structures 26 in the main body portion 16 extending continuously and circumferentially around a longitudinal axis 30 of the expandable member 12. The cell structures 26 in the proximal end portion 14 and distal end portion 18 extend less than circumferentially around the longitudinal axis 30 of the expandable member 12.

In one embodiment, expandable member 12 has an overall length of about 33.0 millimeters with the main body portion 16 measuring about 16.0 millimeters in length and the proximal and distal end portions 14 and 18 each measuring about 7.0 millimeters in length. In alternative embodiments, the length of the main body portion 16 is generally between about 2.5 to about 3.5 times greater than the length of the proximal and distal end portions 14 and 18.

In use, expandable member 12 is advanced through the tortuous vascular anatomy or bodily duct of a patient to a treatment site in an unexpanded or compressed state (not shown) of a first nominal diameter and is movable from the unexpanded state to a radially expanded state of a second nominal diameter greater than the first nominal diameter for deployment at the treatment site. In alternative exemplary embodiments the first nominal diameter (e.g., average diameter of main body portion 16) ranges between about 0.017 to about 0.030 inches, whereas the second nominal diameter (e.g., average diameter of main body portion 16) is between about 2.5 to about 5.0 millimeters. In one implementation, the dimensional and material characteristics of the cell structures 26 residing in the main body portion 16 of the expandable material 12 are selected to produce sufficient radial force and contact interaction to cause the cell structures 26 to engage with an embolic obstruction residing in the vascular in a manner that permits partial or full removal of the embolic obstruction from the patient. In alternative embodiments the dimensional and material characteristics of the cell structures 26 in the main body portion 16 are selected to produce a radial force per unit length of between about 0.005 N/mm to about 0.050 N/mm, preferable between about 0.010 N/mm to about 0.050 N/mm, and more preferably between about 0.030 N/mm and about 0.050 N/mm. In one embodiment, the diameter of the main body portion 16 in a fully expanded state is about 4.0 millimeters with the cell pattern, strut dimensions and material being selected to produce a radial force of between about 0.040 N/mm to about 0.050 N/mm when the diameter of the main body portion is reduced to between about 1.0 millimeters to about 1.5 millimeters. In the same or alternative embodiment, the cell pattern, strut dimensions and material(s) are selected to produce a radial force of between about 0.010 N/mm to about 0.020 N/mm when the diameter of the main body portion is reduced to 3.0 millimeters.

In the embodiments of FIGS. 1A and 1B, each of the cell structures 26 are shown having the same dimensions with each cell structure including a pair of short struts 32 and a pair of long struts 34. In an exemplary embodiment, struts 32 have a length of between about 0.080 and about 0.100 inches, struts 34 have a length of between about 0.130 and about 0.140 inches, with each of struts 32 and 34 having an as-cut width and thickness of about 0.003 inches and about 0.0045 inches, respectively, and a post-polishing width and thickness of between about 0.0022 inches and about 0.0039 inches, respectively. An advantage of having a strut thickness to width ratio of greater than one is that it promotes integration of the strut into the embolic obstruction. In alternative embodiments, the post-polishing width and thickness dimensions varies between about 0.0020 inches to about 0.0035 and about 0.0030 inches to about 0.0040 inches, respectively, with the thickness to width ratio varying between about 1.0 to about 2.0, and preferably between about 1.25 to about 1.75.

In one embodiment, only the strut elements of the main body portion 16 have a thickness to width dimension ratio of greater than one. In another embodiment, only the strut elements of the main body portion 16 and distal end portion 18 have a thickness to width dimension ratio of greater than one. In another embodiment, only a portion of the strut elements have a thickness to width dimension ratio of greater than one. In yet another embodiment, strut elements in different parts of the expandable member have different thickness to width dimension ratios, the ratios in each of the parts being greater than one. As an example, because the radial force exerted by the proximal end portion 14 and distal end portion 18 of the expandable member 12 may generally be less than the radial force exerted by the main body portion 16, the strut elements in the distal and/or proximal end portions can have a thickness to width ratio that is greater than the thickness to width ratio of the struts in the main body portion 16. An advantage of this construction is that the ability of the expandable member 12 to integrate into an embolic obstruction is made to be more uniform along the length of the expandable member.

In other embodiments, certain, or all of the strut elements have a tapered shape with the outer face of the strut having a width dimension less than the width dimension of the inner face of the strut. In other embodiments, the expandable member 12 may comprise strut elements having a generally rectangular cross-section and also strut elements having a tapered shape.

It is important to note that the present invention is not limited to expandable members 12 having uniform cell structures nor to any particular dimensional characteristics. As an example, in alternative embodiments the cell structures 26 in the proximal and/or distal end portions 14 and 18 are either larger or smaller in size than the cell structures 26 in the main body portion 16. In one embodiment, the cell structures 26 in the proximal and distal end portions 14 and 18 are sized larger than those in the main body portion 16 so that the radial forces exerted in the end portions 14 and 18 are lower than the radial forces exerted in the main body portion 16.

The radial strength along the length of the expandable member 12 may be varied in a variety of ways. One method is to vary the mass (e.g., width and/or thickness) of the struts along the length of the expandable member 12. Another method is to vary the size of the cell structures 26 along the length of the expandable member 12. The use of smaller cell structures will generally provide higher radial forces than those that are larger. Varying the radial force exerted along the length of the expandable member can be particularly advantageous for use in entrapping and retrieving embolic obstructions. For example, in one embodiment the radial force in the distal section of the main body portion 16 of the expandable member 12 in its expanded state is made to be greater than the radial force in the proximal section of the main body portion 16. Such a configuration promotes a larger radial expansion of the distal section of the main body portion 16 into the embolic obstruction as compared to the proximal section. Because the expandable member 12 is pulled proximally during the removal of the embolic obstruction from the patient, the aforementioned configuration will reduce the likelihood of particles dislodging from the embolic obstruction during its removal. In an alternative embodiment the radial force in the proximal section of the main body portion 16 of the expandable member 12 in its expanded state is made to be greater than the radial force in the distal section of the main body portion 16. In yet another embodiment, the main body portion 16 of the expandable member 12 includes a proximal section, a midsection and a distal section with the radial force in the proximal and distal sections being larger than the radial force in the midsection when the expandable member 12 is in an expanded state.

Figure 9:
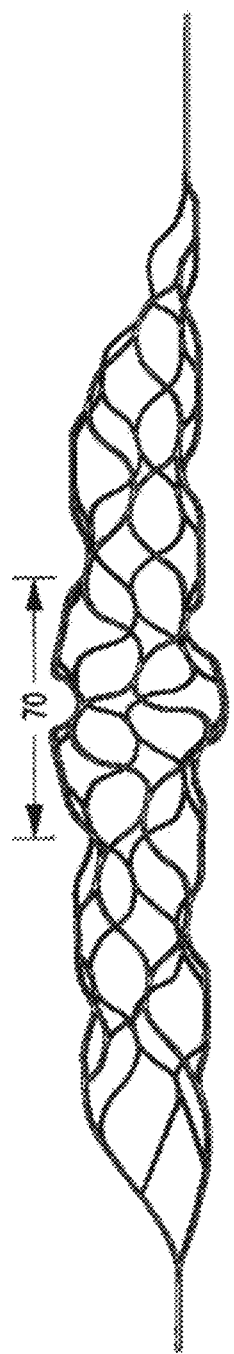
FIG. 9 illustrates an expandable member in an expanded position having a bulge or increased diameter portion.

In alternative embodiments, as exemplified in FIG. 9, the main body portion 16 may include an increased diameter portion or bulge 70 to enhance the expandable member's ability to entrap or otherwise engage with an embolic obstruction. In FIG. 9, a single increased diameter portion 70 is provided within the midsection of main body portion 16. In alternative embodiments, the increased diameter portion 70 may be positioned proximally or distally to the midsection. In yet other embodiments, two or more increased diameter portions 70 may be provided along the length of the main body portion 16. In one implementation, the two or more increased diameter portions 70 have essentially the same manufactured nominal diameter. In another implementation, the distal-most increased diameter portion 70 has a greater manufactured nominal diameter than the proximally disposed increased diameter portions. In alternative exemplary embodiments the nominal diameter of the increased diameter portion 70 is between about 25.0 to about 45.0 percent greater than the nominal diameter of the main body portion. For example, in one embodiment, the nominal expanded diameter of main body portion 16 is about 3.0 millimeters and the nominal diameter of the increased diameter portion 70 is about 4.0 millimeters. In another embodiment the nominal expanded diameter of main body portion 16 is about 3.50 millimeters and the nominal diameter of the increased diameter portion 70 is about 5.00 millimeters. In one embodiment, the one or more increased diameter portions 70 are formed by placing an expandable mandrel into the internal lumen of the main body portion 16 and expanding the mandrel to create the increased diameter portion 70 of a desired diameter. In another embodiment, one or more of the increased diameter portions 70 are formed by placing a mandrel of a given width and diameter into the main body portion 16 and then crimping the expandable member 12 in a manner to cause at least a portion of the main body portion 16 to be urged against the mandrel.

In one embodiment, the strut elements in the increased diameter portion or portions 70 have a thickness dimension to width dimension ratio that is greater than the thickness to width ratio of the other struts in the main body portion 16. In yet another embodiment, the strut elements in the increased diameter portion or portions 70 have a thickness dimension to width dimension ratio that is less than the thickness to width ratio of the other struts in the main body portion 16.

Figure 2:
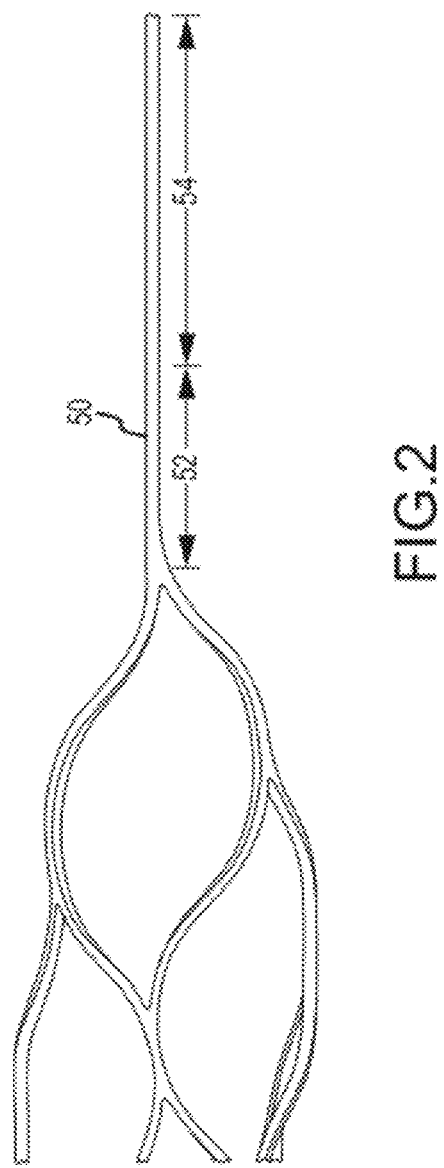
FIG. 2 illustrates a distal wire segment that extends distally from an expandable member in one embodiment.
Figure 3:
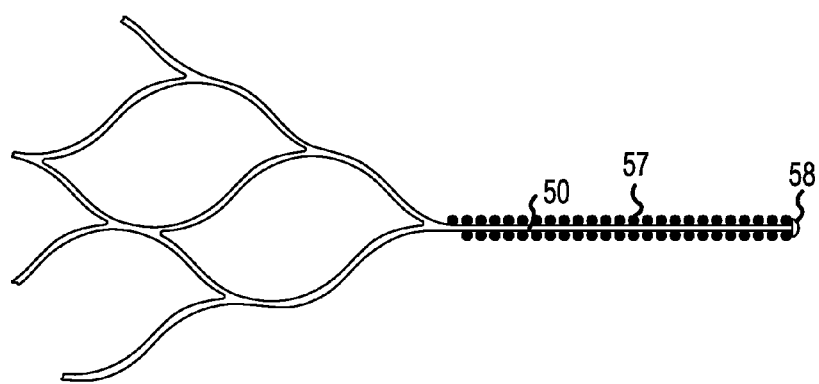
FIG. 3 illustrates the distal end of an expandable member having an atraumatic tip.

In one implementation, a distal wire segment 50, that is attached to or integrally formed with expandable member 12, extends distally from the distal end 22 of the expandable member 12 and is configured to assist in guiding the delivery of the expandable member to the treatment site of a patient. FIG. 2 shows a distal wire segment 50 in one embodiment having a first section 52 of a uniform cross-section and a second section 54 having a distally tapering cross-section. In an exemplary embodiment, the first section 52 has a length of about 3.0 millimeters and an as-cut cross-sectional dimension of about 0.0045 inches by about 0.003 inches, and whereas the second section 54 has a length of about 4.0 millimeters and tapers to a distal-most, as-cut, cross-sectional dimension of about 0.002 inches by about 0.003 inches. Post-polishing of the device generally involves an etching process that typically results in a 40% to 50% reduction in the as-cut cross-sectional dimensions. In another embodiment, as depicted in FIG. 3, the distal wire segment 50 is bound by a spring member 57 of a uniform diameter and is equipped with an atruamatic distal tip 58. In alternative embodiments, the spring element 57 and/or the atraumatic tip 58 are made or coated with of a radiopaque material, such as, for example, platinum.

Figure 28B:
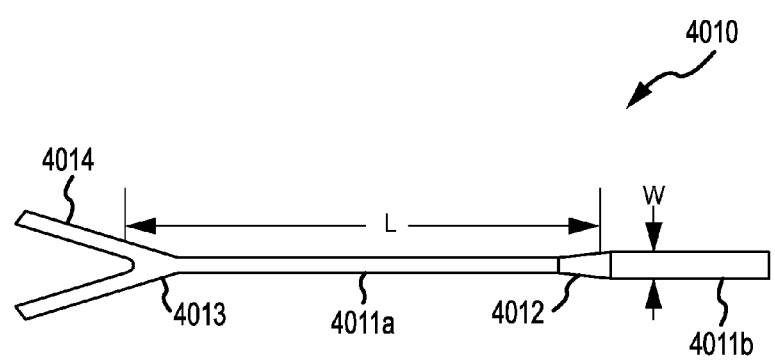

FIG. 28b illustrates an alternative distal wire segment construction. As depicted, the distal wire segment 4010 includes a first section 4011a and a second section 4011b, the second section 4011b having a width W greater than the width of the first section 4011a. In one implementation a tapered transition section 4012 joins the first and second sections 4011a and 4011b. In one implementation the width W of the second section is between about 0.003 inches and about 0.004 inches with the length L between the distal end 4013 of the expandable member 4014 and the second section 4011b of the wire segment 4010 being between about 0.015 inches and about 0.020 inches. An advantage of the inclusion of the second section 4011b is that the greater width dimension provides a larger surface area for bonding a coil/spring segment 57 to the wire segment 4010. In one implementation the first section 4011a has a circular or substantially circular construction and the second section 4011b has a flat profile formed by a pressing/coining operation.

In one embodiment, as will be described in more detail below, the expandable member 12 is delivered to the treatment site of a patient through the lumen of a delivery catheter that has been previously placed at the treatment site. In an alternative embodiment, the vascular treatment device 10 includes a sheath that restrains the expandable member 12 in a compressed state during delivery to the treatment site and which is proximally retractable to cause the expandable member 12 to assume an expanded state.

In one implementation, the expandable member 12 in the expanded state is able to engage an embolic obstruction residing at the treatment site, for example by embedding itself into the obstruction, and is removable from the patient by pulling on a portion of the elongate flexible wire 40 residing outside the patient until the expandable member 12 and at least a portion of the embolic obstruction are removed from the patient.

The use of interconnected and out-of-phase undulating elements 24 to create at least some of the cell structures 26 in alternative embodiments provides several advantages. First, the curvilinear nature of the cell structures 26 enhances the flexibility of the expandable member 12 during its delivery through the tortuous anatomy of the patient to the treatment site. In addition, the out-of-phase relationship between the undulating elements facilitates a more compact nesting of the expandable member elements permitting the expandable member 12 to achieve a very small compressed diameter. A particular advantage of the expandable member strut pattern shown in FIG. 1A, and various other embodiments described herein, is that they enable sequential nesting of the expandable member elements which permit the expandable members to be partially or fully deployed and subsequently withdrawn into the lumen of a delivery catheter. The out-of-phase relationship also results in a diagonal orientation of the cell structures 26 which may induce a twisting action as the expandable member 12 transitions between the compressed state and the expanded state that helps the expandable member to better engage with the embolic obstruction. In alternative embodiments, the cell structures 26 of the expandable member 12 are specifically arranged to produce a desired twisting action during expansion of the expandable member 12. In this manner, different expandable members each having different degrees of twisting action may be made available to treat, for example, different types of embolic obstructions.

To enhance visibility of the device under fluoroscopy, the expandable member may be fully or partially coated with a radiopaque material, such as tungsten, platinum, platinum/iridium, tantalum and gold. Alternatively, or in conjunction with the use of a radiopaque coating, radiopaque markers 60 may be positioned at or near the proximal and distal ends 20 and 22 of the expandable device and/or along the proximal and distal wire segments 42 and 50 and/or on selected expandable member strut segments. In one embodiment, the radiopaque markers 60 are radiopaque coils, such as platinum coils.

Figure 4A:
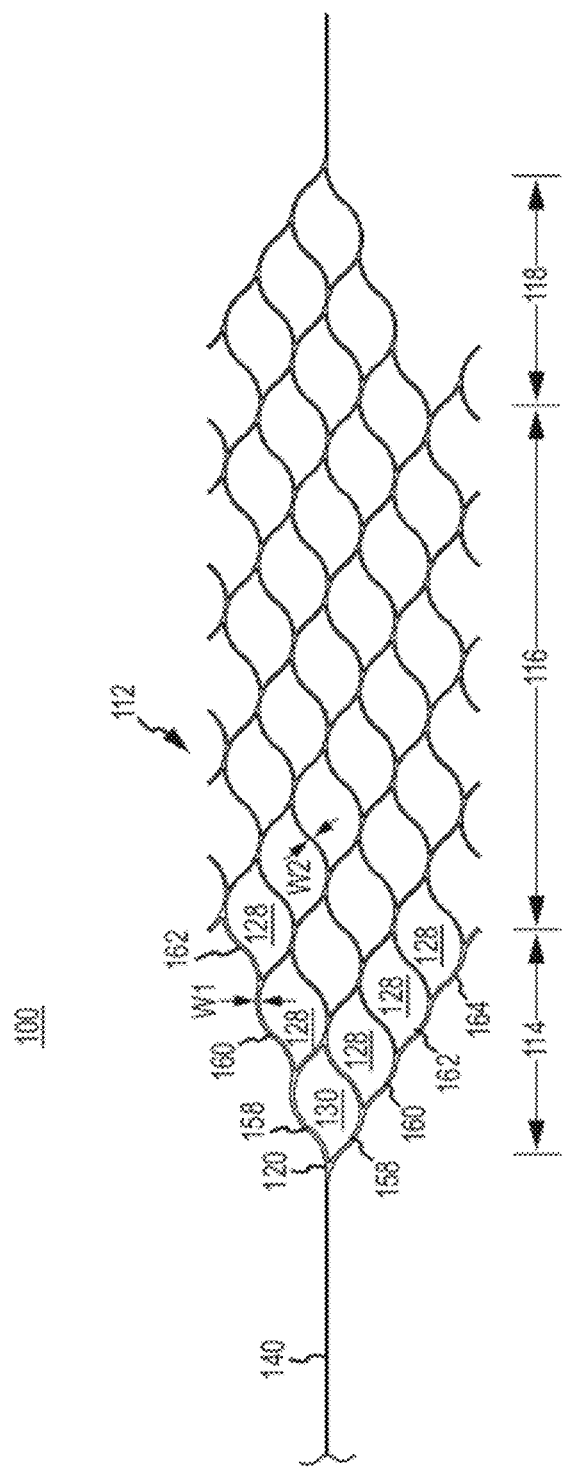
FIG. 4A illustrates a two-dimensional plane view of an expandable member of a treatment device in another embodiment.
Figure 4B:
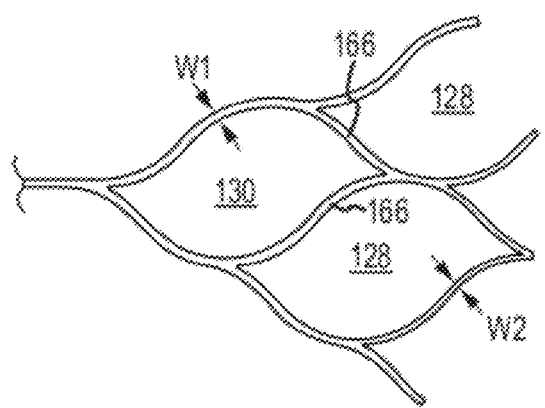
FIG. 4B is an enlarged view of the proximal-most segment of the expandable member illustrated in FIG. 4A.

FIG. 4A depicts a vascular treatment device 100 in a two-dimensional plane view in another embodiment of the present invention. In its manufactured and/or expanded tubular configuration, device 100 has a similar construction as device 10 shown in FIG. 1B. Like device 10 described above in conjunction with FIGS. 1A and 1B, device 100 includes a self-expandable member 112 that is coupled to an elongate flexible wire 140. The expandable member 112 includes a proximal end portion 114, a cylindrical main body portion 116 and a distal end portion 118. As mentioned above, delivery of the expandable member 112 in its unexpanded state to the treatment site of a patient is accomplished in one manner by placing the expandable member 112 into the proximal end of a delivery catheter and pushing the expandable member 112 through the lumen of the delivery catheter until it reaches a distal end of the catheter that has been previously placed at or across the treatment site. The proximally extending elongate flexible wire 140 which is attached to or coupled to the proximal end 120 of the expandable member 112 is designed to transmit a pushing force applied to it to its connection point with the elongate flexible member 112. As shown in FIG. 4A, and in more detail in FIG. 4B, device 100 is distinguishable from the various embodiments of device 10 described above in that the proximal-most cell structures 128 and 130 in the proximal end portion 114 include strut elements having a width dimension W1 larger than the width dimension W2 of the other strut elements within the expandable member 112. As shown, the proximal-most wall sections 160, 162 and 164 of cell structures 128 are made of struts having width W1. Moreover, all the struts of the proximal-most cell structure 130 have an enhanced width W1. The inclusion and placement of the struts with width W1 provides several advantages. One advantage is that they permit the push force applied by the distal end of the elongate wire 140 to the proximal end 120 of elongate member 112 to be more evenly distributed about the circumference of the expandable member 112 as it is being advanced through the tortuous anatomy of a patient. The more evenly distributed push force minimizes the formation of localized high force components that would otherwise act on individual or multiple strut elements within the expandable member 112 to cause them to buckle. Also, by including the struts of width W1 in the peripheral regions of proximal end portion 114, they greatly inhibit the tendency of the proximal end portion 114 to buckle under the push force applied to it by elongate wire 140. In one exemplary embodiment the as-cut width dimension W1 is about 0.0045 inches and the as-cut width dimension W2 is about 0.003 inches. As discussed above, post-polishing of the device generally involves an etching process that typically results in a 40% to 50% reduction in the as-cut cross-sectional dimensions.

It is important to note that although the width dimension W1 is shown as being the same among all struts having an enhanced width, this is not required. For example, in one embodiment wall segments 158 may have an enhanced width dimension greater than the enhanced width dimension of wall segments 160, and wall segments 160 may have an enhanced width dimension greater than the enhanced width dimension of wall segments 162, and so on. Moreover, the inner strut elements 166 of the proximal-most cell structure 130 may have an enhanced width dimension less than the enhanced width dimensions of struts 158. Also, in alternative embodiments, the radial thickness dimension of struts 158, 160, 162, 164, etc. may be enhanced in lieu of the width dimension or in combination thereof.

Figure 5:
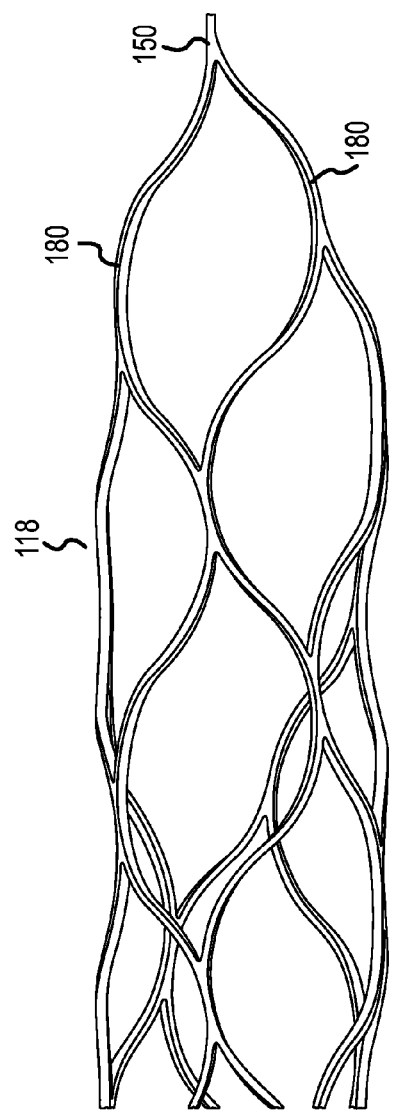
FIG. 5 illustrates a distal end of an expandable member in one embodiment.

In yet another embodiment, as shown in FIG. 5, some of the strut elements 180 in the distal end portion 118 of the expandable member 112 have a mass greater than that of the other struts to resist buckling and possible breaking of the struts as device 100 is advanced to a treatment site of a patient. In the embodiment shown, struts 180 are dimensioned to have the same width as distal wire segment 150. In alternative embodiments, the thickness dimension of struts 180 may be enhanced in lieu of the width dimension or in combination thereof.

Figure 6A:
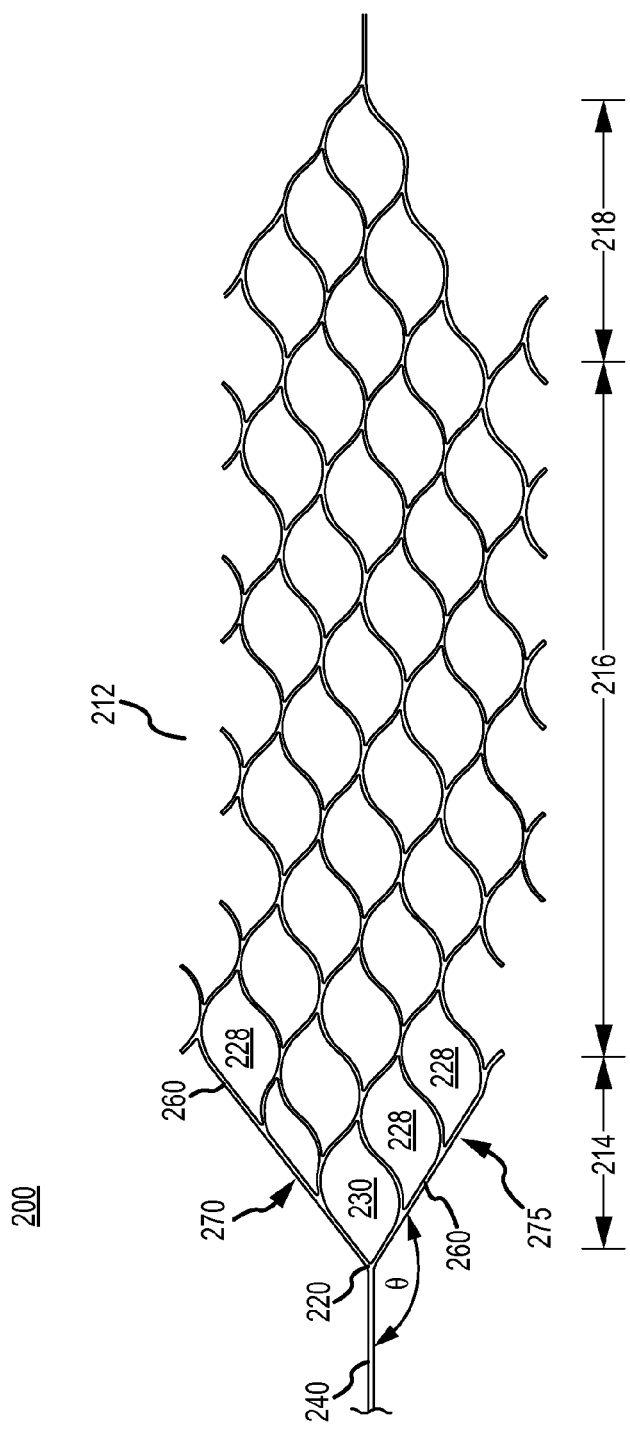
FIG. 6A illustrates a two-dimensional plane view of an expandable member of a treatment device in another embodiment.
Figure 6B:
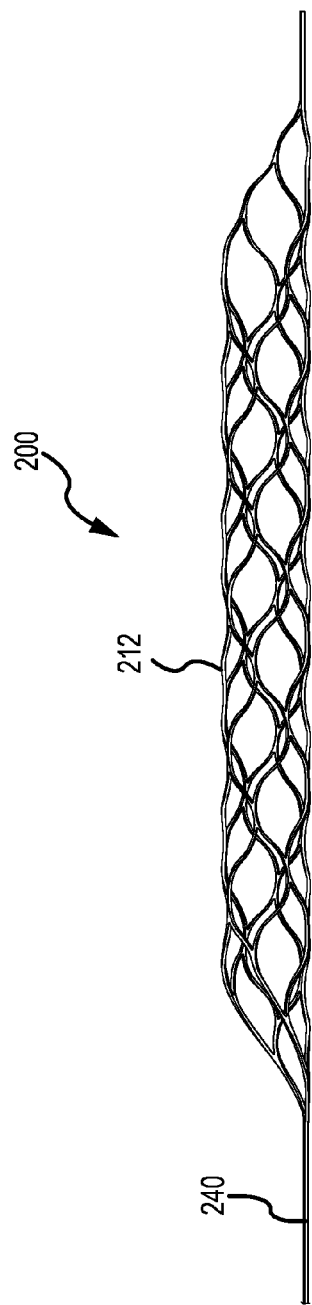
FIG. 6B is an isometric view of the expandable member illustrated in FIG. 6A.

FIGS. 6A and 6B illustrate a vascular treatment device 200 in accordance with another embodiment of the present invention. FIG. 6A depicts device 200 in a two-dimensional plane view as if the device were cut and laid flat on a surface. FIG. 6B depicts the device in its manufactured and/or expanded tubular configuration. Device 200 includes an expandable member 212 having a proximal end portion 214, a cylindrical main body portion 216 and a distal end portion 218 with an elongate flexible wire 240 attached to or otherwise coupled to the proximal end 220 of the expandable member. The construction of device 200 is similar to device 100 described above in conjunction with FIG. 4A except that the proximal wall segments 260 of cell structures 228 and 230 comprise linear or substantially linear strut elements as viewed in the two dimension plane view of FIG. 6A. In one embodiment, the linear strut elements 260 are aligned to form continuous and substantially linear rail segments 270 that extend from the proximal end 220 of proximal end portion 214 to a proximal-most end of main body portion 216 (again, as viewed in the two dimension plane view of FIG. 6A) and preferably are of the same length, but may be of different lengths. When the pattern of FIG. 6A is applied to laser cutting a tubular structure, the resulting expandable member configuration is that as shown in FIG. 6B. As shown in FIG. 6B, rail segments 270 are not in fact linear but are of a curved and non-undulating shape. This configuration advantageously provides rail segments 270 devoid of undulations thereby enhancing the rail segments' ability to distribute forces and resist buckling when a push force is applied to them. In alternative preferred embodiments, the angle $\theta$ between the wire segment 240 and rail segments 270 ranges between about 140 degrees to about 150 degrees. In one embodiment, one or both of the linear rail segments 270 have a width dimension W1 which is greater than the width dimension of the adjacent strut segments of cell structures 228 and 230. An enhanced width dimension W1 of one or both the linear rail segments 270 further enhances the rail segments' ability to distribute forces and resist buckling when a push force is applied to them. In another implementation, one or both of the linear rail segments 270 are provided with an enhanced thickness dimension, rather than an enhanced width dimension to achieve the same or similar result. In yet an alternative implementation, both the width and thickness dimensions of one or both of the linear rail segments 270 are enhanced to achieve the same or similar results. In yet another implementation, the width and/or thickness dimensions of each of the rail segments 270 differ in a manner that causes a more even compression of the proximal end portion 214 of the expandable member 212 when it is loaded or retrieved into a delivery catheter or sheath (not shown).

Figure 7B:
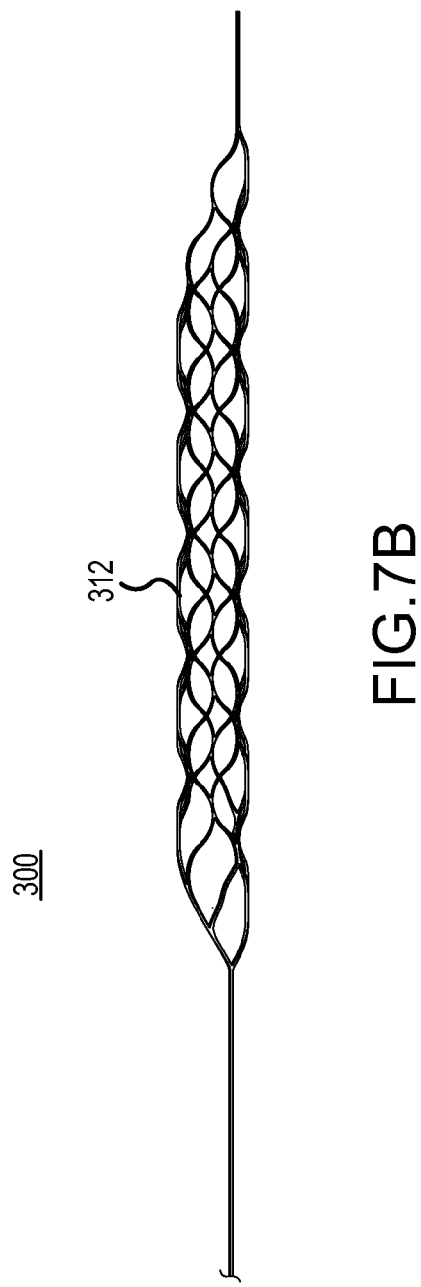
FIG. 7B is an isometric view of the expandable member illustrated in FIG. 7A.

FIGS. 7A and 7B illustrate a vascular treatment device 300 in accordance with another embodiment of the present invention. FIG. 7A depicts device 300 in a two-dimensional plane view as if the device were cut and laid flat on a surface. FIG. 7B depicts the device in its manufactured and/or expanded tubular configuration. Device 300 includes an expandable member 312 having a proximal end portion 314, a cylindrical main body portion 316 and a distal end portion 318 with an elongate flexible wire 340 attached to or otherwise coupled to the proximal end 320 of the expandable member. The construction of device 300 is similar to device 200 described above in conjunction with FIGS. 6A and 6B except that the proximal-most cell structure 330 comprises a substantially diamond shape as viewed in the two-dimensional plane of FIG. 7A. The substantially diamond-shaped cell structure includes a pair of outer strut elements 358 and a pair of inner strut elements 360, each having an enhanced width and/or enhanced thickness dimension as previously discussed in conjunction with the embodiments of FIGS. 4 and 6. In alternative preferred embodiments, the inner strut elements 360 intersect the outer strut elements 358 at an angle $\beta$ between about 25.0 degrees to about 45.0 degrees as viewed in the two-dimensional plane view of FIG. 7A. Maintaining the angular orientation between the inner and outer struts within in this range enhances the pushabilty of the expandable member 312 without the occurrence of buckling and without substantially affecting the expandable member's ability to assume a very small compressed diameter during delivery.

Figure 7C:
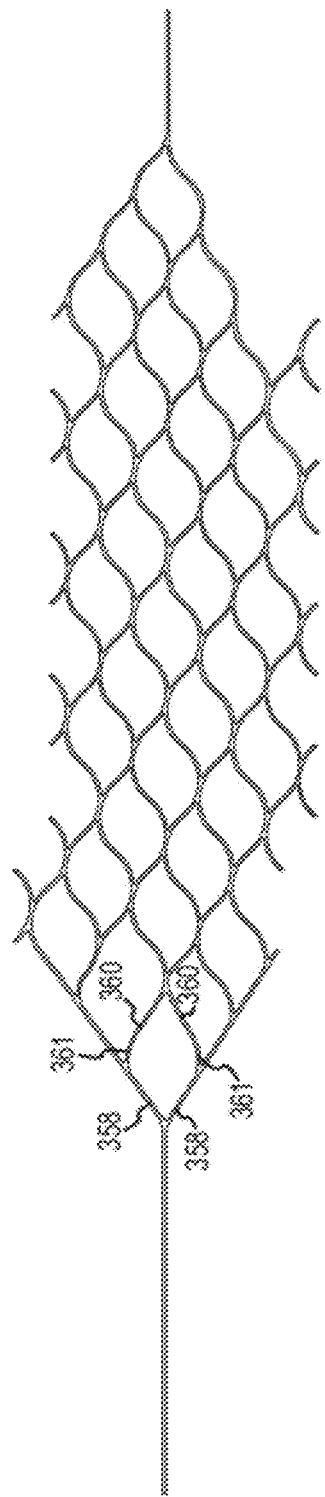
FIG. 7C illustrates a two-dimensional plane view of an expandable member of a treatment device in another embodiment.

In one embodiment, the inner strut elements 360 have a mass less than that of the outer strut elements 358 that enables them to more easily bend as the expandable member 312 transitions from an expanded state to a compressed state. This assists in achieving a very small compressed diameter. In another embodiment, as shown in FIG. 7C, the inner strut elements 360 are coupled to the outer strut elements 358 by curved elements 361 that enable the inner strut elements 360 to more easily flex when the expandable member 312 is compressed to its delivery position.

Figure 8:
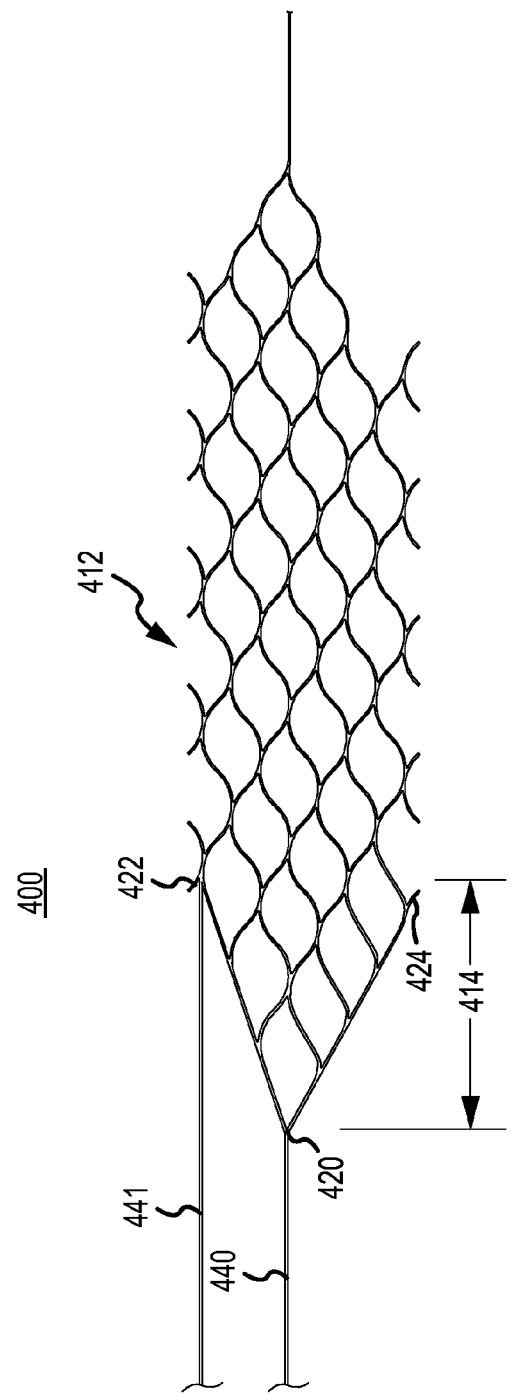
FIG. 8 illustrates a two-dimensional plane view of an expandable member of a treatment device in another embodiment.

FIG. 8 illustrates an alternative embodiment of a vascular treatment device 400. Device 400 has a similar construction to that of device 200 depicted in FIGS. 6A and 6B with the exception that the expandable member 412 of device 400 is connected at its proximal end portion 414 with two distally extending elongate flexible wires 440 and 441. As illustrated, wire 440 is attached to or otherwise coupled to the proximal-most end 420 of proximal end portion 414, while wire 441 is attached to or otherwise coupled to the distal-most end 422 of the proximal end portion 414 at the junction with rail segment 470. In yet another embodiment, an additional elongate flexible wire (not shown) may be attached to the distal-most end 424. The use of two or more elongate flexible wires 440 and 441 to provide pushing forces to the proximal end portion 414 of elongate member 412 advantageously distributes the pushing force applied to the proximal end portion 414 to more than one attachment point.

Figure 10:
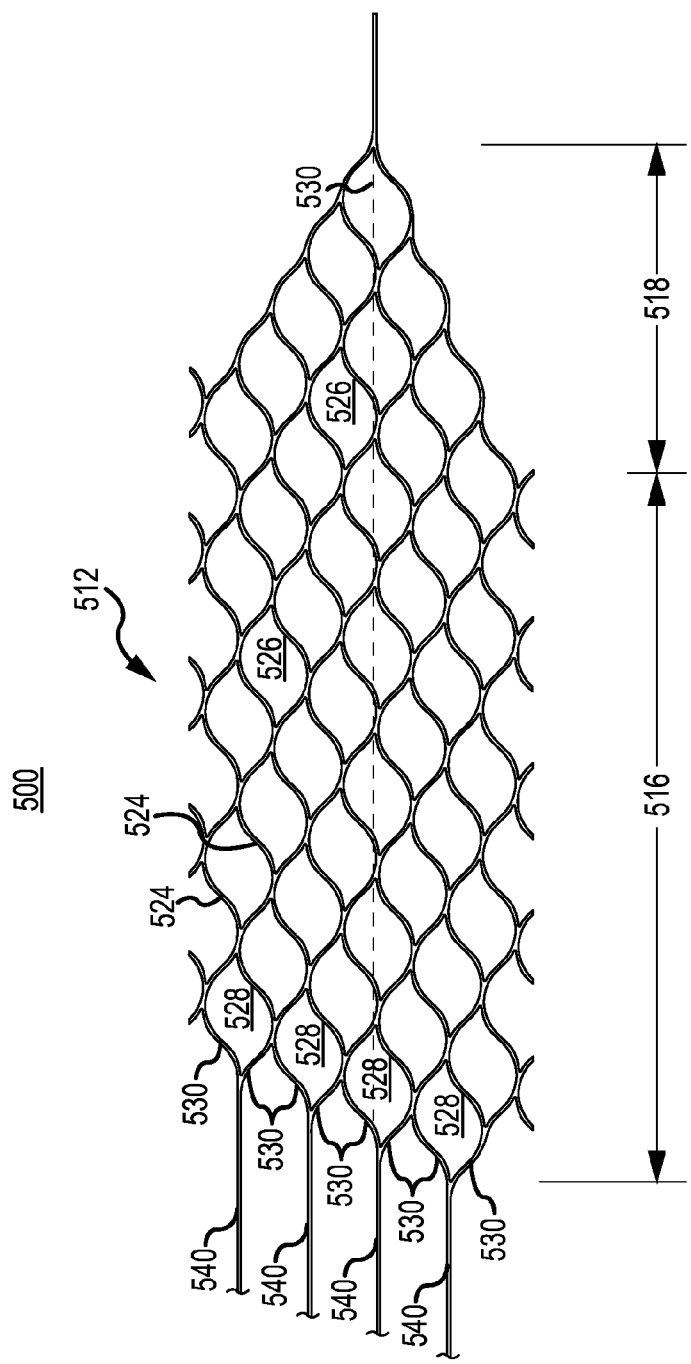
FIG. 10 illustrates a two-dimensional plane view of an expandable member of a treatment device in another embodiment.

FIG. 10 illustrates a two-dimensional plane view of a vascular treatment device 500 in another embodiment of the present invention. In the embodiment of FIG. 10, expandable member 512 includes a plurality of generally longitudinal undulating elements 524 with adjacent undulating elements being out-of-phase with one another and connected in a manner to form a plurality of diagonally disposed cell structures 526. The expandable member 512 includes a cylindrical portion 516 and a distal end portion 518 with the cell structures 526 in the main body portion 516 extending continuously and circumferentially around a longitudinal axis 530 of the expandable member 512. The cell structures 526 in the distal end portion 518 extend less than circumferentially around the longitudinal axis 530 of the expandable member 512. Attached to or otherwise coupled to each of the proximal-most cell structures 528 are proximally extending elongate flexible wires 540. The use of multiple elongate flexible wires 540 enables the pushing force applied to the proximal end of the expandable member 512 to be more evenly distributed about its proximal circumference. In another embodiment, although not shown in FIG. 10, the proximal-most strut elements 528 have a width and/or thickness greater than the struts in the other portions of the expandable member 512. Such a feature further contributes to the push force being evenly distributed about the circumference of the expandable member 512 and also inhibits the strut elements directly receiving the push force from buckling.

Figure 11A:
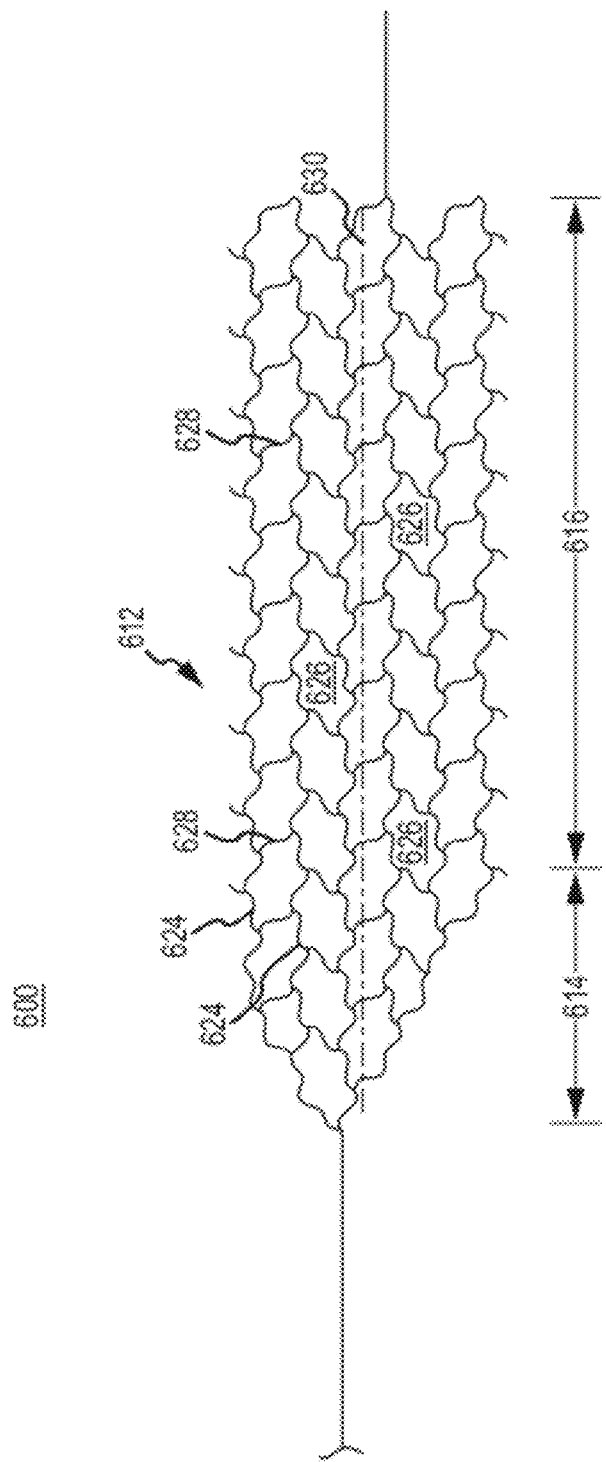
FIG. 11A illustrates a two-dimensional plane view of an expandable member of a treatment device in one implementation.
Figure 11B:
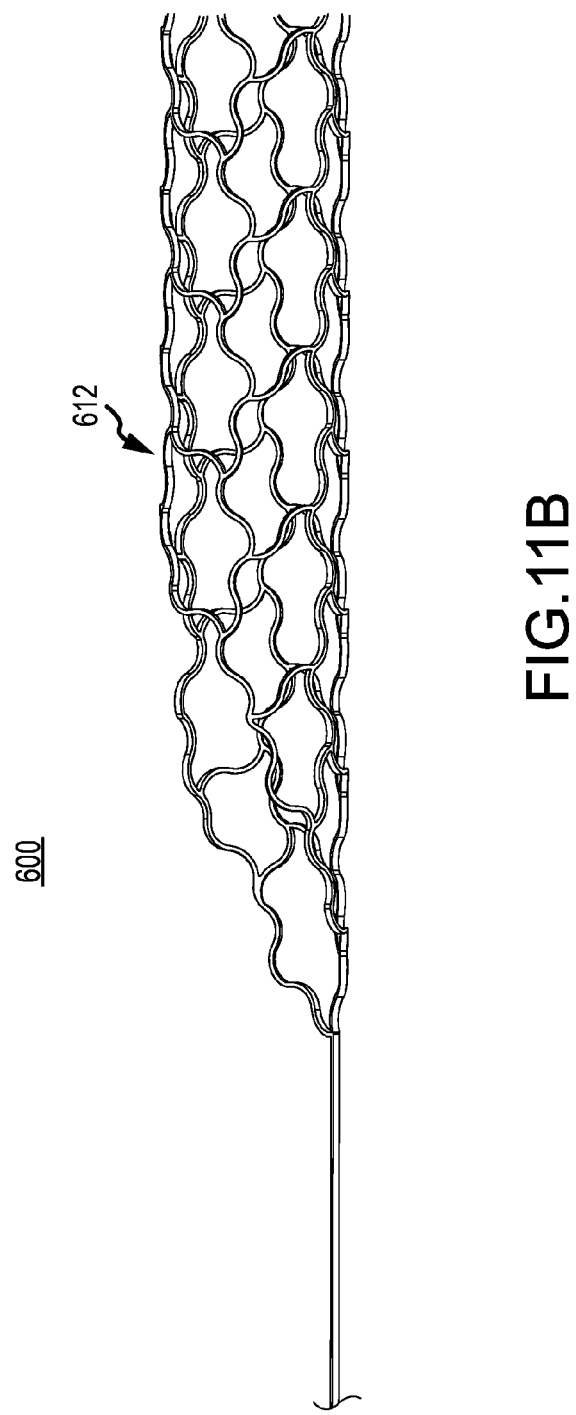
FIG. 11B is an isometric view of the expandable member illustrated in FIG. 11A.

FIGS. 11A and 11B illustrate a vascular treatment device 600 in accordance with another embodiment of the present invention. FIG. 11A depicts device 600 in a two-dimensional plane view as if the device were cut and laid flat on a surface. FIG. 11B depicts the device in its manufactured and/or expanded tubular configuration. In the embodiment of FIGS. 11A and 11B, expandable member 612 includes a plurality of generally longitudinal undulating elements 624 with adjacent undulating elements being interconnected by a plurality of curved connectors 628 to form a plurality of closed-cell structures 626 disposed about the length of the expandable member 612. In the embodiment shown, the expandable member 612 includes a proximal end portion 614 and a cylindrical portion 616 with the cell structures 626 in the cylindrical portion 616 extending continuously and circumferentially around a longitudinal axis 630 of the expandable member 612. The cell structures 626 in the proximal end portion 614 extend less than circumferentially around the longitudinal axis 630 of the expandable member 612. In an alternative embodiment, the expandable member 612 includes a proximal end portion, a cylindrical main body portion and a distal end portion, much like the expandable member 12 depicted in FIGS. 1A and 1B. In such an embodiment, the cell structures 626 in the distal end portion of the expandable member would extend less than circumferentially around the longitudinal axis 630 of the expandable member 612 in a manner similar to the proximal end portion 614 shown in FIG. 11A. Moreover, it is appreciated that the expandable members of FIGS. 1A, 4A, 6A, 7A, 7C, 10, 14, 15 and 19-24 may be modified in a way so as to eliminate the distal end portion (e.g., distal end portion 18 in FIG. 1A) so that there exists only a proximal end portion and main body portion like that of FIG. 11A.

Figure 12:
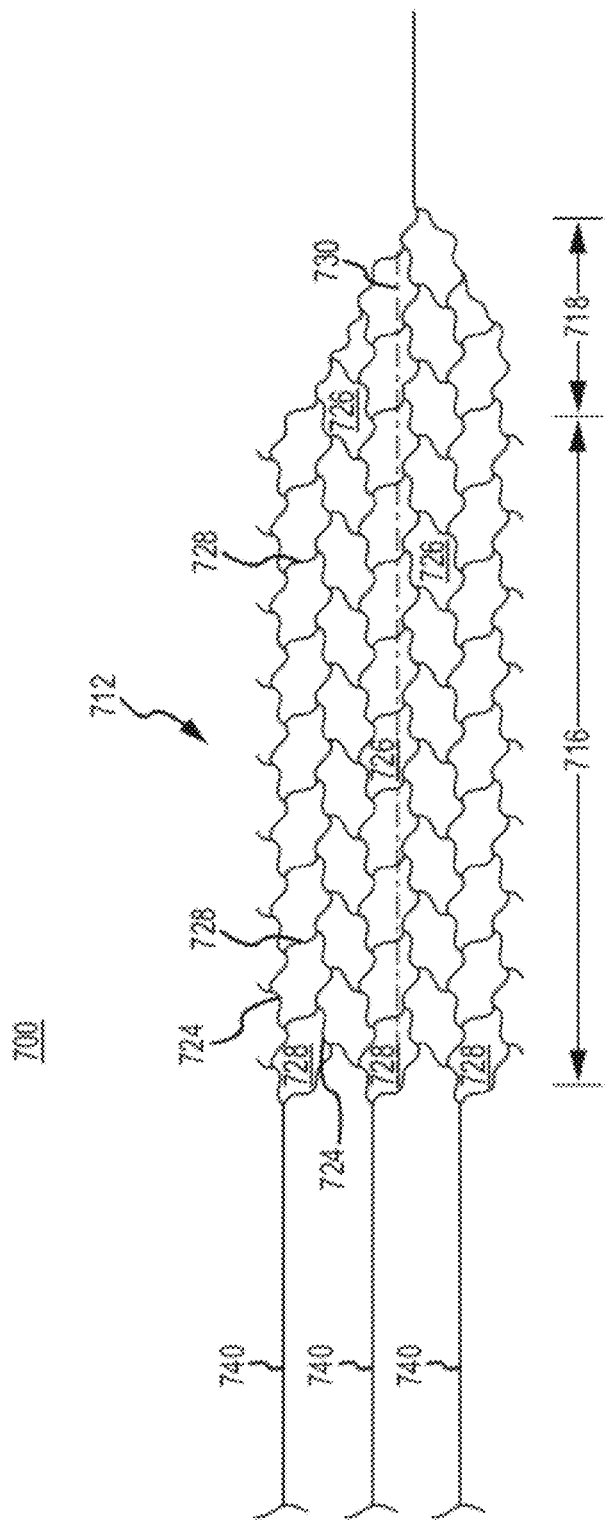
FIG. 12 illustrates a two-dimensional plane view of an expandable member of a treatment device in another implementation.

FIG. 12 illustrates a vascular treatment device 700 in accordance with another embodiment of the present invention. FIG. 12 depicts device 700 in a two-dimensional plane view as if the device were cut and laid flat on a surface. In the embodiment of FIG. 12, expandable member 712 includes a plurality of generally longitudinal undulating elements 724 with adjacent undulating elements being interconnected by a plurality of curved connectors 728 to form a plurality of closed-cell structures 726 disposed about the length of the expandable member 712. In the embodiment shown, the expandable member 712 includes a cylindrical portion 716 and a distal end portion 718 with the cell structures 726 in the cylindrical portion 716 extending continuously and circumferentially around a longitudinal axis 730 of the expandable member 712. The cell structures 726 in the distal end portion 718 extend less than circumferentially around the longitudinal axis 730 of the expandable member 712. In a manner similar to that described in conjunction with the embodiment of FIG. 10, attached to or otherwise coupled to each of the proximal-most cell structures 728 are proximally extending elongate flexible wires 740. This arrangement enables the pushing force applied to the proximal end of the expandable member 712 to be more evenly distributed about its proximal circumference. In another embodiment, although not shown in FIG. 12, the proximal-most strut elements 730 have a width and/or thickness greater than the struts in the other portions of the expandable member 712. Such a feature further contributes to the push force being evenly distributed about the circumference of the expandable member 712 and also inhibits the strut elements directly receiving the push force from buckling.

Figure 13A:
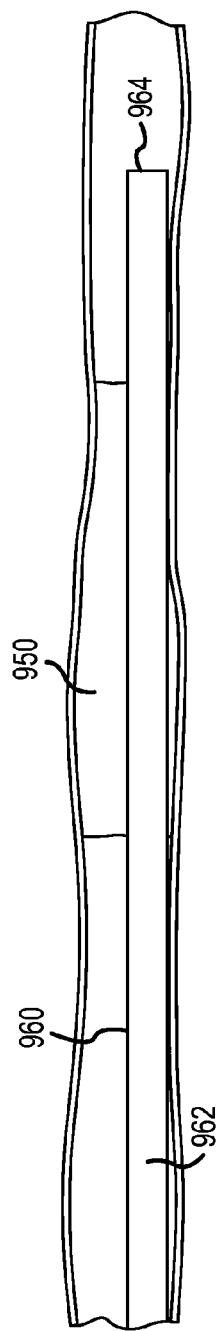
Figure 13B:
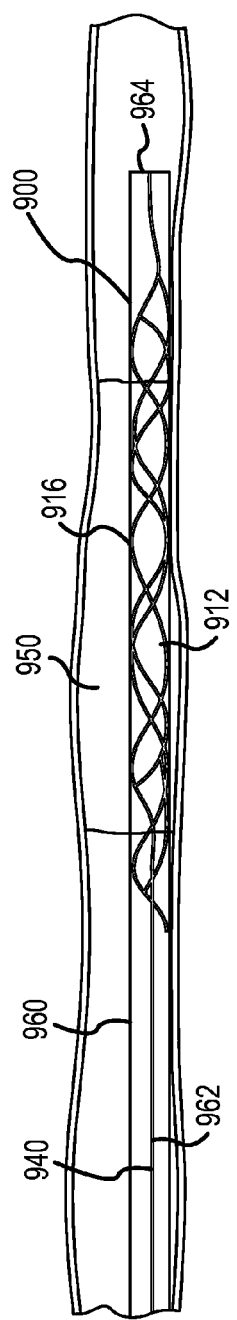

As previously discussed, in use, the expandable members of the present invention are advanced through the tortuous vascular anatomy of a patient to a treatment site, such as an embolic obstruction, in an unexpanded or compressed state of a first nominal diameter and are movable from the unexpanded state to a radially expanded state of a second nominal diameter greater than the first nominal diameter for deployment at the treatment site. One manner of delivering and deploying expandable member 912 at the site of an embolic obstruction 950 is shown in FIGS. 13A through 13C. As shown in FIG. 13A, a delivery catheter 960 having an inner lumen 962 is advanced to the site of the embolic obstruction 950 so that its distal end 964 is positioned distal to the obstruction. After the delivery catheter 960 is in position at the embolic obstruction 950, the retrieval device 900 is placed into the delivery catheter by introducing the expandable member 912 into a proximal end of the delivery catheter (not shown) and then advancing the expandable member 912 through the lumen 962 of the delivery catheter by applying a pushing force to elongate flexible wire 940. By the use of radiopaque markings and/or coatings positioned on the delivery catheter 960 and device 900, the expandable member 912 is positioned at the distal end of the delivery catheter 960 as shown in FIG. 13B so that the main body portion 916 is longitudinally aligned with the obstruction 950. Deployment of the expandable member 912 is achieved by proximally withdrawing the delivery catheter 960 while holding the expandable member 912 in a fixed position as shown in FIG. 13C. Once the expandable member 912 has been deployed to an expanded position within the obstruction 950, the expandable member 912 is retracted, along with the delivery catheter 960, to a position outside the patient. In one embodiment, the expandable member 912 is first partially retracted to engage with the distal end 964 of the delivery catheter 960 prior to fully retracting the devices from the patient.

In one embodiment, once the expandable member 912 is expanded at the obstruction 950, it is left to dwell there for a period of time in order to create a perfusion channel through the obstruction that causes the obstruction to be lysed by the resultant blood flow passing through the obstruction. In such an embodiment, it is not necessary that the expandable member 912 capture a portion of the obstruction 950 for retrieval outside the patient. When a sufficient portion of the obstruction 950 has been lysed to create a desired flow channel through the obstruction, or outright removal of the obstruction is achieved by the resultant blood flow, the expandable member 912 may be withdrawn into the delivery catheter 960 and subsequently removed from the patient.

In another embodiment, the expandable member 912 is expanded at the obstruction 950 and left to dwell there for a period of time in order to create a perfusion channel through the obstruction that causes the obstruction to be acted on by the resultant flow in a manner that makes the embolic obstruction more easily capturable by the expandable member and/or to make it more easily removable from the vessel wall of the patient. For example, the blood flow created through the embolic obstruction may be made to flow through the obstruction for a period of time sufficient to change the morphology of the obstruction that makes it more easily captured by the expandable member and/or makes it more easily detachable from the vessel wall. As in the preceding method, the creation of blood flow across the obstruction 950 also acts to preserve tissue. In one embodiment, the blood flow through the obstruction may be used to lyse the obstruction. However, in this modified method, lysing of the obstruction is performed for the purpose of preparing the obstruction to be more easily captured by the expandable member 912. When the obstruction 950 has been properly prepared, for example by creating an obstruction 950 of a desired nominal inner diameter, the expandable member 912 is deployed from the distal end 964 of the delivery catheter 940 to cause it to engage with the obstruction. Removal of all, or a portion, of the obstruction 950 from the patient is then carried out in a manner similar to that described above.

In yet another embodiment, once the expandable member 912 has been delivered and expanded inside the obstruction 950, it may be detached from the elongate wire 940 for permanent placement within the patient. In such an embodiment, the manner in which the elongate wire 940 is attached to the expandable member 912 allows the two components to be detached from one another. This may be achieved, for example, by the use of a mechanical interlock or an erodable electrolytic junction between the expandable member 912 and the elongate wire 940.

As described herein, the expandable members of the various embodiments may or may not include distal wire segments that are attached to their distal ends. In alternative preferred embodiments, vascular treatment devices that are configured to permanently place an expandable member at the site of an embolic obstruction do not include distal wire segments attached to the distal ends of the expandable members.

One advantage associated with the expandable member cell patterns of the present invention is that withdrawing the expandable members by the application of a pulling force on the proximal elongate wire flexible wire urges the expandable members to assume a smaller expanded diameter while being withdrawn from the patient, thus decreasing the likelihood of injury to the vessel wall. Also, during clot retrieval as the profile of the expandable members decrease, the cell structures collapse and pinch down on the clot to increase clot retrieval efficacy. Another advantage is that the cell patterns permit the expandable members to be retracted into the lumen of the delivery catheter after they have been partially or fully deployed. As such, if at any given time it is determined that the expandable member has been partially or fully deployed at an improper location, it may be retracted into the distal end of the delivery catheter and repositioned to the correct location.

Figure 14:
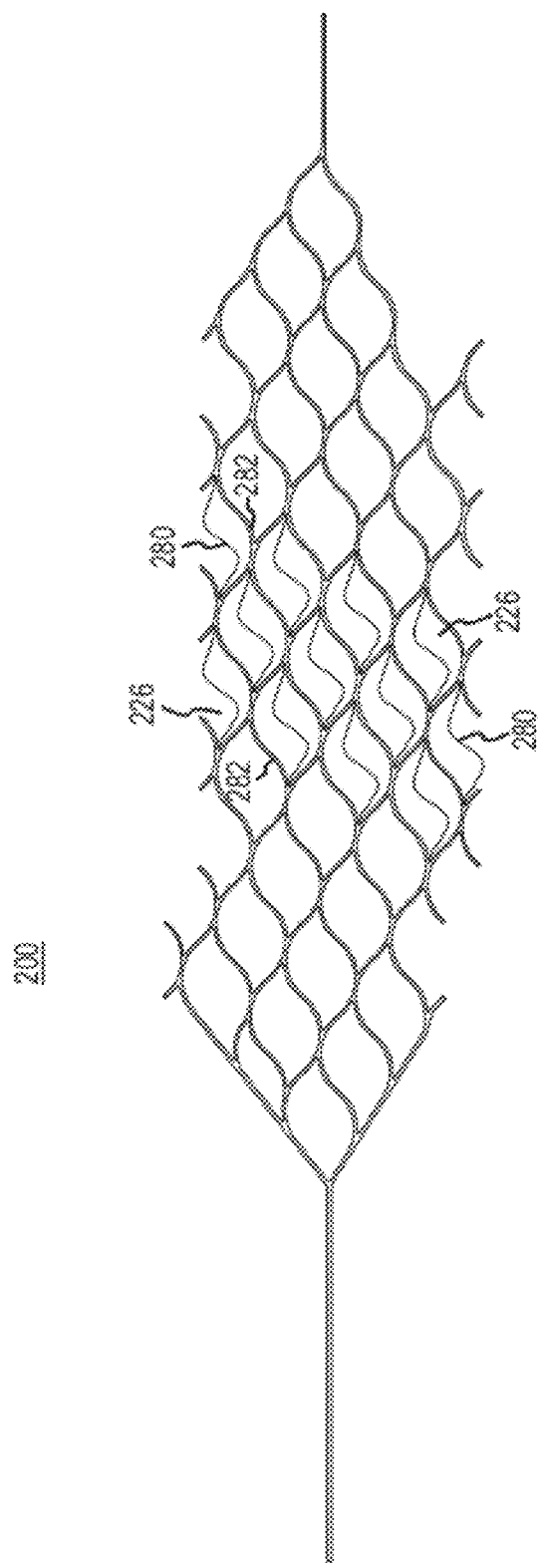
FIG. 14 illustrates a two-dimensional plane view of an expandable member of a treatment device in another embodiment.

With reference to FIG. 14, a modified version of the vascular treatment device 200 of FIG. 6A is shown that includes thin strut elements 280 intersecting at least some of the cell structures 226 located in the cylindrical main body portion 216 of expandable member 212. The thin strut elements 280 are dimensioned to have a width of less than the strut elements 282 that form the cell structures 226. In alternative exemplary embodiments, strut elements 280 have an as-cut or polished width dimension that is between about 25% to about 50% smaller than the respective as-cut or polished width dimension of struts 262. When used for the purpose of clot retrieval, a purpose of the thin struts 280 is to enhance the expandable member's ability to engage with and capture an embolic obstruction. This is accomplished by virtue of several factors.

Figure 15:
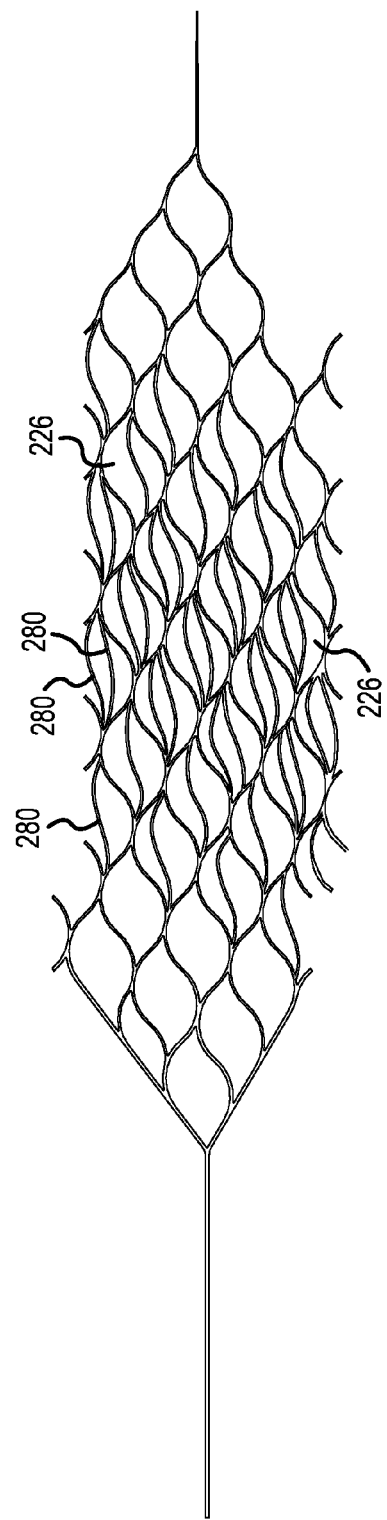
FIG. 15 illustrates a two-dimensional plane view of an expandable member of a treatment device in yet another embodiment.

First, the thinner width dimensions of the struts 280 make it easier for the struts to penetrate the obstruction. Second, they act to pinch portions of the entrapped obstruction against the outer and wider strut elements 282 as the expandable member is deployed within the obstruction. Third, they may be used to locally enhance radial forces acting on the obstruction. It is important to note that the use of thin strut elements 280 is not limited to use within cell structures 226 that reside within the cylindrical main body portion 216 of the expandable member 212. They may be strategically positioned in any or all of the cell structures of the expandable member. Moreover, it is important to note that the use of thin strut elements 280 is not limited to the embodiment of FIG. 6, but are applicable to all the various embodiments disclosed herein. Lastly, in alternative exemplary embodiments, as shown in FIG. 15, multiple thin strut elements 280 are provided within one or more of the cell structures 226, and may also be used in conjunction with cell structures that have a single thin strut element and/or cell structures altogether devoid of thin strut elements.

In the treatment of aneurysms when the treatment device is used for the purpose of diverting flow, the density of the cell structures 226 is sufficient to effectively divert flow away from the aneurysm sack. In alternative embodiments in lieu of, or in combination with adjusting the density of the cell structures 226, intermediate strut elements similar to the strut elements 280 of FIGS. 14 and 15 are used to increase the effective wall surface of the expandable member. In these embodiments, the intermediate strut elements may have the same, smaller, larger, or any combination thereof, dimensional characteristics of the cell structure struts. Conversely, in alternative embodiments for use in the treatment of aneurysms for the purpose placing coils or other like structures within the sack of the aneurysm, the size of the cell structures 226 is sufficient to facilitate passage of the coils through the cell structures.

Figure 16:
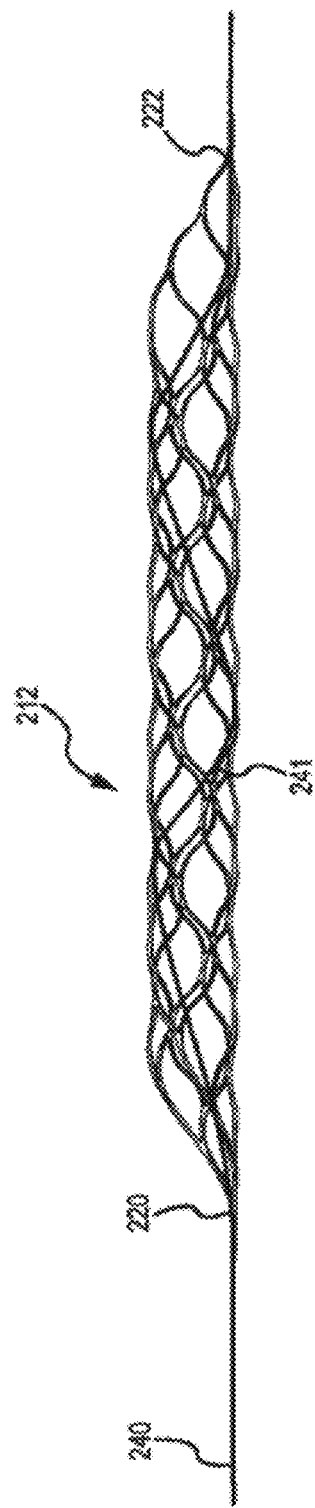
FIG. 16 illustrates an isometric view of an expandable member in another embodiment having an internal wire segment.

FIG. 16 illustrates a treatment device according to the embodiment of FIGS. 6A and 6B, wherein the pushability of the expandable member 212 during its advancement to the treatment site of a patient is enhanced by the inclusion of an internal wire segment 241 that extends between the proximal end 220 and distal end 222 of the expandable member 212. In this manner, the pushing force applied by elongate wire 240 is transmitted to both the proximal and distal ends of expandable device. The internal wire segment may be a discrete element that is attached to the proximal and distal ends of the expandable member, or may preferably be a co-extension of the elongate flexible wire 240. During delivery of the expandable member 212 to the treatment site in its compressed state, the internal wire segment 241 assumes a substantially straight or linear configuration so as to adequately distribute at least a part of the pushing force to the distal end 222 of the expandable member. When the expandable member 212 expands, it tends to foreshorten causing slack in the internal wire segment 241 that forms a long-pitched helix within the expandable member as shown in FIG. 16. An additional advantage associated with the use the internal wire segment 241 is that the formation of the internal helix upon expansion of the expandable member 212 assists in capturing the embolic obstruction.

Figure 17:
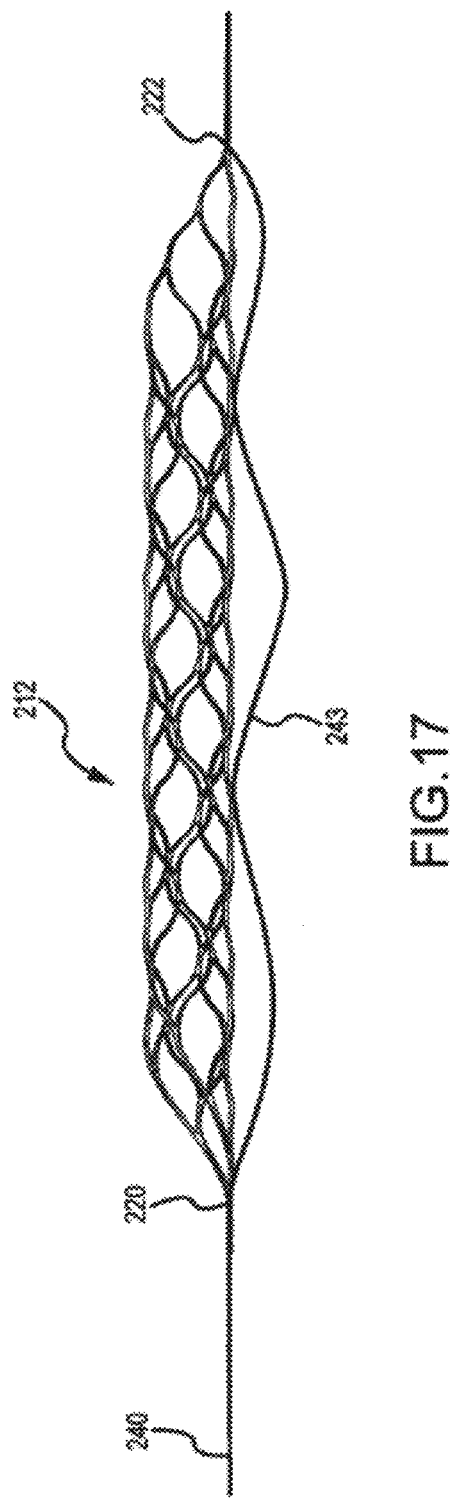
FIG. 17 illustrates an isometric view of an expandable member in another embodiment having an external wire segment.

In an alternative embodiment, as shown in FIG. 17, the pushability of the expandable member 212 during its advancement to the treatment site of a patient is enhanced by the inclusion of an external wire segment 243 that extend between the proximal end 220 and distal end 222 of the expandable member 212. In this manner, the pushing force applied by the elongate wire 240 is transmitted to both the proximal and distal ends of the expandable device. The external wire segment may be discrete element that is attached to the proximal and distal ends of the expandable member, or may preferably be a co-extension of the elongate flexible wire 240. During delivery of the expandable member 212 to the treatment site in its compressed state, the external wire segment 243 assumes a substantially straight or linear configuration so as to adequately distribute at least a part of the pushing force to the distal end 222 of the expandable member. When the expandable member 212 expands, it tends to foreshorten causing slack in the external wire segment 243 as shown in FIG. 17. An additional advantage associated with the use of the external wire segment 243 is that it directly acts on the obstruction while the expandable member 212 is expanded to assist in engaging and capturing the embolic obstruction.

Figure 18:
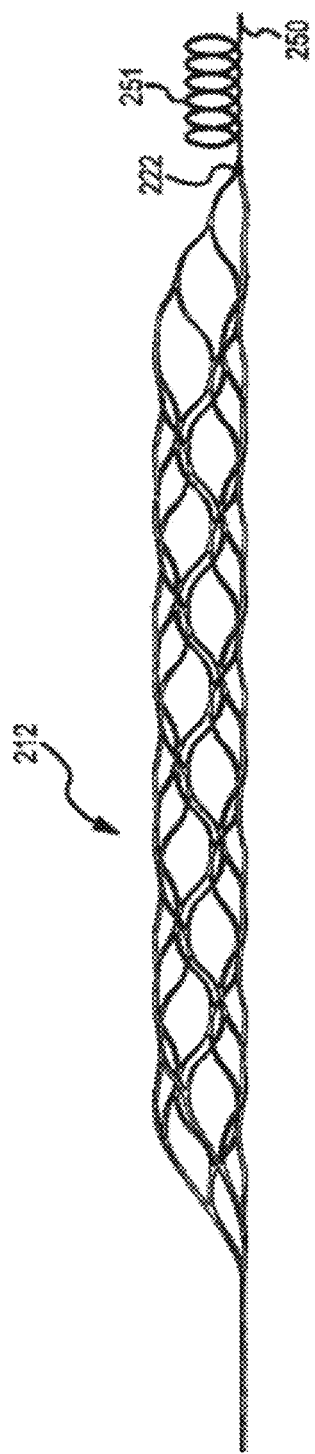
FIG. 18 illustrates an isometric view of an expandable member in yet another embodiment having a distal emboli capture device.

In yet another embodiment, a distal emboli capture device 251 is disposed on the distal wire segment 250, or otherwise attached to the distal end 222, of expandable member 212 as shown in FIG. 18. The function of the distal emboli capture device 251 is to capture emboli that may be dislodged from the embolic obstruction during the expansion of the expandable member 212 or during its removal from the patient to prevent distal embolization. In FIG. 18, the distal emboli capture device is shown as a coil. In alternative embodiments, baskets, embolic filters or other known emboli capture devices may be attached to the distal end 222 or distal wire segment 250 of expandable member 12.

Again, as with the embodiments of FIGS. 14 and 15, it is important to note that the features described in conjunction with FIGS. 16, 17 and 18 are not limited to the embodiment of FIG. 6, but are applicable to all the various embodiments disclosed herein.

Figure 19:
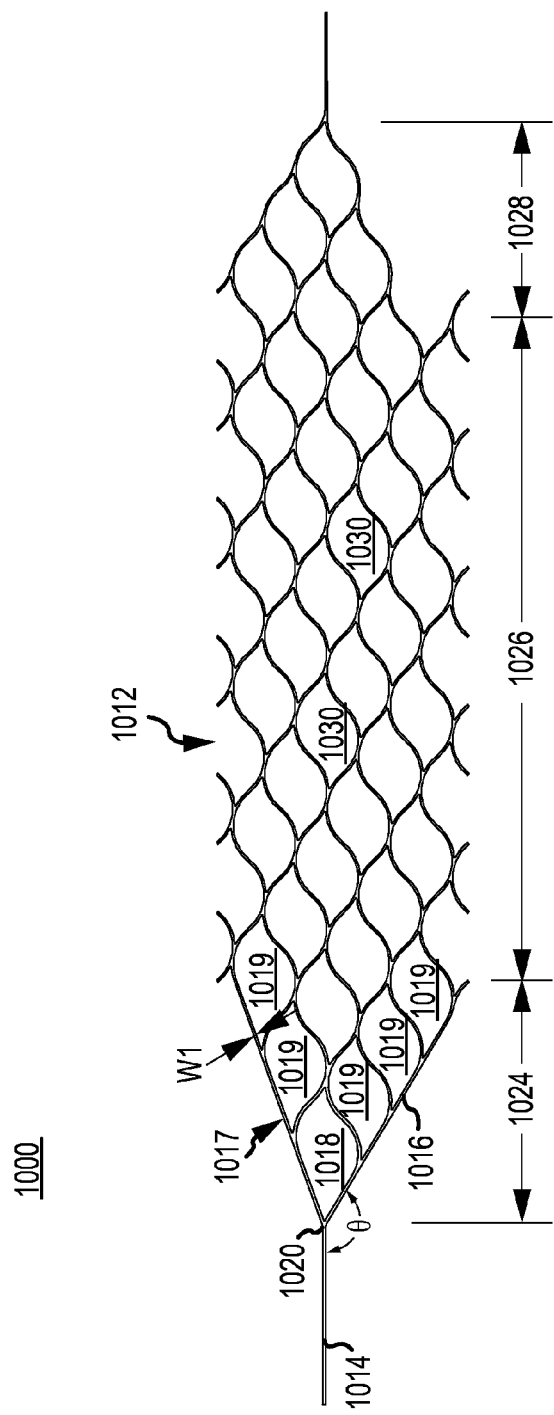
FIG. 19 illustrates a two-dimensional plane view of an expandable member of a treatment device in another embodiment.

FIG. 19 illustrates a bodily duct or vascular treatment device 1000 in accordance with another embodiment of the present invention. FIG. 19 depicts device 1000 in a two-dimensional plane view as if the device were cut and laid flat on a surface. Device 1000 includes an expandable member 1012 having a proximal end portion 1024, a cylindrical main body portion 1026 and a distal end portion 1028 with an elongate flexible wire 1014 attached to or otherwise coupled to the proximal end 1020 of the expandable member. The construction of device 1000 is similar to device 200 described above in conjunction with FIG. 6A except that the cell structures 1018 and 1019 in the proximal end portion 1024 are more closely symmetrically arranged than the cell structures in the proximal end portion 214 of device 200. The more substantial symmetrical arrangement of the cell structures in the proximal end portion 1024 of device 1000 facilitates the loading or retrieval of the expandable member 1012 into a lumen of a delivery catheter or sheath (not shown) by causing the proximal end portion 1024 to collapse more evenly during compression. The proximal wall segments 1016 of cell structures 1018 and 1019 comprise linear or substantially linear strut elements as viewed in the two dimension plane view of FIG. 19. In one embodiment, the linear strut elements 1016 are aligned to form continuous and substantially linear rail segments 1017 that extend from the proximal end 1020 of proximal end portion 1024 to a proximal-most end of main body portion 1026 (again, as viewed in the two dimension plane view of FIG. 19) and preferably are of the same length. In alternative embodiments, the angle θ between the wire segment 1014 and rail segments 1017 ranges between about 140 degrees to about 150 degrees. In one embodiment, one or both of the linear rail segments 1017 have a width dimension W1 which is greater than the width dimension of the adjacent strut segments of cell structures 1018 and/or 1019 and/or 1030. An enhanced width dimension W1 of one or both the linear rail segments 1017 further enhances the rail segments' ability to distribute forces and resist buckling when a push force is applied to them. In another implementation, one or both of the linear rail segments 1017 are provided with an enhanced thickness dimension, rather than an enhanced width dimension to achieve the same or similar result. In yet an alternative implementation, both the width and thickness dimensions of one or both of the linear rail segments 1017 are enhanced to achieve the same or similar results. In yet another implementation, the width and/or thickness dimensions of each of the rail segments 1017 differ in a manner that causes a more even compression of the proximal end portion 1024 of the expandable member 1012 when it is collapsed as it is loaded or retrieved into a delivery catheter or sheath.

Figure 20:
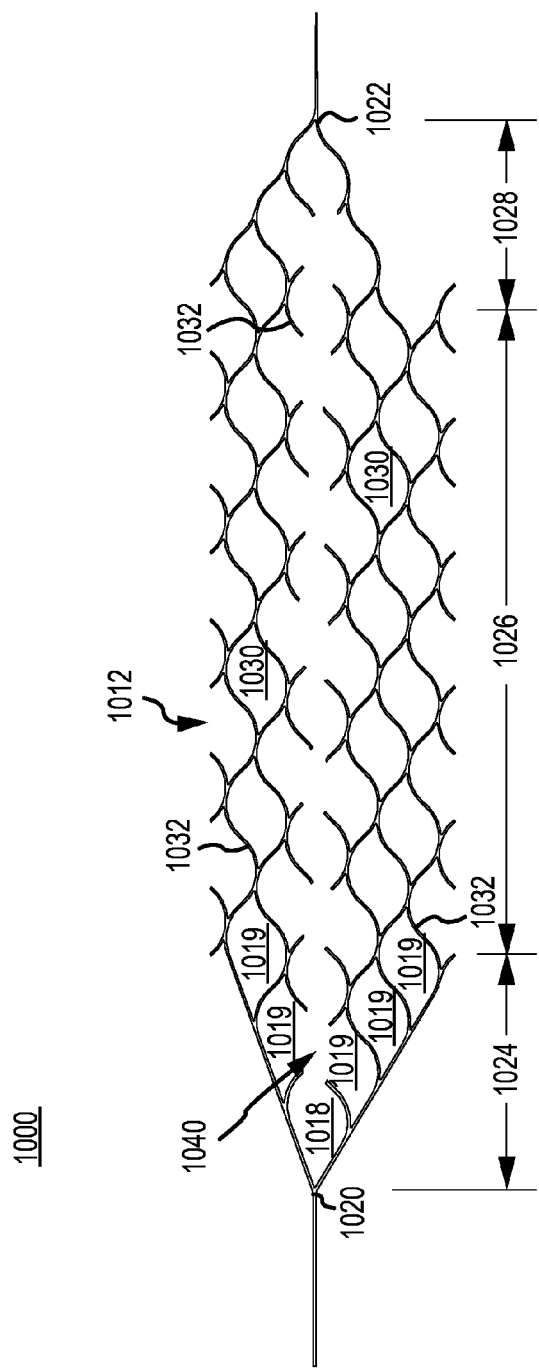
FIG. 20 illustrates the expandable member of FIG. 19 having a longitudinal slit.
Figure 21:
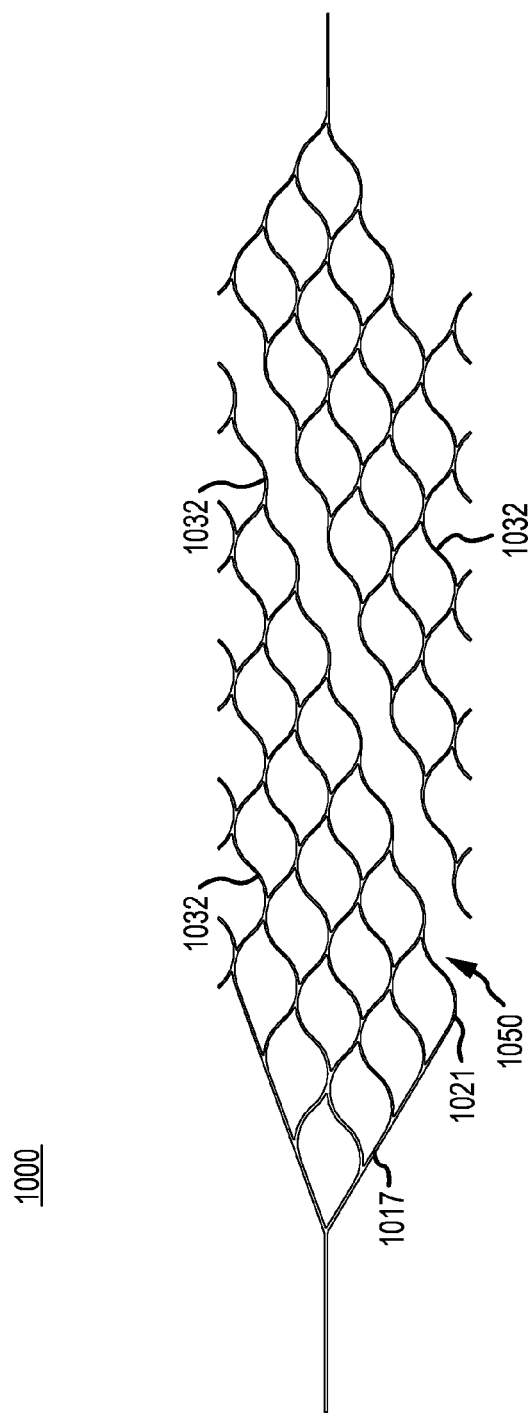
FIG. 21 illustrates the expandable member of FIG. 19 having a spiral slit.
Figure 22:
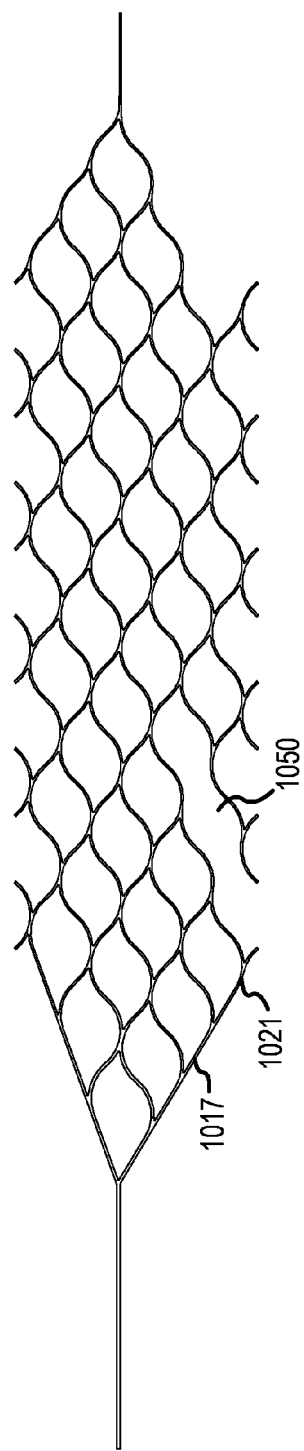
FIG. 22 illustrates the expandable member of FIG. 19 having a partial spiral slit.

Although the description that follows is directed to the embodiment of FIG. 19, it is important to note that the provision of a slit as contemplated by the embodiments of FIGS. 20-22 are applicable to all the vascular treatment devices described herein, and their numerous embodiments and modifications thereof.

Turning now to FIG. 20, the treatment device 1000 of FIG. 19 is depicted having a longitudinal slit 1040 that extends from the proximal end 1020 to the distal end 1022 of the expandable member 1012. The slit 1040 permits the cell structures 1018, 1019 and 1030 to move relative to one another in a manner that inhibits the individual strut elements 1032 of the expandable member 1012 from buckling during compression of the expandable member 1012 as it is loaded or retrieved into a delivery catheter or sheath. In alternative embodiments, slit 1040 extends less than the entire length of expandable member 1012 and is arranged to inhibit buckling of strategically important strut elements that most affect the expandable member's ability to be effectively loaded or withdrawn into a delivery catheter or sheath. For example, in one embodiment, slit 1040 is provided only in the proximal end portion 1024 of the expandable member 1012 where the likelihood of buckling or bending of struts 1032 is most likely to occur. In another embodiment, slit 1040 is provided in both the proximal end portion 1024 and the cylindrical main body portion 1026 of expandable member 1012.

FIG. 21 illustrates the treatment device 1000 of FIG. 19 having a diagonally disposed/spiral slit 1050 that extends the entire circumference of the expandable member 1012. In one embodiment, as illustrated in FIG. 21, the spiral slit 1050 originates at the distal position, or at a point adjacent to the distal position, of the proximal end portion 1024 of expandable member 1012. With respect to the embodiments having linear rail segments, such as the linear rail segments 1017 of FIG. 19, the spiral slit 1050 originates at the distal position 1021 of one of the linear rail segments 1017, or at a point distally adjacent to the distal position 1021, as shown in FIG. 21. Testing of the various vascular treatment devices described herein has shown that the occurrence of buckling tends to occur at the strut elements located adjacent to the distal positions of the proximal end portions of the expandable members. This phenomenon is exacerbated in the expandable members having proximal end portions with linear rail segments. For this reason, and with reference to FIG. 21, the originating point of spiral slit 1050 is located at or adjacent to a distal position 1021 of one of the linear rail segments 1017. An advantage of the diagonally disposed and/or spiral slit configuration of FIG. 21 is that it originates where the buckling tends to originate and further inhibits buckling of strut elements 1032 along the length of the expandable member 1012. As shown in FIG. 22, in alternative embodiments slit 1050 extends diagonally along only a portion of the circumference of the cylindrical main body portion 1026 of the expandable member 1012. In the embodiment of FIG. 22, slit 1050 originates at the distal position 1021 of linear rail segment 1017. In alternative embodiments, where buckling of individual strut elements 1032 originate at a point other than at the distal point of the proximal end portion 1024 of the expandable member 1012, the originating point of the slit 1050 is located at the origination point of the bucking (absent the slit 1050) and extends in a longitudinal direction distally therefrom.

Figure 23:
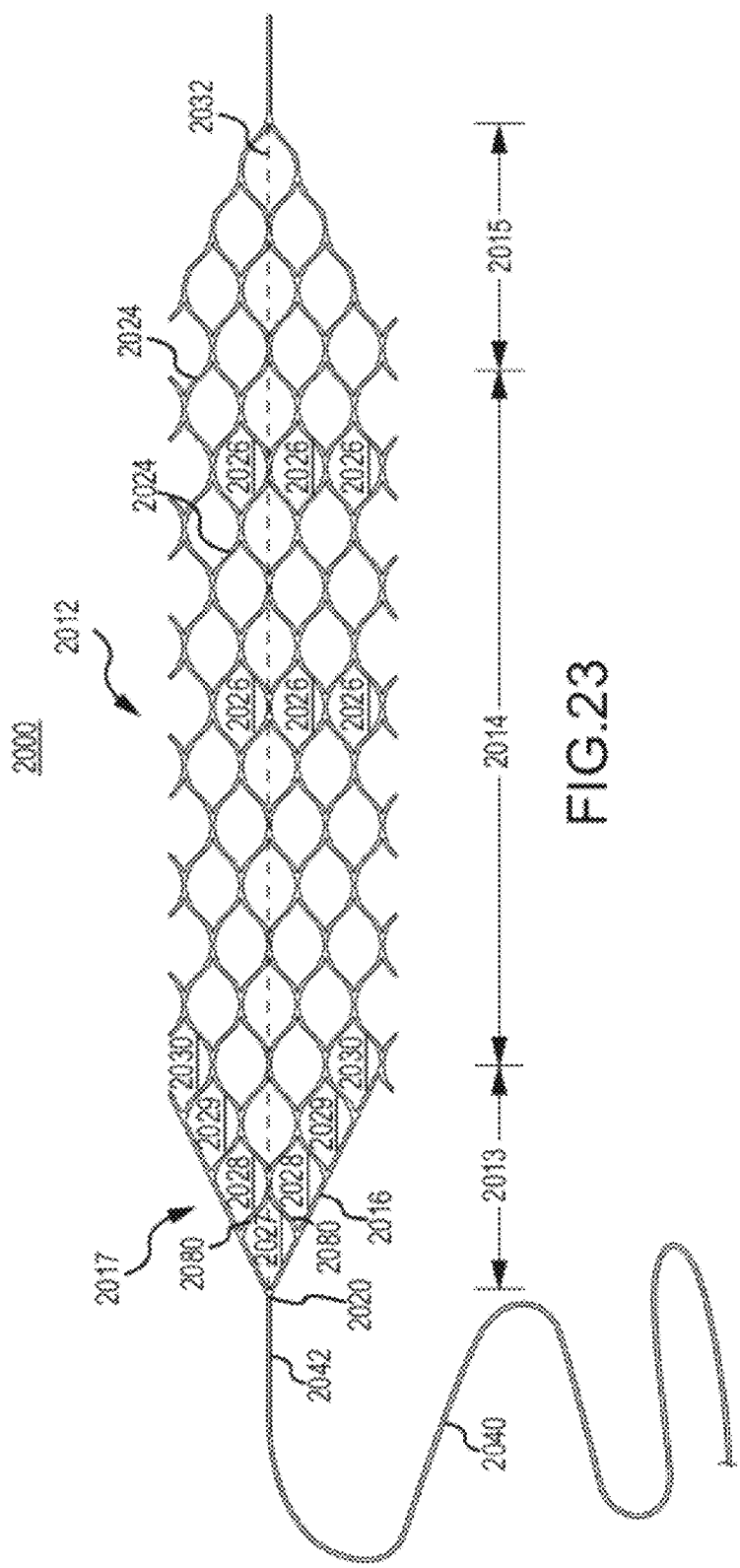
FIG. 23 illustrates a two-dimensional plane view of an expandable member of a treatment device in another embodiment.

FIG. 23 illustrates a bodily duct or vascular treatment device 2000 in accordance with an embodiment of the present invention. FIG. 23 depicts device 2000 in a two-dimensional plane view as if the device were cut and laid flat on a surface. Device 2000 includes a self-expandable member 2012 that is attached or otherwise coupled to an elongate flexible wire 2040 that extends proximally from the expandable member 2012. In one embodiment, the expandable member 2012 is made of shape memory material, such as Nitinol, and is preferably laser cut from a tube. In one embodiment, the expandable member 2012 has an integrally formed proximally extending wire segment 2042 that is used to join the elongate flexible wire 2040 to the expandable member 2012. In such an embodiment, flexible wire 2040 may be joined to wire segment 2042 by the use of solder, a weld, an adhesive, or other known attachment method. In an alternative embodiment, the distal end of flexible wire 2040 is attached directly to a proximal end 2020 of the expandable member 2012.

In the embodiment of FIG. 23, expandable member 2012 includes a plurality of generally longitudinal undulating elements 2024 with adjacent undulating elements being coupled to one another in a manner to form a plurality of circumferentially-aligned cell structures 2026. The expandable member 2012 includes a proximal end portion 2013, a cylindrical main body portion 2014 and a distal end portion 2015 with the cell structures 2026 in the main body portion 2014 extending continuously and circumferentially around a longitudinal axis 2032 of the expandable member 2012. The cell structures in the proximal end portion 2013 and distal end portion 2015 extend less than circumferentially around the longitudinal axis 2032 of the expandable member 2012. The proximal wall segments 2016 of cell structures 2027, 2028, 2029 and 2030 comprise linear or substantially linear strut elements as viewed in the two dimension plane view of FIG. 23. In one embodiment, the linear strut elements 2016 are aligned to form continuous and substantially linear rail segments 2017 that extend from the proximal end 2020 of proximal end portion 2013 to a proximal-most end of main body portion 2014 (again, as viewed in the two dimension plane view of FIG. 23) and preferably are of the same length. As described above in conjunction with FIGS. 6A and 6B, rail segments 2017 are not in fact linear but are of a curved and non-undulating shape. This configuration advantageously provides rail segments 2017 devoid of undulations thereby enhancing the rail segments' ability to distribute forces and resist buckling when a push force is applied to them. In alternative preferred embodiments, the angle θ between the wire segment 2042 or 2040, which ever the case may be, and rail segments 2017 ranges between about 140 degrees to about 150 degrees. In one embodiment the linear rail segments 2017 have a width dimension which is greater than the width dimension of the adjacent strut segments of cell structures 2027 and/or 2028 and/or 2029 and/or 2030 and/or 2026. An enhanced width of the linear rail segments 2017 further enhances the rail segments' ability to distribute forces and resist buckling when a push force is applied to the expandable member. In another implementation the linear rail segments 2017 are provided with an enhanced thickness dimension, rather than an enhanced width dimension to achieve the same or similar result. In yet an alternative implementation, both the width and thickness dimensions of the linear rail segments 2017 are enhanced to achieve the same or similar results.

In one embodiment, the width and/or thickness of the internal strut elements 2080 of proximal-most cell structure 2027 is also enhanced so as to resist buckling of these elements while the expandable member is being pushed through a sheath or delivery catheter. In one exemplary embodiment, the "as-cut" nominal widths of the enhanced strut elements 2016 and 2080 are about 0.0045 inches, while the "as-cut" nominal width of the other strut elements are about 0.003 inches.

Figure 24A:
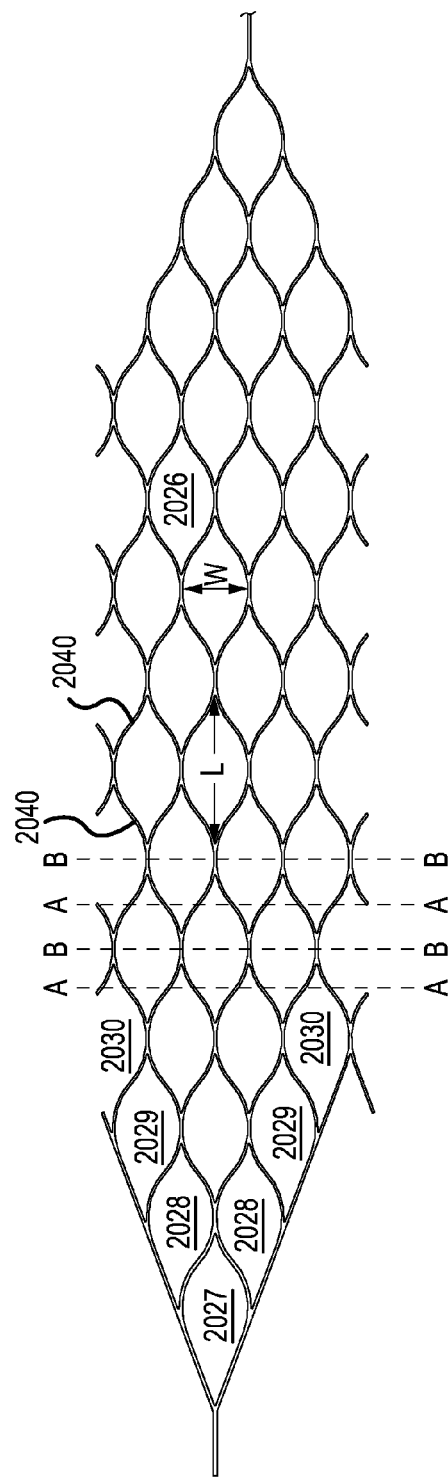
FIG. 24A illustrates a two-dimensional plane view of an expandable member of a treatment device in yet another embodiment.
Figure 24B:
FIG. 24B is an isometric view of the expandable member illustrated in FIG. 24A.

FIGS. 24A and 24B illustrate a vascular treatment device 3000 of another embodiment of the present invention. FIG. 24A depicts device 3000 in a two-dimensional plane view as if the device were cut and laid flat on a surface. FIG. 24B depicts the device in its manufactured and/or expanded tubular configuration. The overall design of device 3000 is similar to the design of device 2000 depicted and described above in reference to FIG. 23. The primary difference between the two designs lays in the length "L" to width "W" ratio of the cell structures 2026, 2027, 2028, 2029 and 2030. The length to width ratios of the cells structures of FIG. 24A are generally greater than the length to width ratios of the respective cell structures of FIG. 23. As illustrated, the lengths "L" of the cell structures of the device of FIG. 24A, in the "as-cut" configuration are generally greater than the lengths of the respective cell structures of FIG. 23, while the widths "W" of the cell structures of the device of FIG. 24A are generally smaller than the width of the respective cell structures of FIG. 23. As a result, the slope of the individual strut elements 2040 in the cell structures of FIG. 24A are generally smaller than the slopes of the respective strut elements in the cell structures of FIG. 23. By reducing the slope of the strut elements 2040 and leaving the other dimensional and material characteristics constant, the effective radial force along the length of the struts 2040 is reduced. The effect of such a reduction is that the summation of axial force components along lines A-A of the device of FIG. 24 more closely matches the summation of the radial force components along lines B-B as compared to the device of FIG. 23. Through experimentation, the inventors have discovered that an "as-cut" cell structure length to width ratio of greater than about 2.0, and an "expanded" cell structure length to width ratio of a greater than about 1.25, advantageously resulted in a longitudinal radial force distribution along the length of the expandable member 2012 that enhanced the expandable member's ability to be pushed through and withdrawn into a lumen of a delivery catheter.

Figure 26:
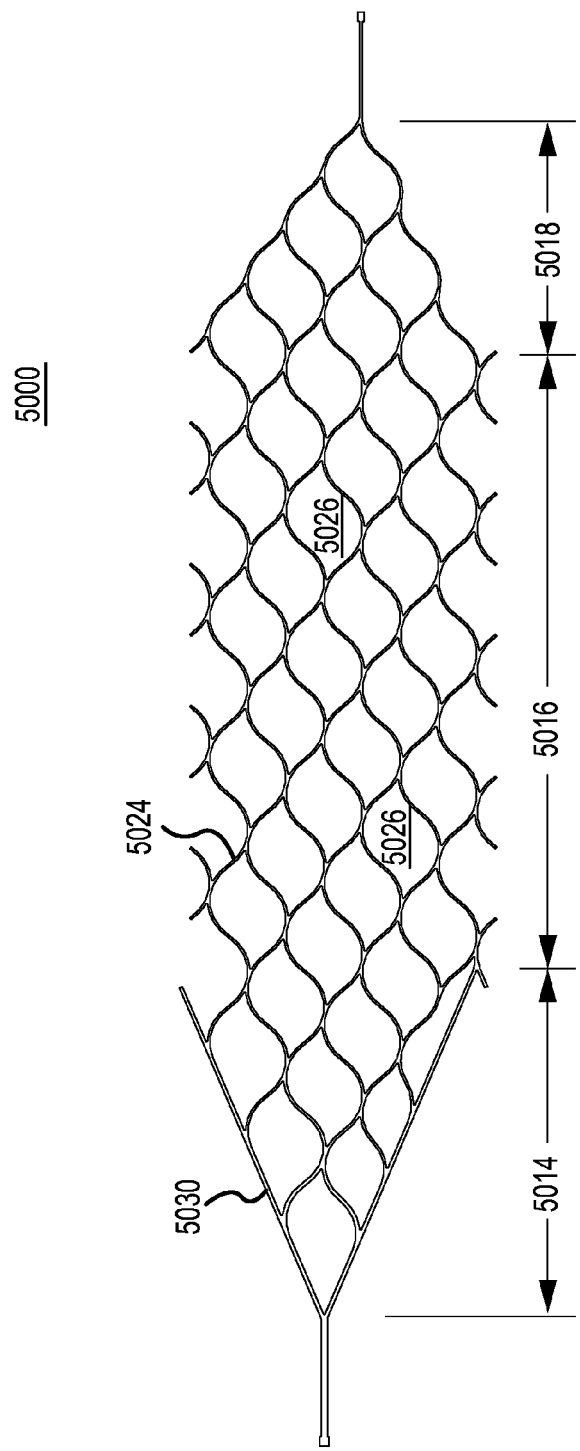
FIG. 26 illustrates a two-dimensional plane view of an expandable member of a treatment device in yet another embodiment.
Figure 27A:
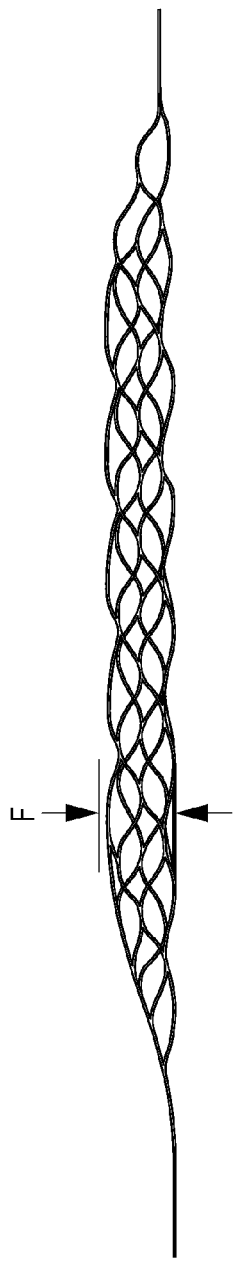
FIGS. 27A and 27B illustrate isometric side and top views, respectively, of the expandable member depicted in FIG. 26.
Figure 27B:
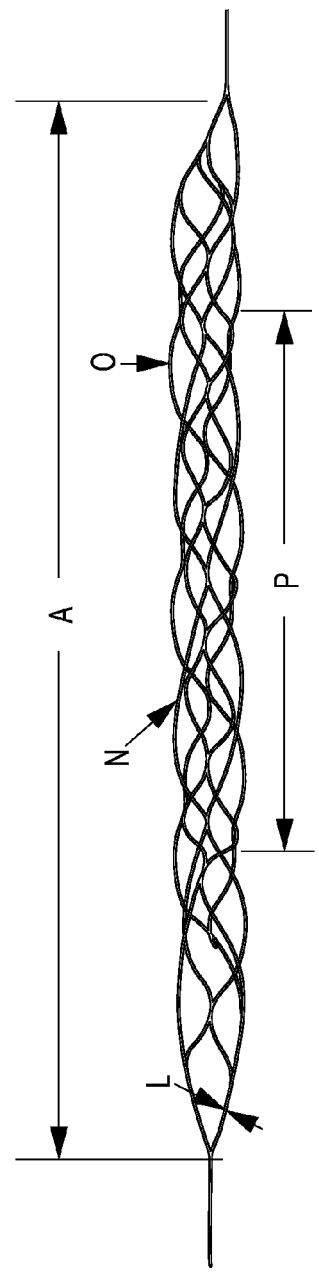

FIGS. 26, 27A and 27B illustrate an expandable member 5000 in another implementation. Expandable member 5000 includes a plurality of generally longitudinal undulating elements 5024 with adjacent undulating elements being out-of-phase with one another and connected in a manner to form a plurality of diagonally disposed cell structures 5026 angularly disposed between about 40.0 to about 50.0 degrees with respect to one another. In one implementation, the cell structures are diagonally displaced along about a 45.0 degree line. The expandable member 5000 includes a proximal end portion 5014, a cylindrical main body portion 5016 and a distal end portion 5018 with the cell structures 5026 in the main body portion 5016 extending continuously and circumferentially around a longitudinal axis of the expandable member 5000. The cell structures 5026 in the proximal end portion 5014 and distal end portion 5018 extend less than circumferentially around the longitudinal axis of the expandable member 5000. In one implementation, the expandable member has an unexpanded or crimped nominal diameter of about 1.0 millimeters and a designed maximum implantable diameter of about 4.0 millimeters.

In one embodiment, expandable member 5000 has an overall length dimension A of about 36.0±2.0 millimeters with the main body portion 5016 having a length P of about 19.0±2.0 millimeters. In one implementation the strut width dimension N and thickness dimension O within the main body portion 5016 are about 0.0021±0.0004 inches and about 0.0032±0.0005 inches, respectively, while the strut width dimension L of the proximal rails 5030 is about 0.0039±0.004 inches.

In use, expandable member 5000 is advanced through the tortuous vascular anatomy or bodily duct of a patient to a treatment site in an unexpanded or compressed state (not shown) of a first nominal diameter and is movable from the unexpanded state to a radially expanded state of a second nominal diameter greater than the first nominal diameter for deployment at the treatment site. In alternative exemplary embodiments the first nominal diameter (e.g., average diameter of main body portion 5016) ranges between about 0.017 to about 0.030 inches, whereas the second nominal diameter (e.g., average diameter of main body portion 5016) is between about 2.5 to about 5.0 millimeters. In one implementation, the dimensional and material characteristics of the cell structures 5026 residing in the main body portion 5016 of the expandable material 5000 are selected to produce sufficient radial force and contact interaction to cause the cell structures 5026 to engage with an embolic obstruction residing in the vascular in a manner that permits partial or full removal of the embolic obstruction from the patient. In other embodiments the dimensional and material characteristics of the cell structures 5026 in the main body portion 5016 are selected to produce a radial force per unit length of between about 0.005 N/mm to about 0.050 N/mm, preferable between about 0.010 N/mm to about 0.050 N/mm, and more preferably between about 0.030 N/mm and about 0.050 N/mm. In one embodiment, the diameter of the main body portion 5016 in a designed fully expanded implanted state is about 4.0 millimeters with the cell pattern, strut dimensions and material being selected to produce a radial force of between about 0.030 N/mm to about 0.050 N/mm when the diameter of the main body portion is reduced to 1.5 millimeters. In the same or alternative embodiment, the cell pattern, strut dimensions and material(s) are selected to produce a radial force of between about 0.010 N/mm to about 0.020 N/mm when the diameter of the main body portion is reduced to 3.0 millimeters.

Figure 29:
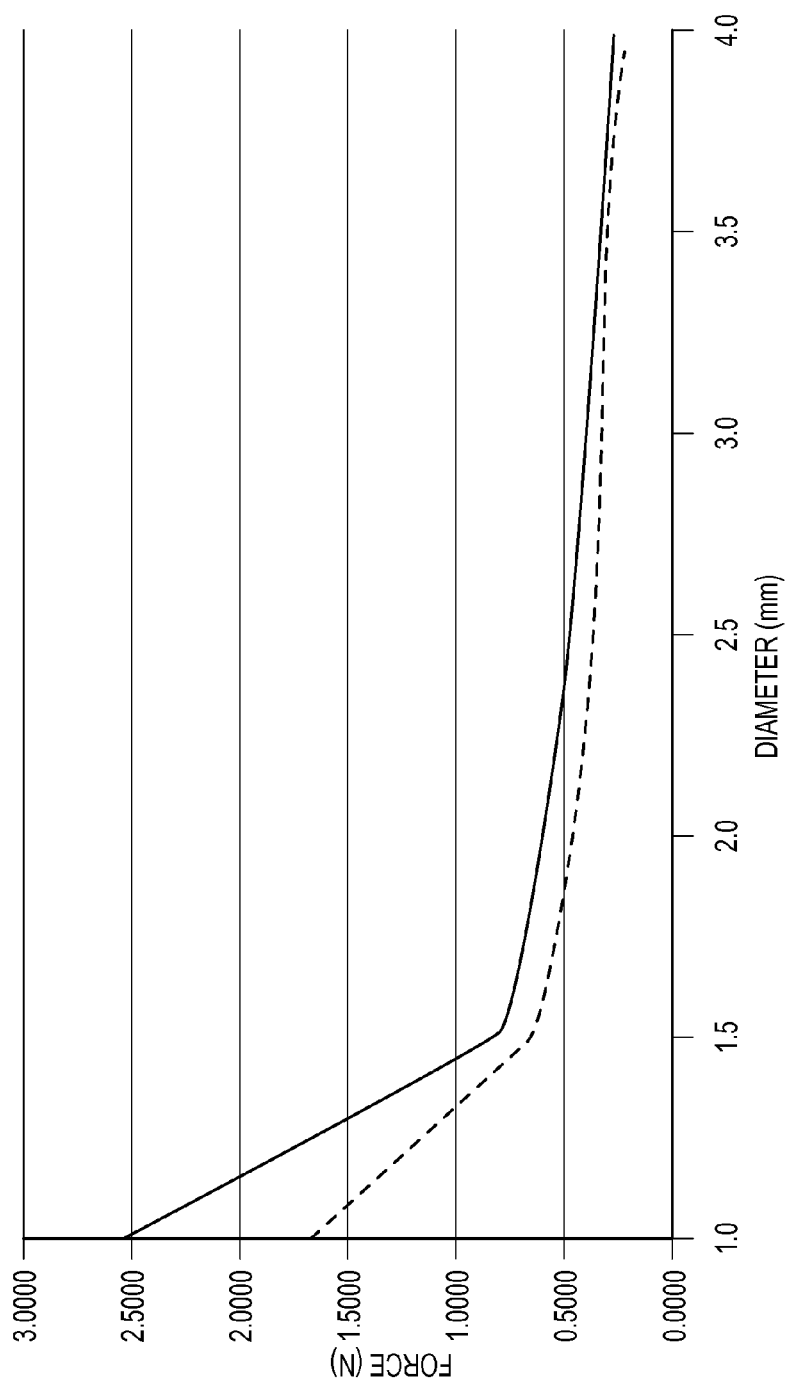
FIG. 29 is a graph representing a radial force curve of an expandable member according to one implementation.

In one implementation, as shown in the graph of FIG. 29, the cell structures are constructed to have dimensional and material characteristics to create an overall radial force exerted along the length of the expandable member 5000 of between about 1.7N and about 2.50N when the expandable member 5000 is in the compressed or crimped state. About a −1.0N to a about a −1.7N overall reduction in radial force along the length of the expandable member occurs during about an initial 0.50 mm diametric range of expansion from the compressed or crimped state. In a subsequent 0.5 mm diametric range of expansion that follows the initial 0.5 mm of expansion, about a −0.18N to about a −0.19N overall reduction in radial force along the length of the expandable member occurs. Advantageously, the expandable member 5000 exerts a relatively high radial force during its initial expansion to enhance the likelihood that the struts of expandable member engage an obstruction within the duct of a patient upon initial deployment of the device. In addition, the rate at which the radial force diminishes is initially much greater during the initial expansion of the device than during subsequent expansion. In the exemplary embodiment depicted by FIG. 29, the initial rate of reduction in the radial force during about the first 0.5 mm of expansion is about 5.5 to 9.7 times greater than the rate of reduction during the subsequent 0.5 mm of expansion. An advantage of this radial force characteristic is that high radial force values can be achieved during initial deployment of the expandable member to enhance integration of the struts of the expandable member into the duct obstruction with a subsequent large reduction in radial force after the initial expansion, the large reduction facilitating or enhancing the ability of the obstruction to be removed from the duct of the patient without complications and with limited adverse interactions with the duct (e.g., less damage to the duct wall, etc.). Another advantage of the radial force characteristics depicted in FIG. 29 is that during subsequent expansions, the rate of decrease in the over radial force along the length of the expandable member decreases in a linear-like fashion at a much reduced rate providing a level of predictability of the radial force being exerted at the different expandable member diameters. Also, advantageously, the radial force exerted by the expandable member is designed to achieve a non-zero value when the expandable member is at a designed maximum implantable diameter.

Figure 30:
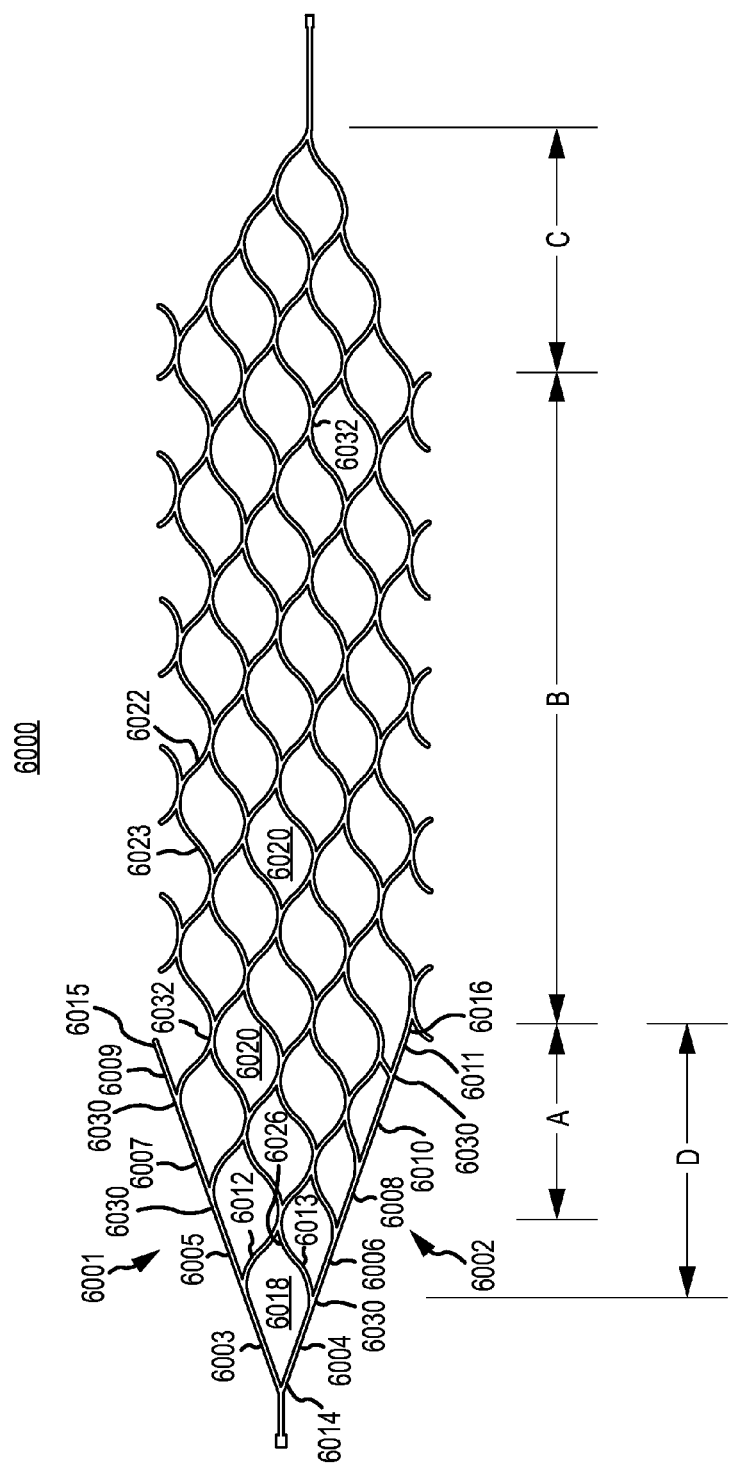
FIG. 30 illustrates a two-dimensional plane view of clot retrieval devices according some implementations.

FIG. 30 illustrates clot retrieval devices 6000 according to other implementations where, among other features, the strut elements of rail segments 6001 and 6002 have varying width dimensions. FIG. 30 depicts a clot retrieval device in a two-dimensional plane view as if the device were cut and laid flat on a surface. FIG. 30 depicts the device in its manufactured (as-cut) configuration. In one implementation, rail segment 6001 transitions from a maximum width dimension at or near its proximal end 6014 to a minimum width dimension at or near its distal end 6015. In a like manner, rail segment 6002 transitions from a maximum width dimension at or near its proximal end 6014 to a minimum width dimension at or near its distal end 6016. As previously discussed, the width dimensions of the rail segments are selected to enhance their ability to distribute forces and to resist buckling when a push force is applied to the proximal end 6014 of the vascular treatment device. In some implementations the percentage change between the maximum rail width dimension and the minimum rail width dimension is between about 20.0% and about 50.0%. In other implementations the percentage change between the maximum rail width dimension and the minimum rail width dimension is between about 25.0% and about 45.0%. In other implementations the percentage change between the maximum rail width dimension and the minimum rail width dimension is between about 35.0% and about 45.0%. In an exemplary implementation the width dimension of the rail segments transitions from a maximum width dimension of about 0.0047±0.0004 inches to a minimum width dimension of about 0.0027±0.0004 inches. In another exemplary implementation the width dimension of the rail segments transitions from a maximum width dimension of about 0.0047±0.0004 inches to a minimum width dimension of about 0.0035±0.0004 inches. In another exemplary implementation the width dimension of the rail segments transitions from a maximum width dimension of about 0.0047±0.0004 inches to a minimum width dimension of about 0.0037±0.0004 inches. As discussed above, post-polishing of the devices generally involve an etching process that typically results in a 40% to 50% reduction in the as-cut cross-sectional dimensions.

Although FIG. 30 represents rail segments devoid of undulations, as previously described herein, it is appreciated that rail segments such as those shown in FIGS. 1A and 4A are also contemplated. Moreover, it is appreciated that other than the rail width characteristics disclosed above, any number of the features and/or characteristics of the vascular treatment devices previously disclosed herein with respect to FIGS. 1 through 29 (e.g., dimensional, spatial, relational, etc.) may be incorporated into a clot retrieval device 6000 according to FIG. 30.

In some implementations the width of rails 6001 and 6002 taper along their length (or a portion thereof) in a substantial uniform and diminishing fashion. In some implementations discrete portions of the rails have a substantially uniform width dimension with transitional tapers being used to join rail portions of different widths. In some implementations discrete portions of the rails have a substantially uniform width dimension with stepped transitions between rail portions of different widths. In other implementations two or more of the preceding width transitional methods are utilized. Although not required, it is preferable that the width transitions occur at portions along the rail struts other than at a junction of the struts (e.g., junctions 6030).

In some implementations, as previously described, struts 6012 and 6013 of the most proximal cell structure 6018 also have an enhanced width dimension that may be equal to or less than the maximum rail width dimension for the purpose of enhancing the pushability of the clot retrieval device as it is advanced through the tortuous anatomy of a patient. In some implementations less than the entire length of struts 6012 and 6013 are provided with an enhanced width dimension. For example, in some implementations an enhanced width portion extends from a proximal most end of struts 6012 and 6013 and terminates a distance prior to juncture 6026. The configuration of struts 6012 and 6013 may also be altered in manners previously disclosed.

With continued reference to FIG. 30, in exemplary implementations all or portions of struts 6003 and 6004 (and optionally all or the proximal portions of struts 6005 and 6006) have width dimensions between about 0.0045 inches and about 0.0050 inches, all or portions of struts 6007 and 6008 (and optionally all or the distal portions of struts 6005 and 6006) have width dimensions between about 0.0035 inches and about 0.0036 inches, all or portions of struts 6009 and 6010 (and optionally all or the distal portions of struts 6007 and 6008) have width dimensions between about 0.0027 inches and about 0.0035 inches, and with a substantial portion of the strut elements in the remaining portions of the device (portions A, B and C) having width dimensions between about 0.0027 inches and about 0.0034 inches. In one or more of the immediately preceding implementations, the width dimension of struts 6012 and 6013 is between about 0.0033 inches and about 0.0047 inches, and preferably between about 0.0033 inches and about 0.0040 inches. It is to be appreciated that the dimensions disclosed throughout this disclosure relate to exemplary implementations and are also subject to customary manufacturing tolerances. Variations in the dimensions are possible and contemplated.

Although not required, it is preferable that the width transitions occur at portions along the struts themselves other than at a junction of the struts (e.g., junctions 6030 and 6032).

In one exemplary implementation struts 6003-6006 have a width dimension of about 0.0047 inches, struts 6007, 6008 and a proximal portion of strut 6010 have a width dimension of about 0.0036 inches, struts 6009, 6011 and a distal portion of strut 6010 have a width dimension of about 0.0035 inches, struts 6012-6013 have a width dimension of about 0.0036 inches, with all or a substantial portion of the remaining strut elements of the treatment device having a width dimension of about 0.0027 inches.

Testing has shown the proximal taper region of the treatment devices of FIG. 30 to possess good force transmission characteristics along with good radial force characteristics that provide good sheathing and re-sheathing of the proximal taper portion into an introducer sheath and/or delivery catheter.

In another exemplary implementation struts 6003-6006 have a width dimension of about 0.0047 inches, struts 6007, 6008 and a proximal portion of strut 6010 have a width dimension of about 0.0036 inches, struts 6009, 6011 and a distal portion of strut 6010 have a width dimension of about 0.0035 inches, struts 6012-6013 have a width dimension of about 0.0036 inches, the remaining strut elements in section A of the clot retrieval device having a width dimension of about 0.0033 inches and the remaining strut elements generally located in sections B and C of the clot retrieval device having a width dimension of about 0.0027 inches. The increased width dimension of the struts in section A advantageously reduces the likelihood of struts buckling within the proximal taper region of the clot retrieval device and also increases the radial strength of the proximal taper region.

In another exemplary implementation struts 6003-6006 have a width dimension of about 0.0047 inches, struts 6007, 6008 and a proximal portion of strut 6010 have a width dimension of about 0.0036 inches, struts 6009, 6011 and a distal portion of strut 6010 have a width dimension of about 0.0035 inches, the remaining strut elements in section D of the treatment device having a width dimension of about 0.0033 inches and the remaining strut elements of sections B and C of the treatment device having a width dimension of about 0.0027 inches. The increased width dimension of the struts in section A advantageously reduces the likelihood of struts buckling within the proximal taper region of the clot retrieval device during its delivery to a treatment site of a patient and also increases the radial strength of the proximal taper region.

In another exemplary implementation struts 6003-6006 have a width dimension of about 0.0047 inches, struts 6007, 6008 and a proximal portion of strut 6010 have a width dimension of about 0.0036 inches, struts 6009, 6011 and a distal portion of strut 6010 have a width dimension of about 0.0035 inches, struts 6012-6013 have a width dimension of about 0.0036 inches, the strut elements generally located in section C of the clot retrieval device having a width dimension of about 0.0033 inches, and the remaining strut elements of sections A and B of the clot retrieval device having a width dimension of about 0.0027 inches. The increased width dimension of the struts in section C advantageously reduces the likelihood of struts buckling within the distal taper region of the clot retrieval device during its delivery to a treatment site of a patient. The increased width dimension also increases the radial strength of the proximal taper region that enhances the ability of the distal taper region to remain open while the clot retrieval device is withdrawn from a patient. This feature is particularly advantageous when the clot retrieval device is used for clot removal in that it enables the distal taper section to remain open and sweep away remaining portions of the clot when the clot retrieval device is being withdrawn from the patient.

According to some implementations the clot retrieval devices 6000 according to FIG. 30 are laser cut from a tube having an inner diameter of about 2.667 millimeters and a wall thickness of between about 0.102 millimeters to about 0.126 millimeters. In use, a clot retrieval device 6000 according to an implementation of that shown in FIG. 30 is advanced through the tortuous vascular anatomy or bodily duct of a patient to a treatment site in an unexpanded or compressed state of a first nominal diameter and is movable from the unexpanded state to a radially expanded state of a second nominal diameter greater than the first nominal diameter for deployment at the treatment site. In alternative exemplary embodiments the second nominal diameter (e.g., average diameter of main body portion) is about 4.0±0.5 millimeters. In some implementation, the dimensional and material characteristics of the cell structures 6020 generally residing in the main body (section B) of the expandable material are selected to produce sufficient radial force and contact interaction to cause the cell structures 6020 to engage with an embolic obstruction/clot residing in the vascular in a manner that permits partial or full removal of the embolic obstruction from the patient.

In some implementations the dimensional and material characteristics of the elements along the expandable length of the retrieval device are selected to produce a radial force per unit length of between about 0.030 N/mm to about 0.055 N/mm when the outer diameter of the retrieval device is restrained to 1.5 millimeters. In some implementations the dimensional and material characteristics of the elements along the expandable length are selected to produce a radial force per unit length of between about 0.035 N/mm to about 0.050 N/mm when the outer diameter of the retrieval device is restrained to 1.5 millimeters. In some implementations the dimensional and material characteristics of the elements along the expandable length are selected to produce a radial force per unit length of between about 0.037 N/mm to about 0.049 N/mm when the outer diameter of the retrieval device is restrained to 1.5 millimeters. Among the same or alternative implementations, the dimensional and material characteristics of the elements along the expandable length of the retrieval device are selected to produce a radial force of between about 0.010 N/mm to about 0.020 N/mm when the nominal diameter of the main body portion is about 3.0±0.5 millimeters.

In the implementations of FIG. 30, many of the cell structures (excluding those that are formed at least in part by rail segments 6001 and 6002) are shown having similar shapes with most of the cell structure including a pair of short struts 6022 and a pair of long struts 6023. According to some implementations the area of the cells are about 4.00±0.5 mm². In an exemplary implementation the cell areas are about 4.2 mm². In exemplary implementations, short struts 6022 have a length of between about 0.080 and about 0.100 inches, long struts 6023 have a length of between about 0.130 and about 0.140 inches to produce a staggered cell arrangement about the circumference of the treatment device. In some implementations the overall length of the expandable portion of the clot retrieval device is between about 35.0 to about 45.0 millimeters with the main body portion (section B) having a length of about 20.0 to about 25.0 millimeters. In one exemplary embodiment the overall length of the expandable portion of the clot retrieval device is about 42.7 millimeters with the main body portion (section B) having a length of about 21.7 millimeters and the proximal and distal taper regions having a length of about 12.4 millimeters and about 8.6 millimeters, respectively.

Figure 31:
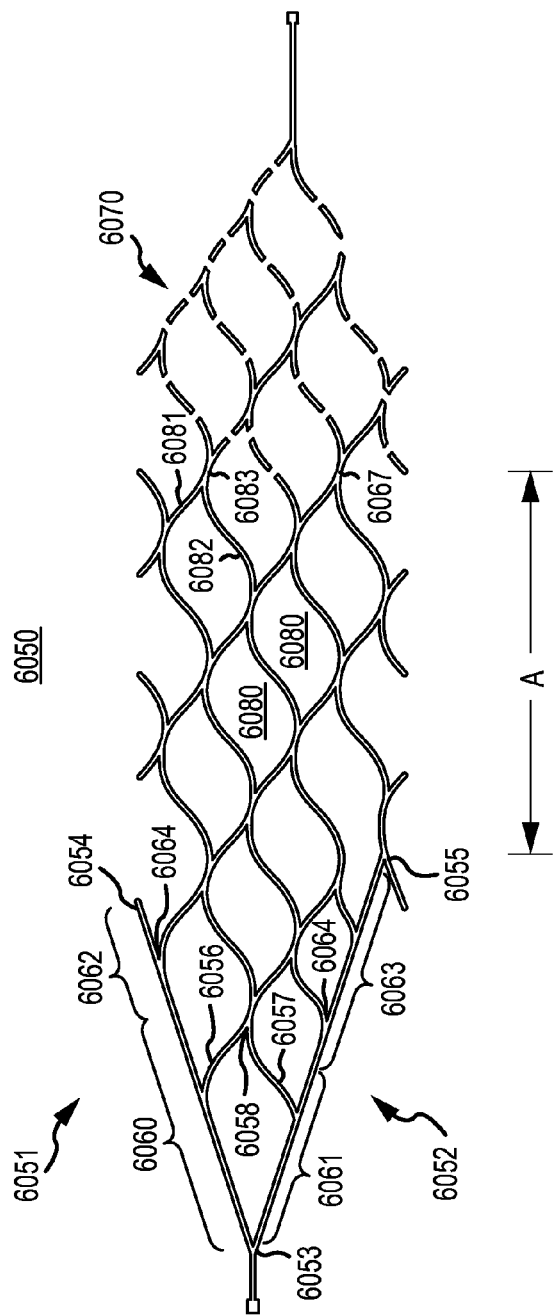
FIG. 31 illustrates a two-dimensional plane view of clot retrieval devices according some implementations.

FIG. 31 illustrates clot retrieval devices 6050 according to other implementations where, among other features, the strut elements of rail segments 6051 and 6052 have varying width dimensions. Clot retrieval device 6050 is particularly adapted for the treatment of small diameter vessels/duct. In one implementation, as shown in FIG. 31, the circumference of the main body portion (section A) comprises three cell structures 6080, but is not limited to such a construction. FIG. 31 depicts the clot retrieval treatment device 6050 in a two-dimensional plane view as if the device were cut and laid flat on a surface. FIG. 31 depicts the device in its manufactured (as-cut) configuration. In one implementation, rail segment 6051 transitions from a maximum width dimension at or near its proximal end 6053 to a minimum width dimension at or near its distal end 6054. In a like manner, rail segment 6052 transitions from a maximum width dimension at or near its proximal end 6053 to a minimum width dimension at or near its distal end 6055. As previously discussed, the width dimensions of the rail segments are selected to enhance their ability to distribute forces and to resist buckling when a push force is applied to the proximal end 6053 of the vascular treatment device. In some implementations the percentage change between the maximum rail width dimension and the minimum rail width dimension is between about 20.0% and about 30.0%, and preferably between about 20% and about 25%. In an exemplary implementation the width dimension of the rail segments transitions from a maximum width dimension of about 0.0047±0.0004 inches to a minimum width dimension of about 0.0036±0.0004 inches.

Although FIG. 31 represents rail segments 6051 and 6052 that are devoid of undulations, as previously described herein, it is appreciated that rail segments such as those shown in FIGS. 1A and 4A are also contemplated. Moreover, it is appreciated that other than the rail width characteristics disclosed above, any number of the features and/or characteristics of the treatment devices previously described herein with respect to FIGS. 1 through 29 (e.g., dimensional, spatial, relational, etc.) may be incorporated into a clot retrieval device 6050 according to FIG. 31.

In some implementations the width of rail 6051 and 6052 taper along their length (or a portion thereof) in a substantial uniform and diminishing fashion. In some implementations discrete portions of the rails have a substantially uniform width dimension with only transitional tapers being used to join rail portions of different widths. In some implementations discrete portions of the rails have a substantially uniform width dimension with stepped transitions between rail portions of different widths. In other implementations two or more of the preceding width transitional methods are utilized. Although not required, it is preferable that the width transitions occur at portions along the rail struts other than strut junctions (e.g., junctions 6064).

In some implementations struts 6056 and 6057 of the most proximal cell structure also have enhanced width dimensions that may be equal to or less than the maximum rail width dimension for the purpose of enhancing the pushability of the clot retrieval device as it is advanced through the tortuous anatomy of a patient. In some implementations less than the entire length of struts 6056 and 6057 are provided with an enhanced width dimension. For example, in some implementations an enhanced width portion extends from a proximal most end of struts 6056 and 6057 and terminates a distance prior to juncture 6058. Moreover, the configuration of struts 6056 and 6057 may also be altered in manners previously disclosed.

With continued reference to FIG. 31, in exemplary implementations rail portions 6060 and 6061 have width dimensions of about 0.0047 and rail portions 6062 and 6063 have width dimensions of about 0.0036 inches, with a substantial portion of the strut elements in the remaining portions of the device 6050 having a width dimension of about 0.0027 inches. In other exemplary implementations rail portions 6060 and 6061 have width dimensions of about 0.0047 and rail portions 6062 and 6063 have width dimensions of about 0.0036 inches, with the struts in a distal portion 6070 of device (illustrated with dashed lines) having a width dimension of about 0.0023 inches and a majority of the remaining struts having a width dimension of about 0.0027 inches. The reduced width dimension of distal portion 6070 produces a region of lower radial strength that in smaller vessels or ducts minimizes surface interactions between the distal portion 6070 and the vessel/duct to prevent or minimize the occurrence of damage to the vessel/duct wall while the clot retrieval device is proximally withdrawn from a patient.

Testing has shown the proximal taper region of the clot retrieval devices 6050 to possess good force transmission characteristics along with good radial force characteristics that provide good sheathing and re-sheathing of the proximal taper portion into an introducer sheath and/or delivery catheter.

According to some implementations the clot retrieval devices 6050 according to FIG. 31 are laser cut from a tube having an inner diameter of about 2.130 millimeters and a wall thickness of between about 0.104 millimeters to about 0.128 millimeters. In use, a clot retrieval device 6050 according to an implementation of that shown in FIG. 31 is advanced through the tortuous vascular anatomy or bodily duct of a patient to a treatment site in an unexpanded or compressed state of a first nominal diameter and is movable from the unexpanded state to a radially expanded state of a second nominal diameter greater than the first nominal diameter for deployment at the treatment site. In alternative exemplary embodiments the second nominal diameter (e.g., average diameter of main body portion) is about 3.0±0.5 millimeters. In some implementation, the dimensional and material characteristics of the cell structures 6080 residing in the main body portion (section A) are selected to produce sufficient radial force and contact interaction to cause the cell structures 6080 to engage with an embolic obstruction residing in the vascular in a manner that permits partial or full removal of the embolic obstruction from the patient.

In some implementations the dimensional and material characteristics of the elements along the expandable length of the retrieval device are selected to produce a radial force per unit length of between about 0.015 N/mm to about 0.035 N/mm when the outer diameter of the retrieval device is restrained to 1.5 millimeters. In some implementations the dimensional and material characteristics of the elements along the expandable length are selected to produce a radial force per unit length of between about 0.017 N/mm to about 0.033 N/mm when the outer diameter of the retrieval device is restrained to 1.5 millimeters. Among the same or alternative implementations, the dimensional and material characteristics of the elements along the expandable length of the retrieval device are selected to produce a radial force of between about 0.010 N/mm to about 0.020 N/mm when the nominal diameter of the main body portion is about 2.0±0.5 millimeters.

Figure 32A:
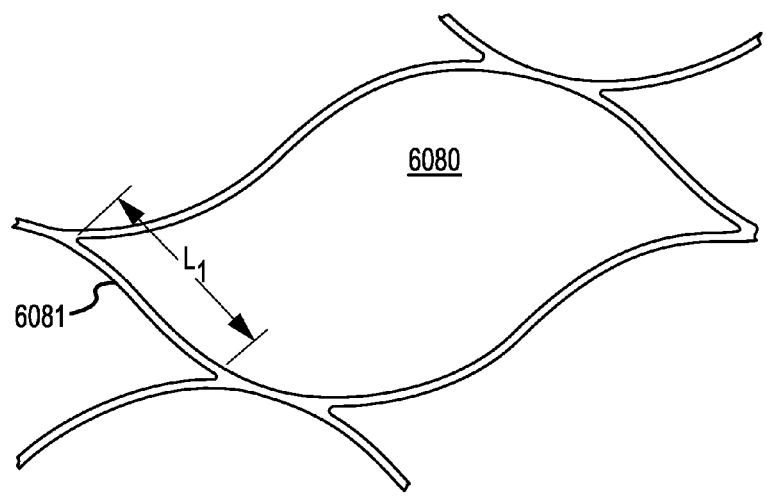
FIGS. 32A-C illustrate cell structures according to some of the implementations of FIG. 31.
Figure 32B:
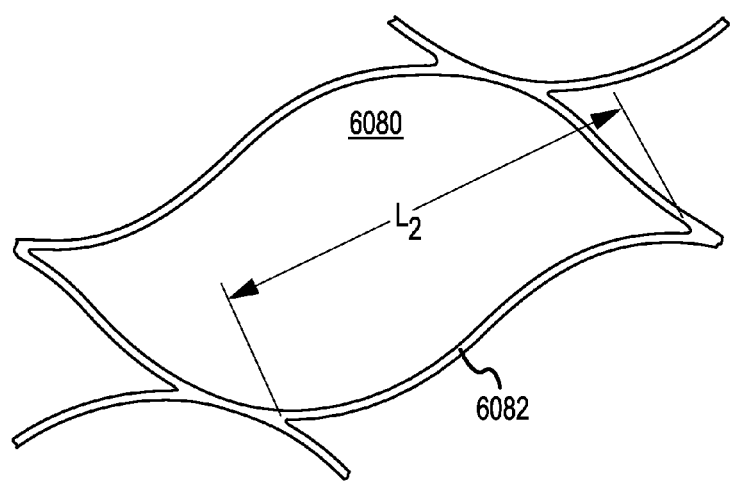
Figure 32C:
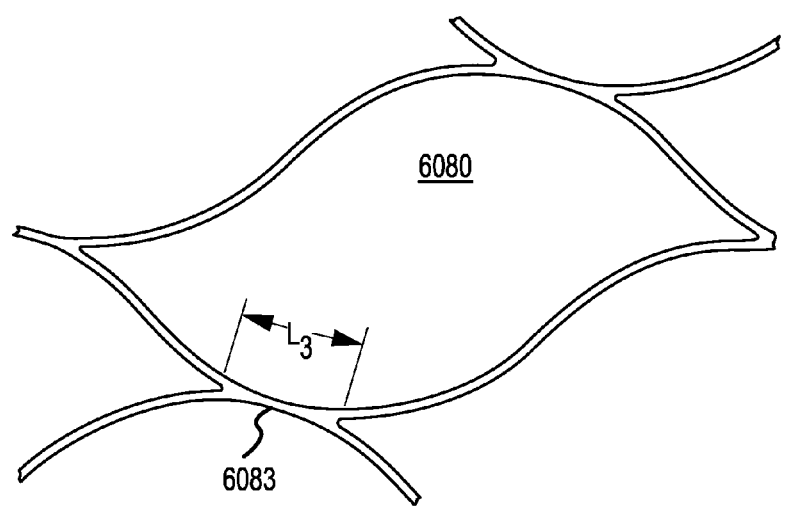

In the implementations of FIG. 31, many of the cell structures (excluding those that are formed at least in part by rail segments 6051 and 6052) are shown having similar shapes with most of the cell structure including a pair of short struts 6081 and a pair of long struts 6082 that are joined by connector regions 6083. In exemplary implementations (as shown in FIGS. 32A-C), short struts 6081 have a linear length, $L_1$, of about 0.055±0.010 inches, long struts 6082 have a linear length, $L_3$, of about 0.128±0.010 inches and connector regions 6083 have a linear length, $L_3$, of about 0.0371±0.010 inches. In one or more implementations the cell structures 6080 have an area of about 4.5 mm$^2$ to about 5.5 mm$^2$. In one exemplary implementation the cell structures 6080 have an area of about 5.0 mm$^2$. In exemplary implementations the overall length of the expandable portion of the clot retrieval device is between about 25.0 millimeters and about 35.0 millimeters with the main body portion (section A) having a length of between about 10.0 millimeters and about 15.0 millimeters. In one exemplary implementation the overall length of the expandable portion of the clot retrieval device is about 30.7 millimeters with the main body portion (section A) having a length of about 13.1 millimeters and the proximal and distal taper regions having a length of about 10.9 millimeters and about 6.7 millimeters, respectively.

Figure 33A:
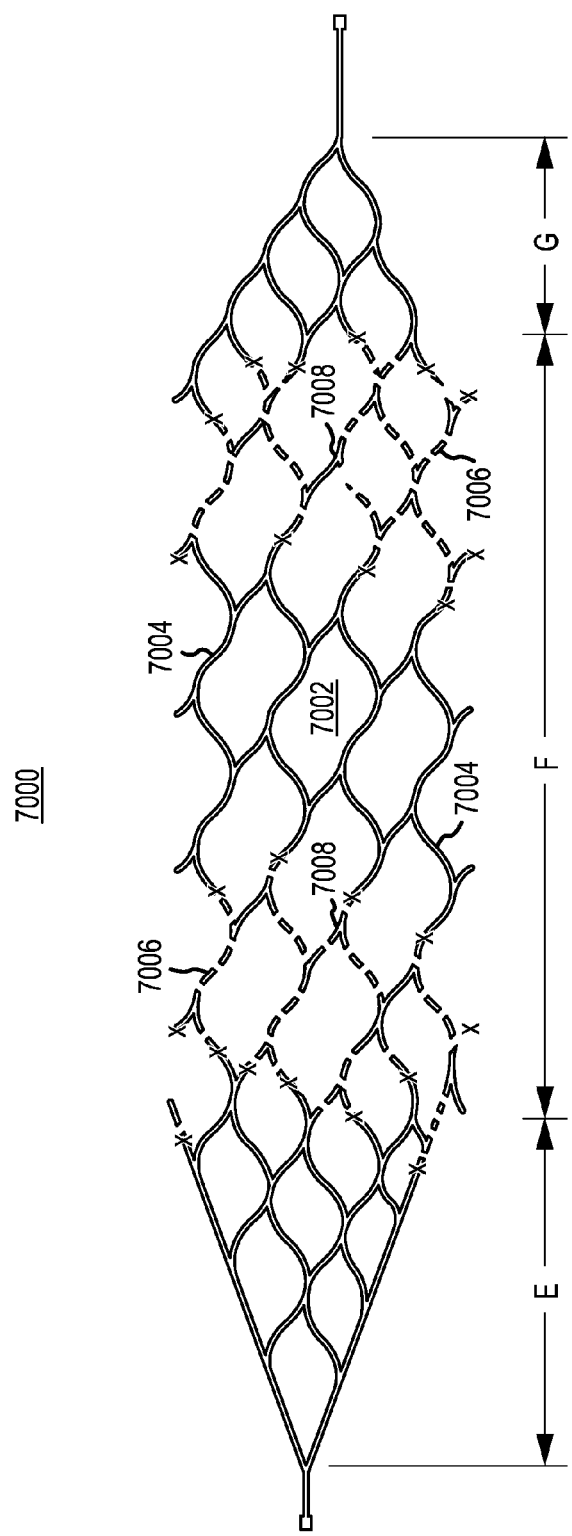
FIG. 33A illustrates a two-dimensional plane view of clot retrieval devices according some implementations.
Figure 33B:
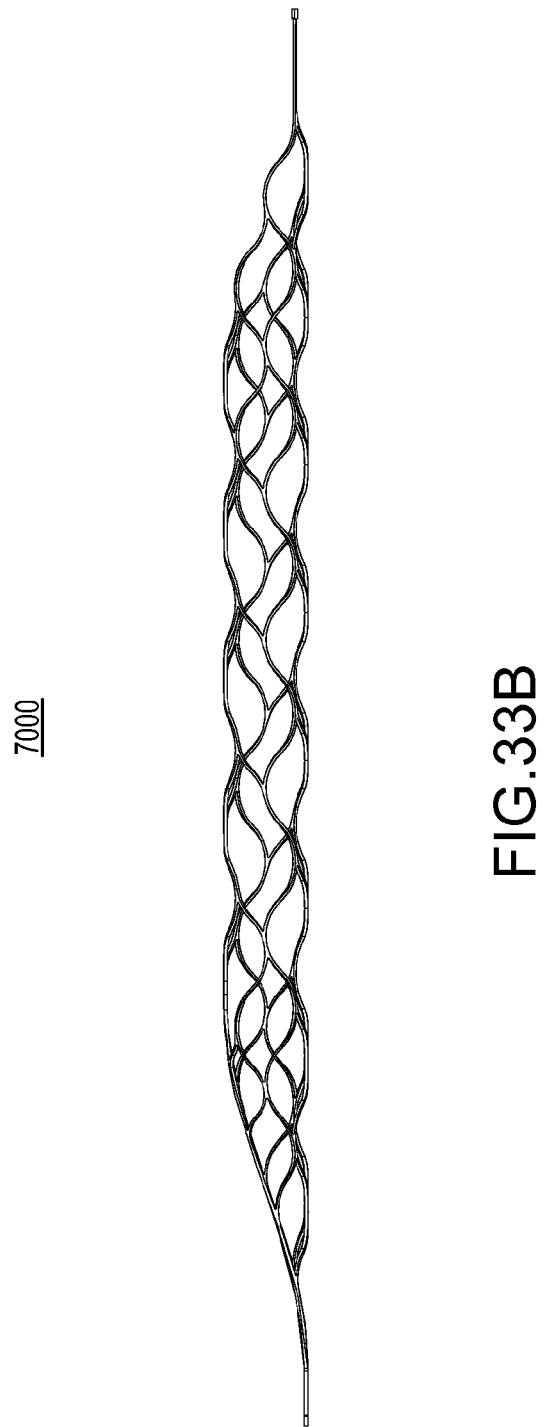
FIGS. 33B and 33C illustrate top and side isometric views of the device illustrated in FIG. 33A.
Figure 33C:
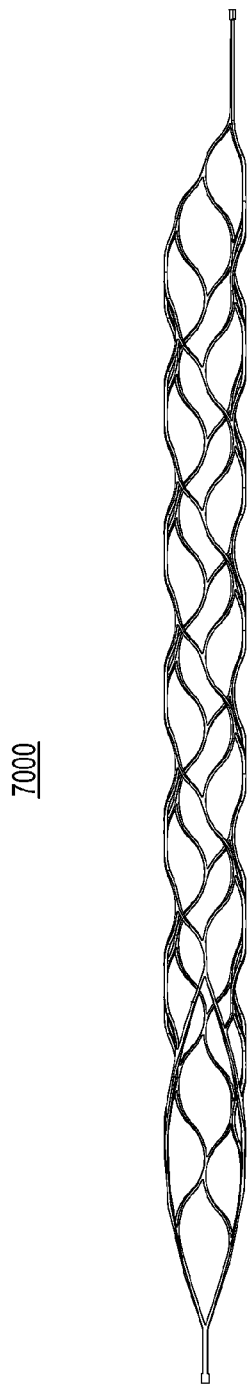

Turning now to FIG. 33A, an alternative implementation to the clot retrieval devices described above in conjunction with FIG. 30 is depicted. FIGS. 33B and 33C illustrate exemplary three-dimensional top and side views of the clot retrieval devices 7000 of FIG. 33A. Sections of the treatment device 7000 that are generally identified as regions E and G are in many respects similar, and in some instances the same, to the same general regions of the clot retrieval devices 6000 described above. As an example, the width dimension of the struts generally located in region G may in different implementations take different values to establish any of a variety of desired distal taper characteristics as disclosed above. In addition, region E may assume any of a variety of implementations as previously disclosed above in conjunction with the retrieval devices of FIG. 30. As shown in FIG. 33A, the sizes of the cell structures 7002 generally located in a central region F of the device 7000 are larger than those in the implementations of devices 6000 described above. An advantage of the decreased strut density in the central region F of device 7000 is that it enhances the integration of an embolic obstruction/clot within region F of the device. In the treatment devices 7000 of FIG. 33, the larger cell structures are created by the omission of selected long struts 6022 in the device 6000 of FIG. 30 to create cell structures 7002 having areas that are about double the size of cells 7024. In one implementation, cell structures 7020 have an area of between about 8.0 mm$^2$ and about 8.5 mm$^2$. In one exemplary implementation cell structures 7020 have an area of about 8.3 mm$^2$. It is important to note that any of a number of other methods may be used to create the larger cell structures. A particular advantage of the implementations of FIG. 33 is that good strut nesting characteristics are preserved to facilitate a low profile delivery state of the device 7000.

A decrease in the strut density in a region generally results in a lower radial strength within the region. In a clot retrieval device this reduction can adversely affect the device's ability to integrate with an embolic obstruction/clot. To compensate for this reduction in radial strength, in some implementations selective strut portions 7006 (denoted by dashed lines) generally located within region F of the retrieval devices are provided with a width dimension greater than the width dimension of strut portions 7004 (denoted by solid lines). In accordance with some implementations the width dimensions of strut portions 7006 are selected so that the over-all radial strength per unit length of expandable portion of the retrieval device is similar to that absent the removal of struts to create the larger sized cell structures. As an example, in the implementations described above where decreased strut density is achieved by the omission of certain long struts 6022 in a device of FIG. 30, the width of struts 7006 are selected so that the over-all radial strength per unit length of the expandable portion of the retrieval device is similar to that of devices 6000 described above. For example, in some implementations strut portions 7004 have a width dimension of about 0.0027 inches with strut portions 7006 having a width dimension of about 0.0035 inches so that the over-all radial strength per unit length of the expandable portion is similar to the same area of the retrieval devices 6000 having mostly unitary cell sizes and strut width dimensions of about 0.0027 inches.

Although not required, as illustrated in FIG. 33A, the transition of strut widths preferably occur at locations (denoted by "x") other than junctions 7008. Although not required, the width transitions preferably comprise tapers that provide a relatively smooth transition between the different width dimensions.

Strut portions of enhanced width 7006 are one method of creating a desired over-all radial strength per unit length. Other methods are also available. For example, strut portions 7006 may instead have an enhanced thickness dimension over strut portions 7004, or may have a combination of enhanced thickness and width dimensions. In other implementations the width dimension of a majority, substantially all or all of the struts generally located in section F are enhanced to compensate for the reduction in strut density.

Figure 34B:
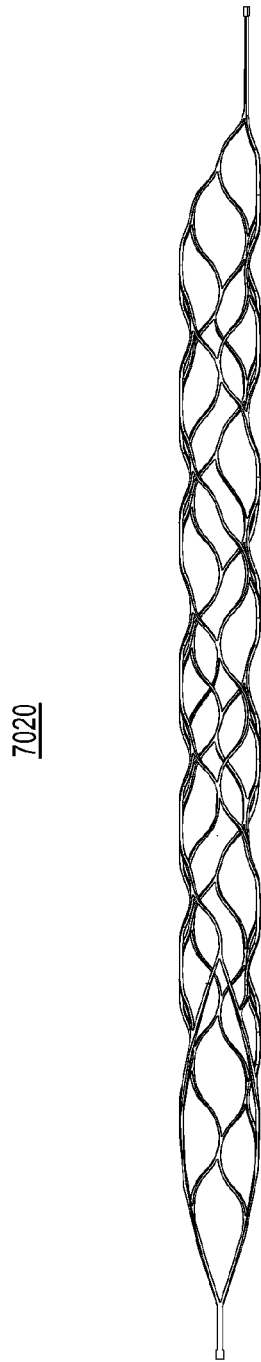
FIGS. 34B and 34C illustrate top and side isometric views of the device illustrated in FIG. 34A.
Figure 34C:
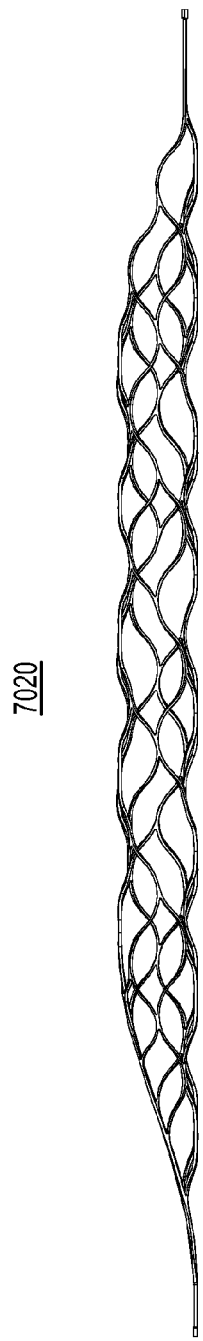

With reference to FIG. 34A, alternative implementations to the clot retrieval devices described above in conjunction with FIG. 30 are depicted. FIGS. 34B and 34C illustrate exemplary three-dimensional top and side views of the clot retrieval devices 7020 of FIG. 34A. Sections of the treatment device 7020 that are generally identified as regions E and G are in many respects similar, and in some instances the same, to the same general regions of the clot retrieval devices 6000 described above. As an example, the width dimension of the struts in region G may, in different implementations, take different values to establish any of a variety of desired distal taper characteristics as disclosed above. In addition, region E may assume any of a variety of implementations as previously disclosed above in conjunction with the retrieval devices of FIG. 30. As shown in FIG. 34A, the sizes of some of the cell structures 7022 in a central region J of the device 7020 are larger than those in the implementations of devices 6000 described above to provide circumferentially extending zones of decreased strut density that are generally separated by circumferentially extending rows of non-enlarged cell structures 7024. In the treatment devices 7020 of FIG. 34, the larger cell structures are created by the omission of selected long struts 6022 in the device 6000 of FIG. 30 to create cell structures 7022 having areas of about double in size. In one implementation cell structures 7022 have an area of about 8.3 mm$^2$. It is important to note that any of a number of other methods may be used to create the larger cell structures. A particular advantage of the implementations of FIG. 34 is that good strut nesting characteristics are preserved to facilitate a low profile delivery state of the device 7020.

As discussed above, a decrease in the strut density in a region generally results in a lower radial strength within the region. In a clot retrieval device this reduction can adversely affect the device's ability to integrate with an embolic obstruction/clot. To compensate for this reduction in radial strength, selective strut portions 7026 (denoted by dashed lines) generally located within region J of the retrieval devices are provided with a width dimension greater than the width dimension of strut portions 7025 (denoted by solid lines). In accordance with some implementations the width dimensions of strut portions 7026 are selected so that the over-all radial strength per unit length of the expandable portion of the retrieval device is similar to that absent the removal of struts to create the larger sized cell structures. As an example, in the implementations described above where decreased strut density is achieved by the omission of certain long struts 6022 in a device of FIG. 30, the width of struts 7026 are selected so that the over-all radial strength per unit length of the expandable portion of the retrieval device is similar to that of devices 6000 described above. For example, in some implementations strut portions 7025 have a width dimension of about 0.0027 inches with strut portions 7026 having a width dimension of about 0.0035 inches so that the over-all radial strength per unit length of the expandable portion of the retrieval device is similar to the same area of the retrieval devices 6000 having mostly unitary cell sizes and strut width dimensions of about 0.0027 inches. In some implementation the width of the struts 7029 have a width dimension of between 0.0031 inches and about 0.0033 inches similar to those previously discussed above with respect to some implementations of device 6000.

In some implementations, as illustrated in FIG. 34A, the transition of some or all of the strut widths occur at locations other than junctions 7028, while in other implementations the transition of some or all of the strut widths occur at locations other than junctions 7028. Although not required, the width transitions preferably comprise tapers that provide a relatively smooth transition between the different width dimensions.

Strut portions of enhanced width 7026 are one method of creating in region J a desired over-all radial strength. Other methods are also available. For example, strut portions 7026 may instead have an enhanced thickness dimension over strut portions 7025, or may have a combination of enhanced thickness and width dimensions.

Figure 35B:
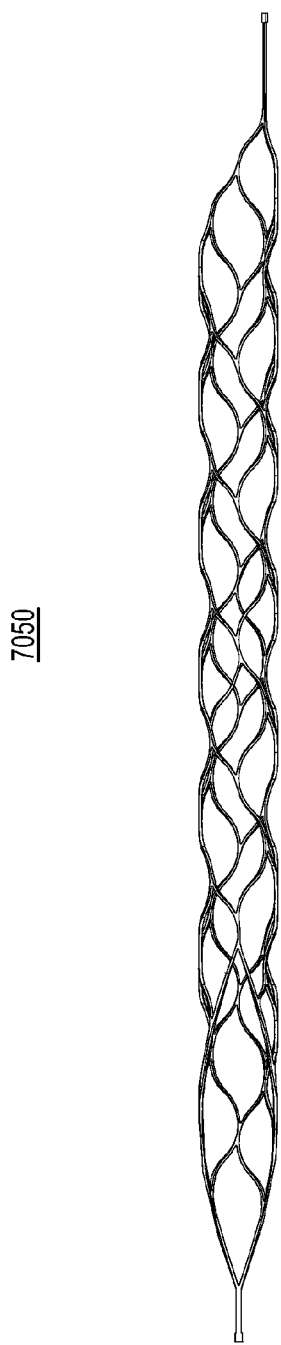
FIGS. 35B and 35C illustrate top and side isometric views of the device illustrated in FIG. 35A.
Figure 35C:

With reference to FIG. 35A, an alternative implementation to the clot retrieval devices described above in conjunction with FIG. 30 is depicted. FIGS. 35B and 35C illustrate exemplary three-dimensional top and side views of the clot retrieval devices 7050 of FIG. 35A. Sections of the treatment device 7050 that are generally identified as regions E and G are in many respects similar, and in some instances the same, to the same general regions of the clot retrieval devices 6000 described above. As an example, the width dimension of the struts generally located in region G may in different implementations take different values to establish any of a variety of desired distal taper characteristics as disclosed above. In addition, region E may assume any of a variety of implementations as previously disclosed above in conjunction with the retrieval devices of FIG. 30. As shown in FIG. 35A, the sizes of some of the cell structures 7052 in a central region K of the device 7050 are larger than those in the implementations of devices 6000 described above to provide zones of decreased strut density that are dispersed among non-enlarged cell structures 7054. In the treatment devices 7050 of FIG. 35, the larger cell structures are created by the omission of selected long struts 6022 in the device 6000 of FIG. 30 to create cell structures 7052 having areas of about double the size of cells 7054. In one implementation the area of cell structures 7052 is about 8.3 mm$^2$. It is important to note that any of a number of other methods may be used to create the larger cell structures. A particular advantage of the implementations of FIG. 35 is that good strut nesting characteristics are preserved to facilitate a low profile delivery state of the device 7050.

As discussed above, a decrease in the strut density in a region generally results in a lower radial strength within the region. In a clot retrieval device this reduction can adversely affect the device's ability to integrate with an embolic obstruction/clot. To compensate for this reduction in radial strength, selective strut portions 7056 (denoted by dashed lines) generally located within region K of the retrieval devices are provided with a width dimension greater than the width dimension of strut portions 7055 (denoted by solid lines). In accordance with some implementations the width dimensions of strut portions 7056 are selected so that the over-all radial strength per unit length of the expandable portion of the retrieval device is similar to that absent the removal of struts to create the larger sized cell structures. As an example, in the implementations described above where decreased strut density is achieved by the omission of certain long struts 6022 in a device of FIG. 30, the width of struts 7056 are selected so that the over-all radial strength per unit length of the expandable portion of the retrieval device is similar to that of devices 6000 described above. For example, in some implementations strut portions 7055 have a width dimension of about 0.0027 inches with strut portions 7056 having a width dimension of about 0.0035 inches so that the over-all radial strength per unit length of the expandable portion of the retrieval device is similar to the same area of the retrieval devices 6000 having mostly unitary cell sizes and strut width dimensions of about 0.0027 inches. In some implementations the width of the struts 7059 have a width dimension of between 0.0031 inches and about 0.0033 inches similar to those previously discussed above with respect to some implementations of device 6000.

Although not required, as illustrated in FIG. 35A, the transition of strut widths preferably occur at locations other than junctions 7058. Although not required, the width transitions preferably comprise tapers that provide a relatively smooth transition between the different width dimensions.

Strut portions of enhanced width 7056 are one method of creating a desired over-all radial strength per unit length. Other methods are also available. For example, strut portions 7056 may instead have an enhanced thickness dimension over strut portions 7055, or may have a combination of enhanced thickness and width dimensions.

Figure 36:
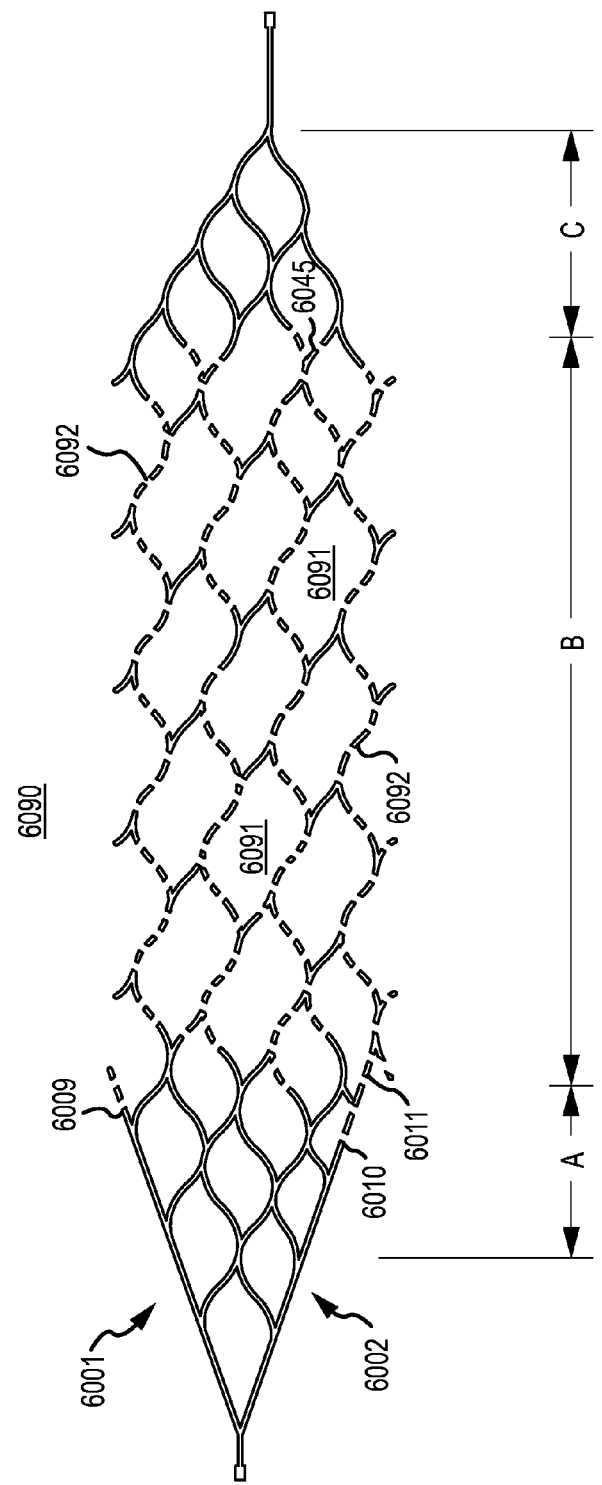
FIG. 36 illustrates a two-dimensional plane view of clot retrieval devices according some implementations.

FIG. 36 illustrates clot retrieval devices 6090 similar to those of FIG. 30, with a difference in the size of the cell structures 6091 generally located in region B of the device. As illustrated in FIG. 36, cell structures 6091 are of a greater size than the cell structures 6020 of the device shown in FIG. 30. As previously discussed, an advantage of larger sized cell structures within the main body portion of the retrieval device is that it enhances clot integration into the main body portion when a radial strength of the main body portion is properly provided. For the purpose of providing sufficient radial strength in region B of the device 6090, the struts 6092 (denoted by dashed lines) generally located within region B have an enhanced width dimension, which in one implementation is about 0.0035 inches. In one implementation the width dimension of the struts 6092 generally located in region B are similar to or the same as the width dimension of the distal sections of rail segments 6001 and/or 6002 (e.g., having the same or similar width dimension of one or more of struts 6009, 6010 and 6011). Although not required, the transition in width dimensions preferably occur at locations other than at junctions 6045, as illustrated in FIG. 36.

Figure 37:
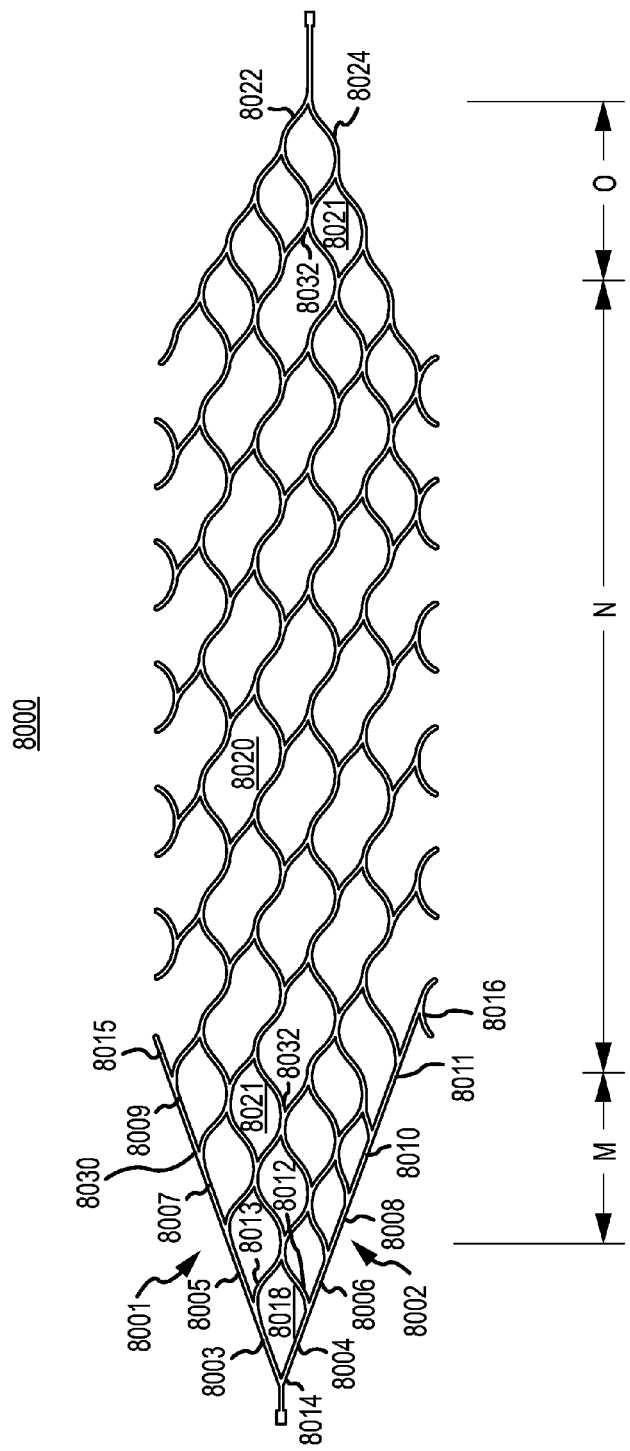
FIG. 37 illustrates a two-dimensional plane view of clot retrieval devices according some implementations.

FIG. 37 illustrates clot retrieval devices 8000 according to other implementations where, among other features, the strut elements of rail segments 8001 and 8002 have varying width dimensions. FIG. 37 depicts a clot retrieval device in a two-dimensional plane view as if the device were cut and laid flat on a surface. FIG. 37 depicts the device in its manufactured (as-cut) configuration. In one implementation, rail segment 8001 transitions from a maximum width dimension at or near its proximal end 8014 to a minimum width dimension at or near its distal end 8015. In a like manner, rail segment 8002 transitions from a maximum width dimension at or near its proximal end 8014 to a minimum width dimension at or near its distal end 8016. As previously discussed, the width dimensions of the rail segments are selected to enhance their ability to distribute forces and to resist buckling when a push force is applied to the proximal end 8014 of the clot retrieval device. In some implementations the percentage change between the maximum rail width dimension and the minimum rail width dimension is between about 20.0% and about 35.0%. In other implementations the percentage change between the maximum rail width dimension and the minimum rail width dimension is between about 25.0% and about 30.0%. In an exemplary implementation the width dimension of the rail segments transitions from a maximum width dimension of about 0.0047±0.0004 inches to a minimum width dimension of about 0.0027±0.0004 inches. In another exemplary implementation the width dimension of the rail segments transitions from a maximum width dimension of about 0.0047±0.0004 inches to a minimum width dimension of about 0.0034±0.0004 inches.

Although FIG. 37 represents rail segments that are devoid of undulations, as previously described herein, it is appreciated that rail segments such as those shown in FIGS. 1A and 4A are also contemplated. Like the devices of FIG. 30 disclosed above, it is appreciated that other than the rail width characteristics disclosed in the preceding paragraph, any of a number of the features and/or characteristics of the vascular treatment devices described in conjunction with the devices of FIGS. 1-29 (e.g., dimensional, spatial, relational, etc.) may be incorporated into a clot retrieval device 8000 according to FIG. 37.

In some implementations the width of rails 8001 and 8002 taper along their length (or a portion thereof) in a substantial uniform and diminishing fashion. In some implementations discrete portions of the rails have a substantially uniform width dimension with only transitional tapers being used to join rail portions of different widths. In some implementations discrete portions of the rails have a substantially uniform width dimension with stepped transitions between rail portions of different widths. In other implementations two or more of the preceding width transitional methods are utilized. Although not required, it is preferable that the width transitions occur at portions along the rail struts other than at a junction of the struts (e.g., junctions 8030).

In some implementations, as previously described, struts 8012 and 8013 of the most proximal cell structure 8018 also have an enhanced width dimension that may be equal to or less than the maximum rail width dimension for the purpose of enhancing the pushability of the clot retrieval device as it is advanced through the tortuous anatomy of a patient. In some implementations less than the entire length of struts 8012 and 8013 are provided with an enhanced width dimension. For example, in some implementations an enhanced width portion extends from a proximal most end of struts 8012 and 8013 and terminates a distance prior to their juncture. The configuration of struts 8012 and 8013 may also be altered in manners previously disclosed.

With continued reference to FIG. 37, in exemplary implementations all or portions of struts 8003 and 8004 (and optionally all or portions of struts 8005 and 8006) have width dimensions of about 0.0045 inches to about 0.0050 inches, all or portions of struts 8007 and 8008 (and optionally all or portions of struts 8005 and 8006) have width dimensions of about 0.0036 inches to about 0.0040 inches, all or portions of struts 8009 and 8010 (and optionally all or portions of struts 8007 and 8008) have width dimensions of about 0.0034 inches to about 0.0036 inches. In some implementations the remainder of the struts generally located in region M of the device have width dimensions of about 0.0027 inches, the struts in region N have width dimensions of about 0.0034 inches to about 0.0036 inches, and the struts generally located in region O have a width dimension of about 0.0031 inches to about 0.033 inches. In one or more of the immediately preceding implementations, the width dimension of struts 8012 and 8013 is between about 0.0036 inches and about 0.0047 inches. It is to be appreciated that the dimensions disclosed relate to exemplary implementations and are also subject to customary manufacturing tolerances. Variations in the dimensions are also possible and contemplated.

Although not required, it is preferable that the width transitions occur at portions along the struts themselves other than at a junction of the struts (e.g., junctions 8030 and 8032).

As illustrated in FIG. 37, the strut density in the region generally identified by "N" is notably less than the strut densities in the regions generally identified by "M" and "O". As a consequence, the cell structures 8020 generally located in region N are of a larger size than the cell structures 8021 generally located in regions N and O. As previously discussed, an advantage of larger sized cell structures within the main body portion of the retrieval device is that it enhances clot integration into the main body portion (region N) when a radial strength of the main body portion is properly provided. For the purpose of providing sufficient radial strength in region N of the device, the struts within region have an enhanced width dimension as compared to the cell struts generally residing in region M (other than the struts 8003-8013) and the cell struts generally residing in region O. In one implementation the width dimension of the struts in region N are similar to or the same as the width dimension of the distal struts 8009, 8010 and/or 8011 of rail segments 8001 and/or 8002.

In an exemplary implementation struts 8003-8006 have a width dimension of about 0.0047 inches, struts 8007, 8008, and a proximal portion of strut 8010 have a width dimension of about 0.0040 inches, struts 8009, 8011 and a distal portion of strut 8010 have a width dimension of about 0.0034 inches, struts 8012-8013 have a width dimension of about 0.0040 inches. In some implementations the remainder of the struts in region M of the device have width dimensions of about 0.0027 inches, the struts in region N have width dimensions of about 0.0034 inches, and the struts in region O have a width dimension of about 0.0031 inches. The increased width dimension of the struts in section O advantageously reduces the likelihood of struts buckling within the distal taper region of the clot retrieval device during its delivery to a treatment site of a patient. The increased width dimension also increases the radial strength of the distal taper region that enhances the ability of the distal taper region to remain open while the clot retrieval device is withdrawn from a patient so that it may sweep away remaining portions of the clot when the clot retrieval device is being withdrawn from the patient.

According to some implementations the clot retrieval devices 8000 according to FIG. 37 are laser cut from a tube having an inner diameter of about 3.77 millimeters and a wall thickness of between about 0.097 millimeters to about 0.131 millimeters. In use, a clot retrieval device 8000 according to an implementation of that shown in FIG. 37 is advanced through the tortuous vascular anatomy or bodily duct of a patient to a treatment site in an unexpanded or compressed state of a first nominal diameter and is movable from the unexpanded state to a radially expanded state of a second nominal diameter greater than the first nominal diameter for deployment at the treatment site. In alternative exemplary embodiments the second nominal diameter (e.g., average diameter of main body portion) is about 5.5±0.5 millimeters. In some implementation, the dimensional and material characteristics of the cell structures 8020 residing in the main body (section N) are selected to produce sufficient radial force and contact interaction to cause the cell structures 8020 to engage with an embolic obstruction/clot residing in the vascular in a manner that permits partial or full removal of the embolic obstruction from the patient.

In some implementations the dimensional and material characteristics of the elements along the expandable length of the retrieval device are selected to produce a radial force per unit length of between about 0.040 N/mm to about 0.065 N/mm when the outer diameter of the retrieval device is restrained to 1.5 millimeters. In some implementations the dimensional and material characteristics of the elements along the expandable length are selected to produce a radial force per unit length of between about 0.045 N/mm to about 0.060 N/mm when the outer diameter of the retrieval device is restrained to 1.5 millimeters. In some implementations the dimensional and material characteristics of the elements along the expandable length are selected to produce a radial force per unit length of between about 0.050 N/mm to about 0.060 N/mm when the outer diameter of the retrieval device is restrained to 1.5 millimeters. In some implementations the dimensional and material characteristics of the elements along the expandable length are selected to produce a radial force per unit length of between about 0.049 N/mm to about 0.057 N/mm when the outer diameter of the retrieval device is restrained to 1.5 millimeters. Among the same or alternative implementations, the dimensional and material characteristics of the elements along the expandable length of the retrieval device are selected to produce a radial force of between about 0.010 N/mm to about 0.020 N/mm when the nominal diameter of the main body portion is about 4.5±0.5 millimeters.

In the implementations of FIG. 37, the cell structures in regions M and O (excluding those that are formed at least in part by rail segments 8001 and 8002) are shown having similar shapes with the cell structures 8021 including a pair of short struts 8022 and a pair of long struts 8024. In exemplary implementations the area of cell structures 8021 is between about 4.5 mm$^2$ and about 5.5 mm$^2$. In one exemplary implementation the area of cell structures 8021 is about 5.0 mm$^2$ to about 5.2 mm$^2$. The cell structures 8020 generally located in region N, in one implementation, comprise a shape consisting of two adjoining cell structures 8021 with a long strut 8024 being omitted between them. Although other types of large sized cell structures are contemplated, an advantage of the cell construction illustrated in FIG. 37 is that it possesses good nesting capability to permit the retrieval device to achieve a small delivery profile.

In some implementations the overall length of the expandable portion of the clot retrieval device is between about 55.0 millimeters and about 65.0 millimeters with the main body portion (section N) having a length of between about 25 millimeters and about 35.0 millimeters and the proximal and distal taper regions having a length of between about 10.0 to about 20.0 millimeters. In one exemplary embodiment the overall length of the expandable portion of the clot retrieval device is about 58.4 millimeters with the main body portion (section N) having a length of about 29.3 millimeters and the proximal and distal taper regions having a length of about 16.6 millimeters and 12.5 millimeters, respectively.

Figure 38:
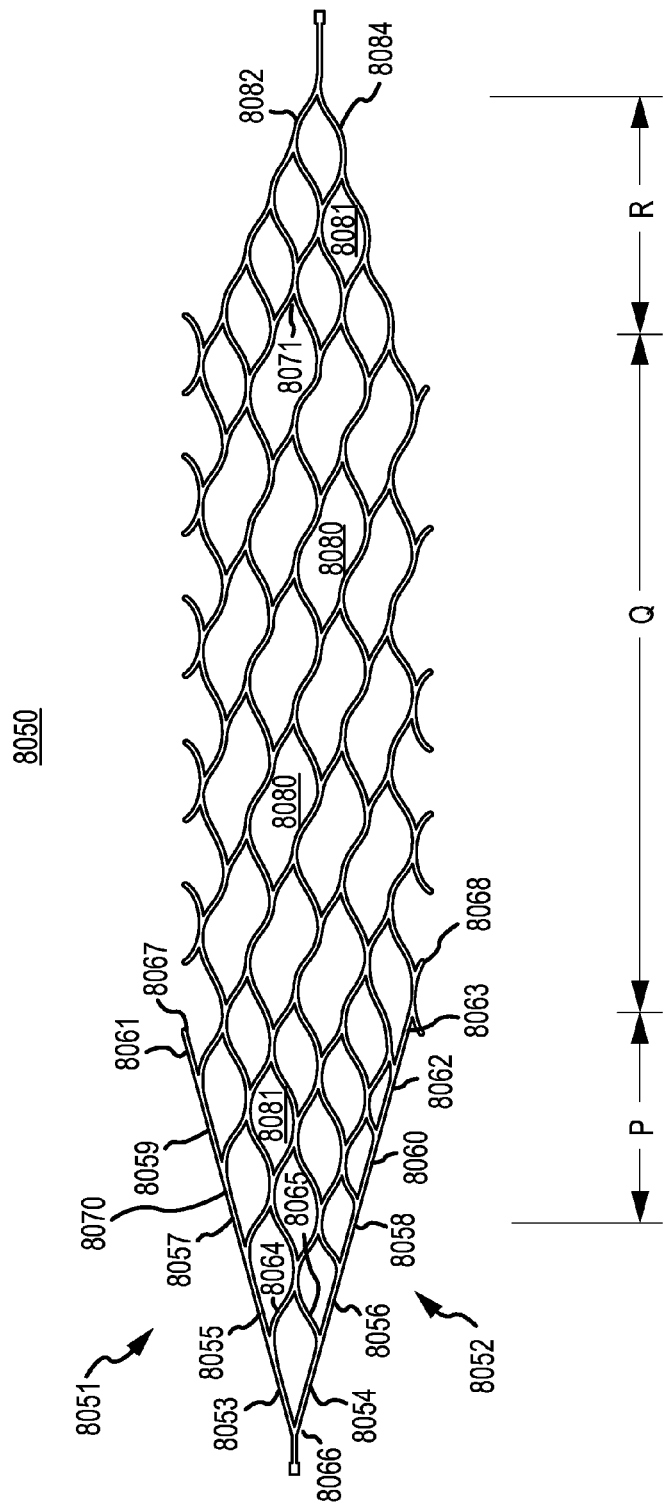
FIG. 38 illustrates a two-dimensional plane view of clot retrieval devices according some implementations.

FIG. 38 illustrates clot retrieval devices 8500 according to other implementations where, among other features, the strut elements of rail segments 8051 and 8052 have varying width dimensions. FIG. 38 depicts a clot retrieval device in a two-dimensional plane view as if the device were cut and laid flat on a surface. FIG. 38 depicts the device in its manufactured (as-cut) configuration. In one implementation, rail segment 8051 transitions from a maximum width dimension at or near its proximal end 8066 to a minimum width dimension at or near its distal end 8067. In a like manner, rail segment 8052 transitions from a maximum width dimension at or near its proximal end 8066 to a minimum width dimension at or near its distal end 8068. As previously discussed, the width dimensions of the rail segments are selected to enhance their ability to distribute forces and to resist buckling when a push force is applied to the proximal end 8064 of the clot retrieval device. In some implementations the percentage change between the maximum rail width dimension and the minimum rail width dimension is between about 20.0% and about 35.0%. In other implementations the percentage change between the maximum rail width dimension and the minimum rail width dimension is between about 22.0% and about 27.0%. In an exemplary implementation the width dimension of the rail segments transitions from a maximum width dimension of about 0.0047±0.0004 inches to a minimum width dimension of about 0.0035±0.0004 inches.

Although FIG. 38 represents rail segments that are devoid of undulations, as previously described herein, it is appreciated that rail segments such as those shown in FIGS. 1A and 4A are also contemplated. Like the devices of FIG. 30 disclosed above, it is appreciated that other than the rail width characteristics disclosed in the preceding paragraph, any of a number of the features and/or characteristics of the vascular treatment devices described in conjunction with the devices of FIGS. 1-29 (e.g., dimensional, spatial, relational, etc.) may be incorporated into a clot retrieval device 8050 according to FIG. 38.

In some implementations the width of rails 8051 and/or 8052 taper along their length (or a portion thereof) in a substantial uniform and diminishing fashion. In some implementations discrete portions of the rails have a substantially uniform width dimension with only transitional tapers being used to join rail portions of different widths. In some implementations discrete portions of the rails have a substantially uniform width dimension with stepped transitions between rail portions of different widths. In other implementations two or more of the preceding width transitional methods are utilized. Although not required, it is preferable that the width transitions occur at portions along the rail struts other than at a junction of the struts (e.g., junctions 8070).

In some implementations, in a manner previously described, struts 8064 and 8065 of the most proximal cell structure also have an enhanced width dimension that may be equal to or less than the maximum rail width dimension for the purpose of enhancing the pushability of the clot retrieval device as it is advanced through the tortuous anatomy of a patient. In some implementations less than the entire length of struts 8064 and 8065 are provided with an enhanced width dimension. For example, in some implementations an enhanced width portion extends from a proximal most end of struts 8064 and 8065 and terminates a distance prior to their juncture. The configuration of struts 8064 and 8065 may also be altered in manners previously disclosed.

With continued reference to FIG. 38, in exemplary implementations all or portions of struts 8053 and 8054 (and optionally all or portions of struts 8055 and 8056) have width dimensions of about 0.0045 inches to about 0.0050 inches, all or portions of struts 8057 and 8058 (and optionally all or portions of struts 8055, 8056, 8059 and 8060) have width dimensions of about 0.0036 inches to about 0.0040 inches, all or portions of struts 8059 and 8060 (and optionally all or portions of struts 8061, 8062 and 8063) have width dimensions of about 0.0034 inches to about 0.0036 inches. In some implementations the remainder of the struts generally located in region P of the device have width dimensions of about 0.0027 inches, the struts generally located in region Q have width dimensions of about 0.0034 inches to about 0.0036 inches, and the struts generally located in region R have a width dimension of about 0.0031 inches to about 0.033 inches. In one or more of the immediately preceding implementations, the width dimension of struts 8064 and 8065 is between about 0.0036 inches and about 0.0047 inches. It is to be appreciated that the dimensions disclosed relate to exemplary implementations and are also subject to customary manufacturing tolerances. Variations in the dimensions are possible and contemplated.

Although not required, it is preferable that the width transitions occur at portions along the struts themselves other than at a junction of the struts (e.g., junctions 8070 and 8071).

As illustrated in FIG. 38, the strut density in the region generally identified by "Q" is notably less than the strut densities in the regions generally identified by "P" and "R". As a consequence, the cell structures 8080 generally located in region Q are of a larger size than the cell structures 8081 generally located in regions P and R. As previously discussed, an advantage of larger sized cell structures within the main body portion of the retrieval device is that it enhances clot integration into the main body portion (region Q) when a radial strength of the main body portion is properly provided. For the purpose of providing sufficient radial strength in region Q of the device, the struts generally located within region Q have an enhanced width dimension as compared to the cell struts generally located in region P (other than the struts 8053-8065) and the cell struts generally located in region R. In one implementation the width dimension of the struts in region Q are similar to or the same as the width dimension of the distal sections of rails 8051 and 8052 (e.g., struts 8061, 8062 and/or 8063).

In an exemplary implementation struts 8003-8006 and a proximal portion of struts 8055 and 8056 have a width dimension of about 0.0047 inches, struts 8057, 8058, and a distal and proximal portions of struts 8055,8056 and 8059,8060, respectively, have a width dimension of about 0.0040 inches, struts 8009, 8011 and a distal portion of strut 8010 have a width dimension of about 0.0034 inches, struts 8012-8013 have a width dimension of about 0.0040 inches, struts 8061, 8062, 8063 and the distal portions of struts 8059 and 8060 have a width dimension of about 0.0035 inches. In some implementations the remainder of the struts generally located in region P of the device have width dimensions of about 0.0027 inches, the struts generally located in region Q have width dimensions of about 0.0035 inches, and the struts generally located in region R have a width dimension of about 0.0031 inches. The increased width dimension of the struts in section R advantageously reduces the likelihood of struts buckling within the distal taper region of the clot retrieval device during its delivery to a treatment site of a patient. The increased width dimension also increases the radial strength of the distal taper region that enhances the ability of the distal taper region to remain open while the clot retrieval device is withdrawn from a patient so that it may sweep away remaining portions of the clot when the clot retrieval device is being withdrawn from the patient.

According to some implementations the clot retrieval devices 8050 according to FIG. 38 are laser cut from a tube having an inner diameter of about 3.77 millimeters and a wall thickness of between about 0.097 millimeters to about 0.131 millimeters. In use, a clot retrieval device 8050 according to an implementation of that shown in FIG. 38 is advanced through the tortuous vascular anatomy or bodily duct of a patient to a treatment site in an unexpanded or compressed state of a first nominal diameter and is movable from the unexpanded state to a radially expanded state of a second nominal diameter greater than the first nominal diameter for deployment at the treatment site. In alternative exemplary embodiments the second nominal diameter (e.g., average diameter of main body portion) is about 6.0±0.5 millimeters. In some implementation, the dimensional and material characteristics of the cell structures 8080 residing in the main body (section Q) are selected to produce sufficient radial force and contact interaction to cause the cell structures 8080 to engage with an embolic obstruction/clot residing in the vascular in a manner that permits partial or full removal of the embolic obstruction from the patient. In some implementation, the dimensional and material characteristics are selected to produce a radial force per unit length in the expandable portion of the retrieval device of between about 0.010 N/mm to about 0.020 N/mm when the diameter of the main body portion is reduced to about 5.0±0.5 millimeters.

In the implementations of FIG. 38, the cell structures generally located in regions P and R (excluding those that are formed at least in part by rail segments 8051 and 8052) are shown having similar shapes with the cell structures 8081 including a pair of short struts 8082 and a pair of long struts 8084. In an exemplary implementation the area of cell structures 8081 is about 9.2 mm². The cell structures 8080 generally located in region Q, in one implementation, comprise a shape consisting of two adjoining cell structures 8081 with a long strut 8084 being omitted between them. Although other types of large sized cell structures are contemplated, an advantage of the cell construction illustrated in FIG. 38 is that it possesses good nesting capability to permit the retrieval device to achieve a small delivery profile.

In some implementations the overall length of the expandable portion of the clot retrieval device is between about 65.0 millimeters and about 75.0 millimeters with the main body portion (section Q) having a length of between about 25.0 millimeters and about 35.0 millimeters. In one exemplary implementation the overall length of the expandable portion of the clot retrieval device is about 71.9 millimeters with the main body portion (section Q) having a length of about 32.3 millimeters and the proximal and distal taper regions having a length of about 22.5 millimeters and 17.1 millimeters, respectively.

Figure 39:
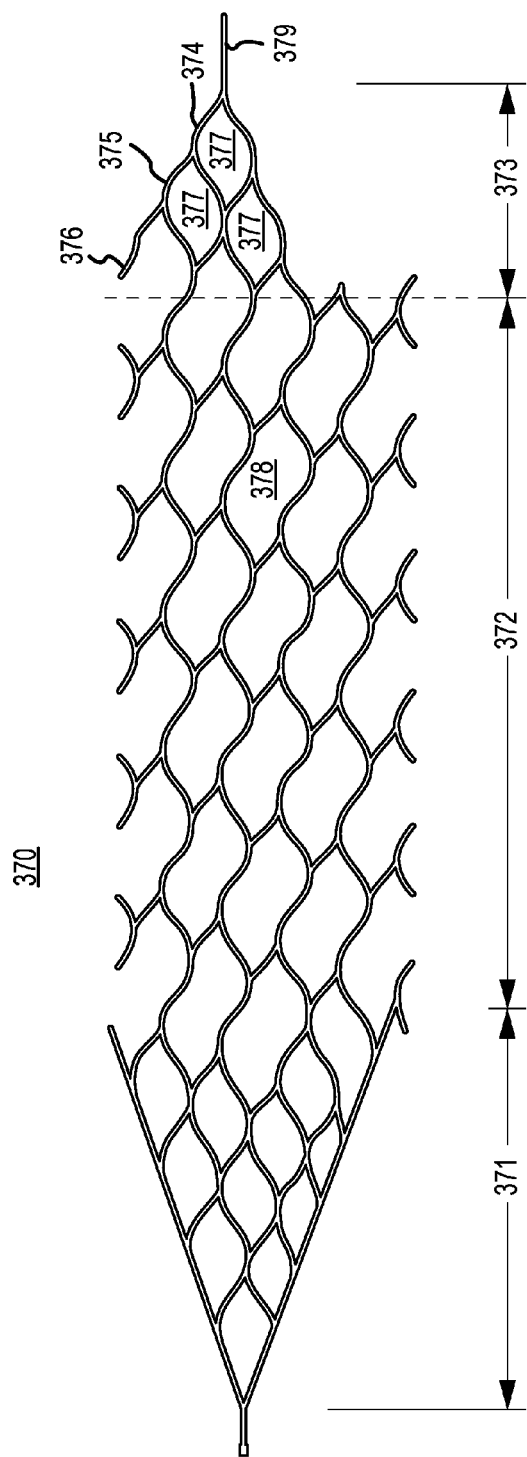
FIG. 39 illustrates a two-dimensional plane view of clot retrieval devices according some implementations.

FIG. 39 depicts a two dimensional view of a duct obstruction retrieval device 370 according to another implementation. As with some of the other implementations previously described, the retrieval device 370 comprises a proximal tapered end portion 371, a cylindrical main body portion 372 and a distal tapered end portion 373. A difference in the distal tapered end portion 373 as compared to the distal tapered end portions previously described is that the distal tapered end portion 373 has less than three full rows of cell structures so as to reduce the distal taper length. In the example of FIG. 39 the distal tapered end portion comprises two full rows of cell structures 374 and 375 and a partial row of cell structures 376. (For the sake of clarity, although row 375 in the implementation of FIG. 39 includes a single cell structure, it is in any case considered a row of cell structures.) The inclusion of a distal tapered end portion in the retrieval device that culminates into a distal antenna provides a number of advantages over retrieval devices that would otherwise terminate in a blunt end. One advantage is that once the retrieval device has been positioned and expanded in a vessel of a patient the tapered end provides a greater degree of placement adjustment over a retrieval device having a blunt end. Another advantage is that the distal tapered end portion is more atraumatic than a blunt end. The reduced taper length achieved by limiting the construction of the distal tapered end portion 373 to less than three full rows of cell structures has been found to advantageously result in a distal taper that is both more stable and more atraumatic than those having a greater number of full rows of cell structures. In retrievers having cell structures of different sizes, like those of cell structures 376 and 377, it is preferable that the full rows of cells in the distal tapered end portion 373 be comprised of substantially all small-sized cell structures 377 like that shown in FIG. 39.

According to some implementations the length of the distal tapered end portion 373 in the as-cut manufactured state is less than about 30% of the length of the main body portion 372, and preferably less than about 25% of the length of the main body portion 372. In one implementation the lengths of the main body portion 372 and the distal tapered end portion 373 are about 26 mm and 6 mm, respectively. In another implementation the distal tapered end portion 373 has a length of between about 4.5 mm to about 5.0 mm. According to some implementations the combined length of the distal tapered end portion 373 and the distal antenna 379 is less than about 10 mm.

Figure 40A:
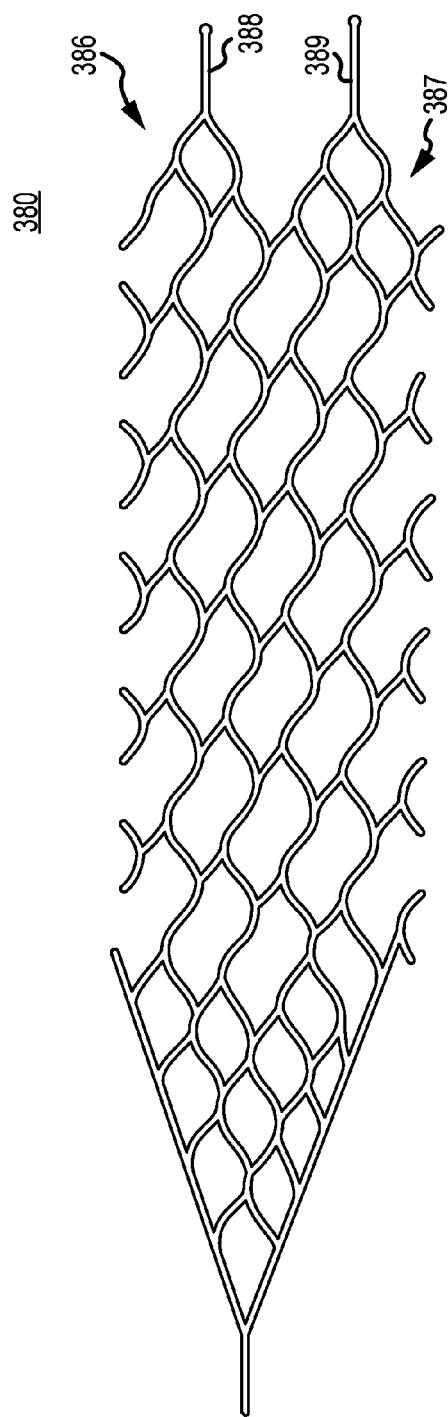
FIG. 40A illustrates a two-dimensional plane view of a clot retrieval device according to one implementation.
Figure 40B:
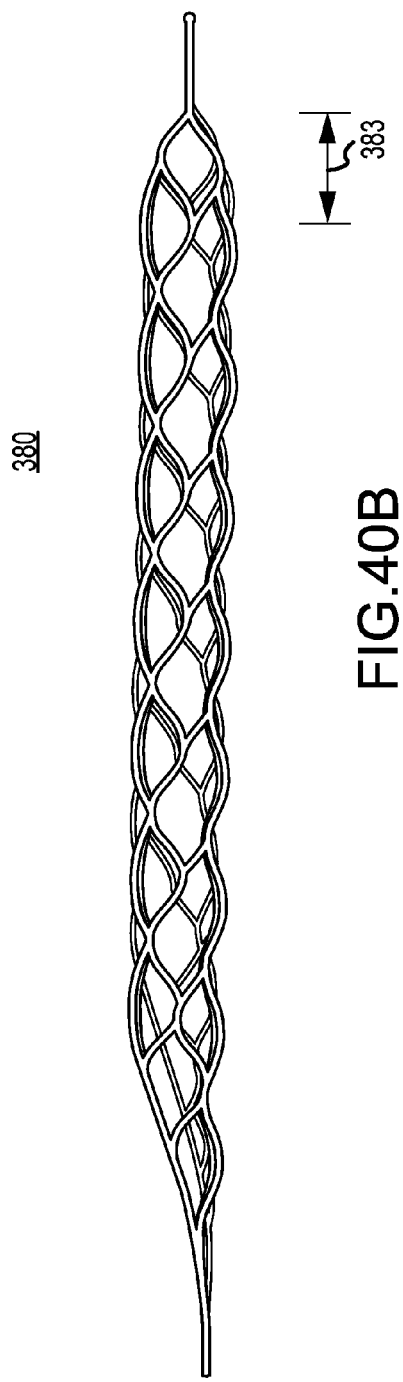
FIG. 40B illustrates a three-dimensional view of the clot retrieval device of FIG. 40A.

FIG. 40A shows a two dimensional view of a duct obstruction retrieval device 380 according to another implementation. Like the retrieval device 370 shown in FIG. 39, retriever 380 comprises a distal tapered end portion comprising less than three full rows of cell structures. Retriever device 380 differs from retriever 370 in that the distal tapered end portion comprises cell structures that are bifurcated into a first set of cell structures 386 and a second set of cell structures 387 with the first cell of cell structures 386 terminating at a first distal antenna 388 and the second set of cell structures 387 terminating at a second distal antenna 389. FIG. 40B depicts a three dimensional view of retrieval device 380 with the reference number 383 denoting the distal tapered end portion of the device. As shown in FIG. 40B, distal antenna 388 and distal antenna 389 are joined to form a retrieval device having a distal tapered end portion with a closed end.

It is important to note that although the retrieval devices 370 and 380 have been described as comprising distal antennas, in other implementations like retrieval devices are provided without distal antennas. The same applies to each of the implementations disclosed and contemplated herein. In addition, with reference to the retrieval device 380 of FIG. 40, in another implementation only a single distal antenna is provided that is chosen between distal antenna 388 and distal antenna 389. In such an implementation the retrieval device would possess an open distal end with the second set of cell structures 387 being available to sweep along the treatment vessel to capture dislodged material.

Figure 41:
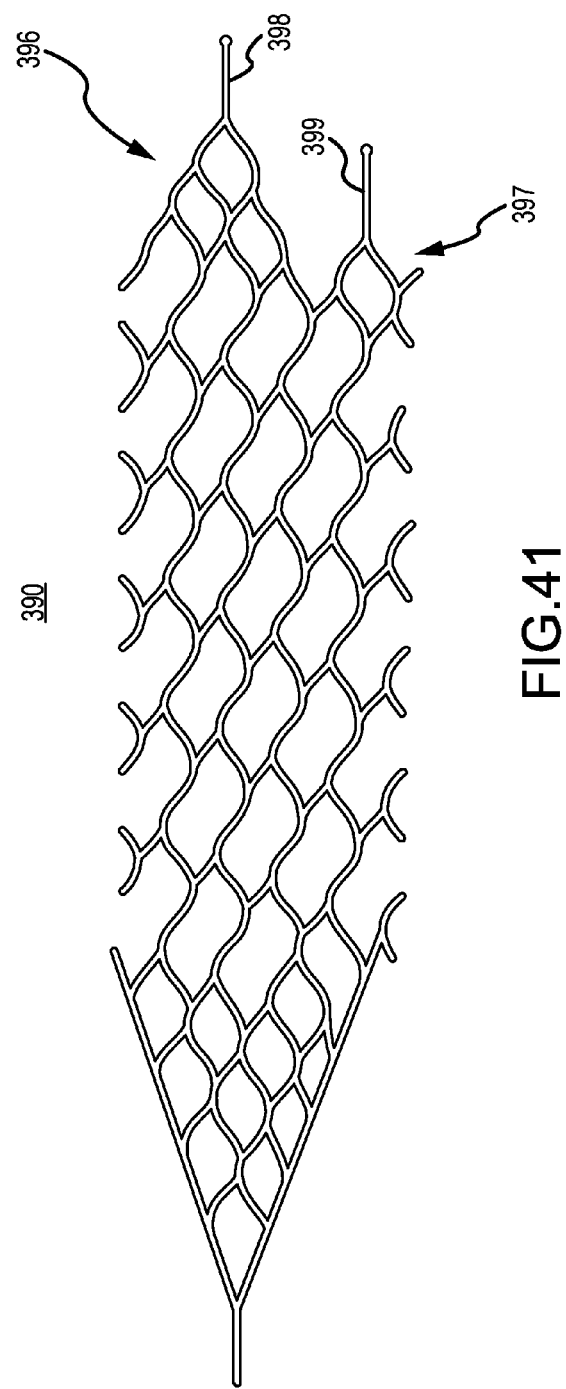
FIG. 41 illustrates a two-dimensional plane view of clot retrieval devices according some implementations.

FIG. 41 is a two dimensional view of a duct obstruction retrieval device 390 according to another implementation that comprises a distal tapered end portion comprising less than three full rows of cell structures. Like retrieval device 380, the distal tapered end portion of retrieval device 390 has cell structures that are bifurcated into a first set of cell structures 396 and a second set of cell structures 397 with the first cell of cell structures 396 terminating at a first distal antenna 398 and the second set of cell structures 397 terminating at a second distal antenna 399. As shown in FIG. 41, the first and second distal antennas 398 and 399 are longitudinally off-set from one another. In one implementation a radiopaque material, feature (e.g., flared strut) or component (e.g., a coil) is positioned on each of the first and second antennas. By virtue of there off-set construction, a radiopaque component, for example, on each of the antennas enables the distal end of the retrieval device and the distal tapered end portion of the retrieval device to be visually delineated during the treatment procedure.

Figure 42A:
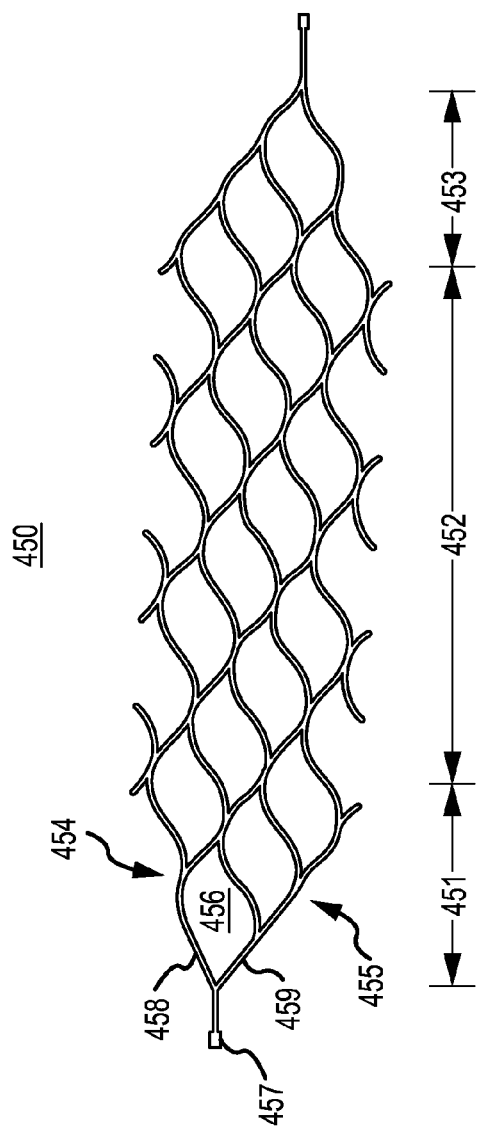
FIG. 42A illustrates a two-dimensional plane view of clot retrieval devices according some implementations.

FIG. 42A is a two dimensional view of a duct obstruction retrieval device 450 according to another implementation. The retrieval device 450 comprises an expandable member that has a proximal tapered end portion 451, a cylindrical main body portion 452 and a distal tapered end portion 453. The outer-most cell structures in the proximal tapered end portion have outer wall segments that form first and second rail segments 454 and 455, respectively. Each of the rail segments 454 and 455 extend from a proximal-most end of the expandable member to a position at or near the proximal end of the cylindrical main body portion 452. In the implementation of FIG. 42, each of the rail segments 454 and 455 are undulating. A proximal antenna 457 extends proximally from a proximal-most cell structure 456.

Figure 42B:
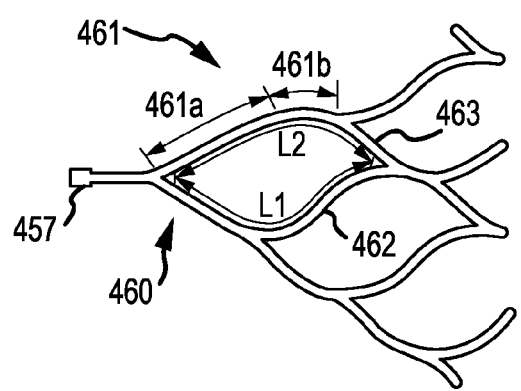
FIG. 42B illustrates an enlarged two-dimensional plane view of the proximal tapered end portion of the retriever device depicted in FIG. 45A.

The proximal-most cell structure 456, as shown in greater detail in FIG. 42B, comprises first and second outer struts 460 and 461, respectively, and first and second inner struts 462 and 463, respectively. As shown in the layout of FIG. 42B, the first outer strut 460 and a first portion 461a of the second outer strut 461 are straight in the two dimensional layout while the first inner strut 462, second inner strut 463 and the second portion 461b of strut 461 are curvilinear in the two dimensional layout. In the manufactured, three dimensional configuration the first outer strut 460 and the first portion 461a of the second outer strut 461 are curved and devoid of undulations. As a result of being oriented at the proximal end of the expandable member and being co-extensive to the proximal antenna, the straight strut segments of the proximal-most cell structure 456 enhance the pushability of the retrieval device 450 as it is delivered through the anatomy of a patient as compared to retrieval devices having proximal-most cell structure with only curved struts in the two dimensional layout.

In some implementations, the total length of struts 460 and 462 (L1) and the total length of struts 461 and 463 (L2) are substantially the same in order to promote a nesting of the struts when the expandable member transitions from the expanded state to the unexpanded state. According to some implementations the difference in length between L1 and L2 is less than 5.0%, while in other implementations the difference in length between L1 and L2 is less than 1.0%.

Figure 43:
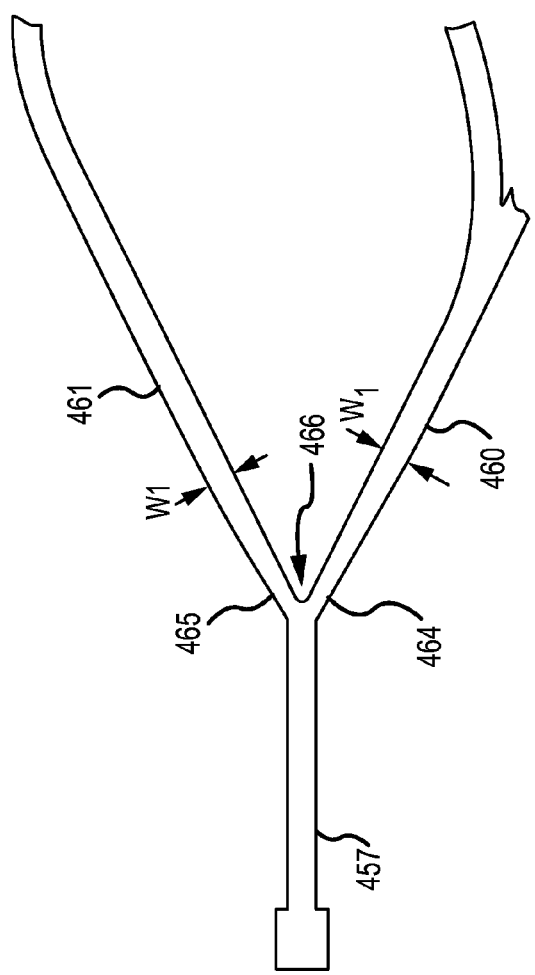
FIG. 43 illustrates a two-dimensional plane view of a proximal-most cell structure according some implementations.

FIG. 43 illustrates a variation of the proximal-most cell structure 456. As depicted, each of struts 460 and 461 have an area of reduced width 464 and 465, respectively, that are located adjacent their junction 466 with the proximal antenna 457. The inclusion of the reduced width areas 464 and 465 locally enhances the proximal-most cell structure's ability to collapse by reducing the amount of force needed to initiate and effectuate the collapse. Thus, for example, when the retrieval device 450 is first introduced into an introducer sheath for placement within a delivery catheter or is withdrawn into a delivery catheter after the expandable member has deployed inside a patient, the areas of reduced width 464 and 465 cause the struts 460 and 461 to be more easily folded in the area of the junction 466 with less force than would otherwise be required absent the areas of reduced width. This makes the retrieval device 450 more manageable when being handled by healthcare professionals when the retrieval device 450 is being introduced into the delivery catheter for the first time, thus reducing the likelihood of the retrieval device being damaged during the introduction process. As previously discussed, after the retrieval device 450 has been introduced and expanded inside the duct of a patient there may be occasions when the retrieval device is proximally withdrawn back into the delivery catheter. This may occur, for example, upon the retrieval device being improperly placed in the duct or upon the completion of a retrieval procedure. In each of these instances because less force is required to collapse the expandable member of the retrieval device several advantages are realized. One advantage is that it reduces the likelihood of the retrieval device 450 acting upon the delivery catheter in a manner that would cause an inadvertent displacement of the delivery catheter within the duct of the patient. Another advantage is that it reduces the likelihood of excessive force being applied at the attachment between the proximal antenna 457 and the elongate wire (e.g. elongate wire 40 shown in FIG. 1A) that would result in a failure at the junction.

In the implementation of FIG. 43 the areas of reduced width 464 and 465 comprise tapers. In other implementations the areas of reduced width are denoted by a stepped reduction in strut width. The amount by which the width is reduced in areas 464 and 465 will vary according to the nominal widths of struts 460 and 461. In any event, it is important that the amount of width reduction is consistent with the radial force and structural integrity requirements of the expandable member. It has been discovered that a reduction of width in the as-cut manufactured state of between about 5.0% and about 20.0% is suitable for struts having a nominal width of between about 0.0057 inches and about 0.0027 inches, with a preferable range being between about 10.0% and about 20.0% in width reduction. In one implementation the width dimension W1 of struts 460 and 461 is about 0.0053 inches with the minimum width dimension of the areas of reduced width being 0.0047 inches. In another implementation the width dimension W1 of struts 460 and 461 is about 0.0057 inches with the minimum width dimension of the areas of reduced width being 0.0046 inches.

In some implementations the as-cut width dimensions of struts 460 and 461 are different, with the width dimension of their respective areas of reduced width 464 and 465 also being different. For example, in one implementation strut 460 has a width dimension of about 0.0050 inches, strut 461 has a width dimension of about 0.0057 inches, and areas of reduce width 464 and 465 have width dimensions of about 0.0042 inches and about 0.0046 inches, respectively.

Figure 44:
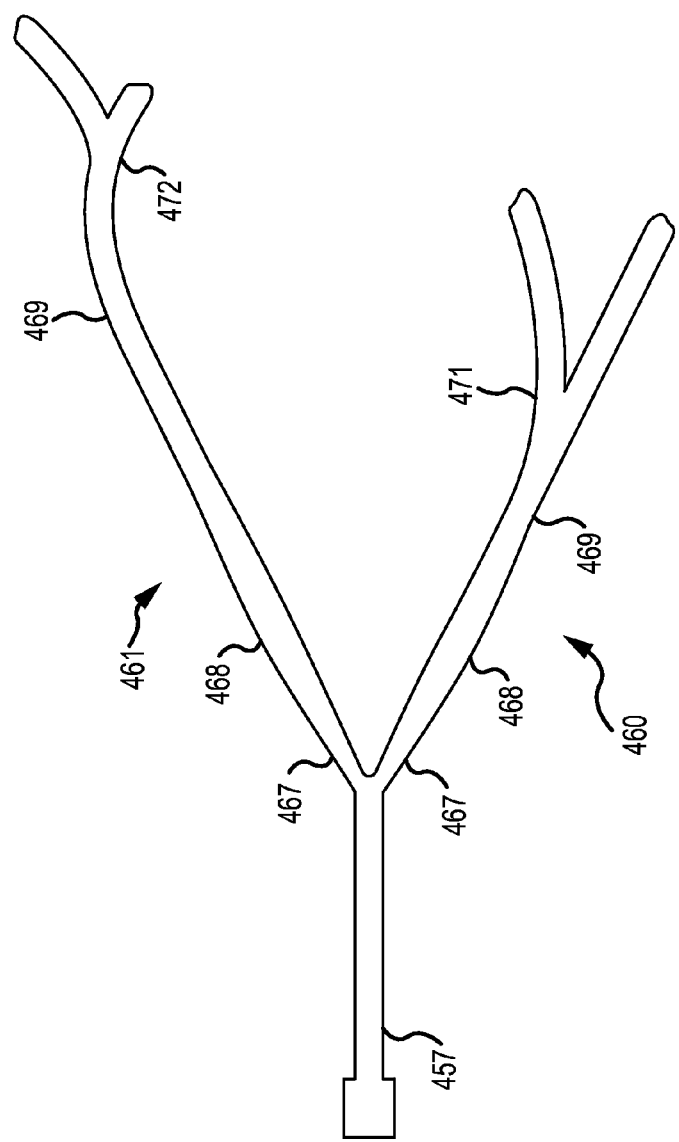
FIG. 44 illustrates a two-dimensional plane view of a proximal-most cell structure according some implementations.

FIG. 44 shows another variation of the proximal-most cell structure 457 wherein outer struts 460 and 461 comprise a proximal section 467, a midsection 468 and a distal section 469. Because the width dimensions of the outer struts 460 and 461 of the proximal-most cell structure 456 are generally made greater than most of struts in the remaining portion of the retrieval device 450 for the purpose of enhancing the pushability of the expandable member, the bulk of material at the junctures 471 and 472 located at the distal end of the struts may impede the expandable member's ability to collapse. For this reason, in the implementation of FIG. 44 the distal sections 469 have a reduced width dimension in order to reduce the amount of material occupying the juncture regions 471 and 472. Although FIG. 44 also shows the proximal sections 467 having a reduced width dimension (similar to that described above), in some implementations this is not the case. In a manner described above, the sections of reduced width may comprise tapers and/or steps.

Another advantage of the implementation depicted in FIG. 44 is that the midsection 468 of struts 460 and 461 may be provided with a sufficient width to enhance the visibility of the device under fluoroscopy without materially impacting the ability of the proximal end of the proximal tapered region 451 to collapse or to otherwise assume its unexpanded state. According to one implementation the width dimension of the strut midsections 468 is about 0.0053 inches and the minimum width dimension of the proximal and distal sections 467 and 469 being 0.0047 inches and 0.0041 inches, respectively. As with some of the FIG. 43 implementations, in some FIG. 44 implementations the width dimensions of struts 460 and 461 are different, with the width dimension of one or more of their respective proximal sections, midsections and distal sections being different.

FIG. 45A is a two dimensional view of a duct obstruction retrieval device 800 according to another implementation. The retrieval device 800 comprises an expandable member that has a proximal tapered end portion 801, a cylindrical main body portion 802 and a distal tapered end portion 803. The outer-most cell structures in the proximal tapered end portion have outer wall segments that form on one side a non-undulating rail segment 804 and on the other side an undulating rail segment 805. Each of the rail segments 804 and 805 extend from a proximal-most end of the expandable member to a position at or near the proximal end of the cylindrical main body portion 802. A proximal antenna 806 extends proximally from a proximal-most cell structure 807 while a distal antenna 808 extends distally from the distal end of distal tapered section 803. The distal tapered section 803 is similar to that described above in conjunction with FIG. 39. In some implementations the proximal-most cell structure 807 has the same features and characteristics as proximal-most cell structure 456 in the implementations of FIGS. 42-44 above.

As a result of the diagonal disposition of the cell structures in the retrieval device, the straight line length along which rails 804 and 805 pass are different in the as-cut manufactured state with the straight line length that passes along rail 804 being longer than the straight line length that passes along rail 805. The linear configuration of rail 804 in combination with the undulating configuration of rail 805 advantageously results in the rails 804 and 805 having lengths that more closely approach one another when the retrieval device assumes it's unexpanded/delivery state. According to one implementation, rails 804 and 805 are configured to achieve substantially the same length when the retrieval device 800 is in the unexpanded/delivery state. In some implementations, the difference in length between rails 804 and 805 is between about 0% to about 5% when the retrieval device 800 is in the unexpanded/delivery state.

Figure 45B:
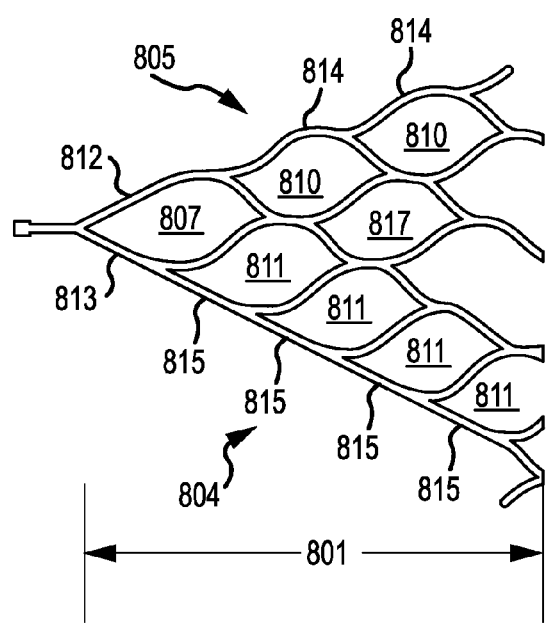

As discussed earlier, the retrieval devices disclosed and contemplated herein are generally laser cut from a tube and in their actual three dimension configuration generally comprise tube like structures. FIG. 45, like many of the other figures, represents a retrieval device as it would appear in a two dimension layout, that is, as if it were cut along its length and laid out on a flat surface. With this in mind, and with reference to FIG. 45B, in the two dimension layout the cell structures are polygons comprising a plurality of struts. As shown, rail segments 804 and 805 are constructed by the outer walls of the outer most cell structures 807, 810 and 811 in the proximal tapered section 810. Undulating rail segment 805 is formed by a first outer wall 812 of the proximal-most cell structure and the outer walls 814 of outer cell structures 810, whereas the non-undulating rail segment 804 is formed by a second outer wall 813 of the proximal-most cell structure and the outer walls 815 of outer cell structures 811. As represented in FIG. 45B, in the two dimension layout the outer walls 814 are curvilinear and the outer walls 815 are straight. As will be appreciated, when in the tubular form, the rail 804 will be curved when the expandable member assumes an expanded state, but will nonetheless be devoid of undulations. Rail 805 will also assume an additional degree of curvature in its three dimensional state, but unlike rail 804 will comprise undulations.

An advantage of the proximal tapered section 801 design is that the non-undulating rail segment 804 provides the aforementioned benefits related to pushability and kink resistance, while the undulating rail segment 805 accommodates the inclusion of a larger number of symmetric-shaped polygons and/or nearly symmetric-shaped polygons within the section 801. The inclusion of an increased number of symmetric-shaped and/or nearly symmetric-shaped polygons in the distal tapered end portion 801 improves its ability to assume it's unexpanded or compressed state and also provides for a more uniform and compact configuration. Because symmetrically shaped cell structures have better nesting tendencies than their non-symmetric counter-parts, the aforementioned advantages are achieved, at least in part, by the increased number of symmetrically shaped cell structures disposed within the proximal tapered end portion 801.

Another advantage of a proximal tapered end portion having one non-undulating rail segment 804 and one undulating rail segment 805 is that the inclusion of the undulating rail segment provides more freedom in the design of the cell structures within the proximal tapered end portion as opposed to a design having two non-undulating rails. As shown in FIG. 45B, the outer cell structures 811, along which the non-undulating rail segment 804 is formed, comprise structures that are considerably more symmetric than those, like for example, shown in FIG. 30.

Figure 45C:
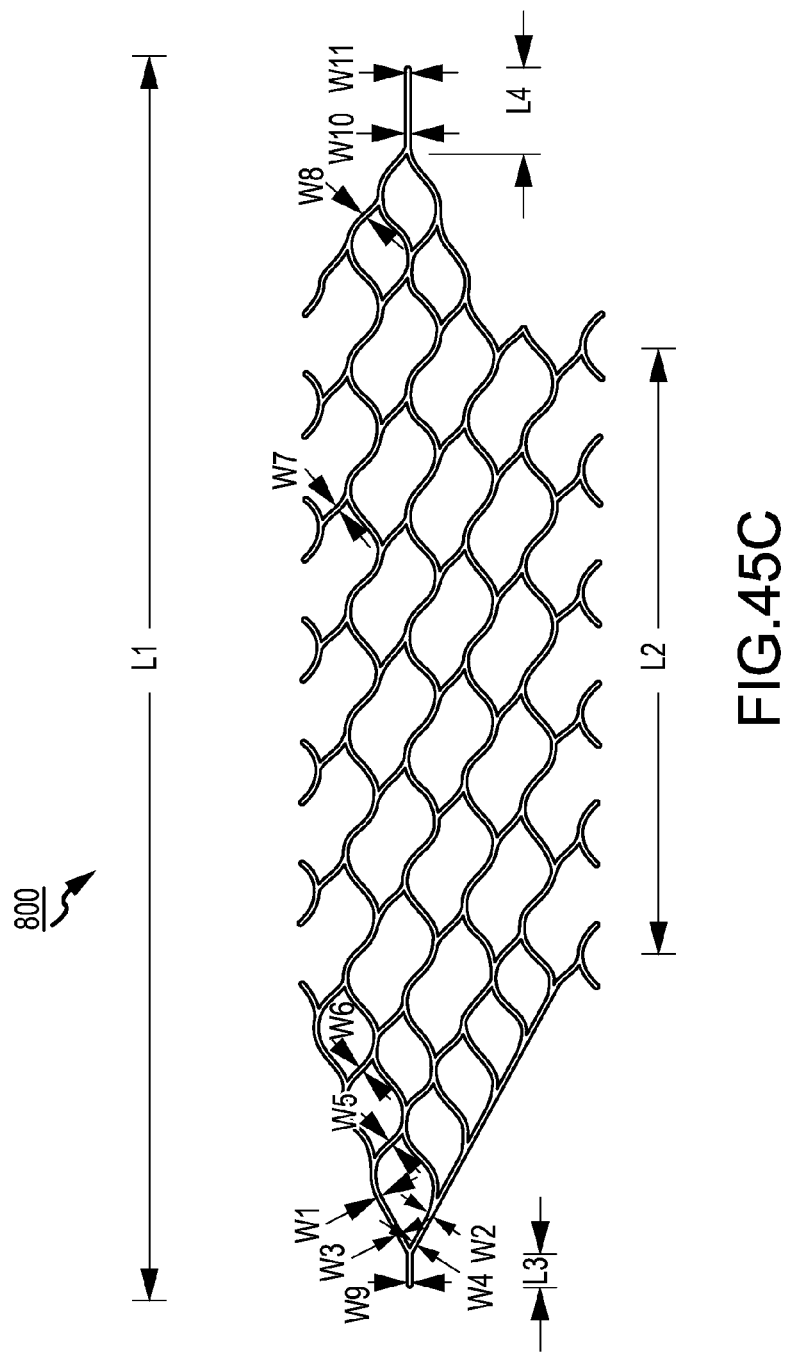

With reference to FIG. 45C, according to one implementation the retriever device 800 has the following as-cut dimensional characteristics: L1=56.44 mm±0.50 mm; L2=26.85 mm±0.50 mm; L3=2.0 mm±0.1 mm; L4=4.0 mm±0.3 mm; W1=0.0054 inches ±0.0004 inches; W2=0.0056 inches ±0.0004 inches; W3=0.0047 inches ±0.0004 inches; W4=0.0047 inches ±0.0004 inches; W5=0.0040 inches ±0.0004 inches; W6=0.0027 inches ±0.0004 inches; W7=0.0034 inches ±0.0004 inches; W8=0.0031 inches ±0.0004 inches; W9=0.010 inches ±0.007 inches; W10=0.0035 inches ±0.0004 inches; W11=0.0025 inches ±0.0004 inches. In one implementation the length of the proximal tapered end portion and the distal tapered end portion is about 13 mm and 7 mm, respectively.

Figure 46:
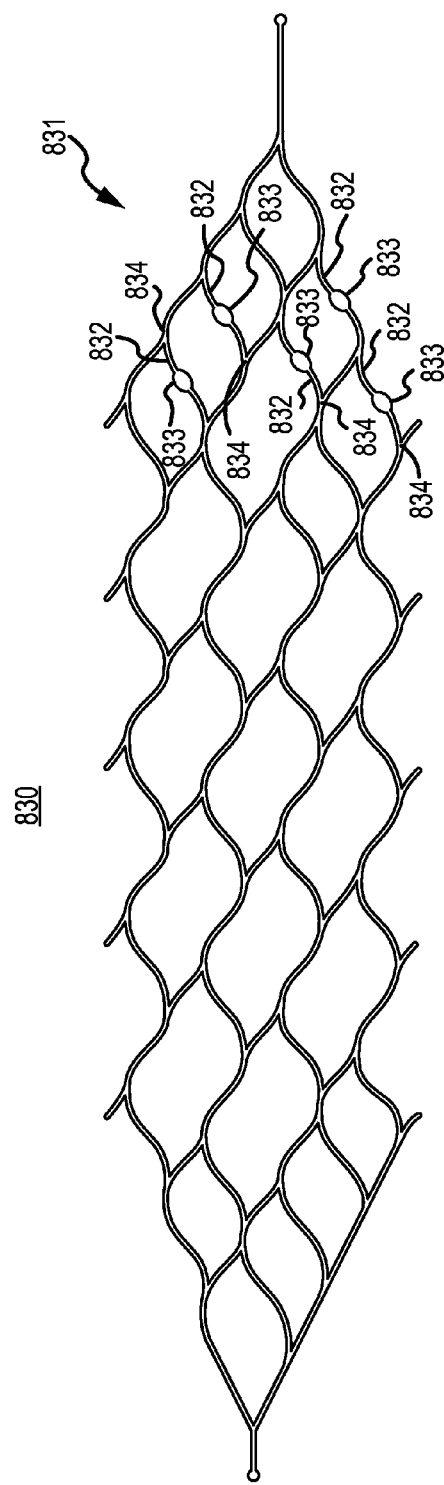
FIG. 46 illustrates a two-dimensional plane view of clot retrieval devices according some implementations.

FIG. 46 illustrates an obstruction retrieval device 830 according to another implementation wherein portions 833 of some struts 832 in the distal tapered end portion 831 of the retriever device are flared to enhance the radiopacity of the distal region of the device. In some implementations during manufacture each of portions 833 are laser cut so as to possess an enhanced width dimension with respect to the remainder of strut 832. Besides in themselves enhancing radiopacity, the flared portions (or portions of enhanced width) provide a good platform for receiving a radiopaque coating such as, for example, a gold coating. In the implementation of FIG. 46 the flared portions 88 are positioned a sufficient distance from the strut junctions 834 so as to not interfere with the retriever's ability to compress. In the implementation of FIG. 46 the flared portions 833 are also longitudinally staggered so that when the retriever 830 is in the compressed state no more than a single flared portion 833 will occupy a longitudinal position. Such a configuration lessens the impact the flared portions 833 may have on the retriever's lowest achievable diameter dimension along the distal tapered end portion 831. In the embodiment of FIG. 46, the flared portions comprise nodes which in one implementation have a diameter of about 0.015 inches. In other embodiments the flared portions 833 are longitudinal in nature and occupy a substantial length of the struts 832. In such implementations the flared portions 833 may have a width of between about 0.0035 inches to about 0.0045 inches.

Figure 47A:
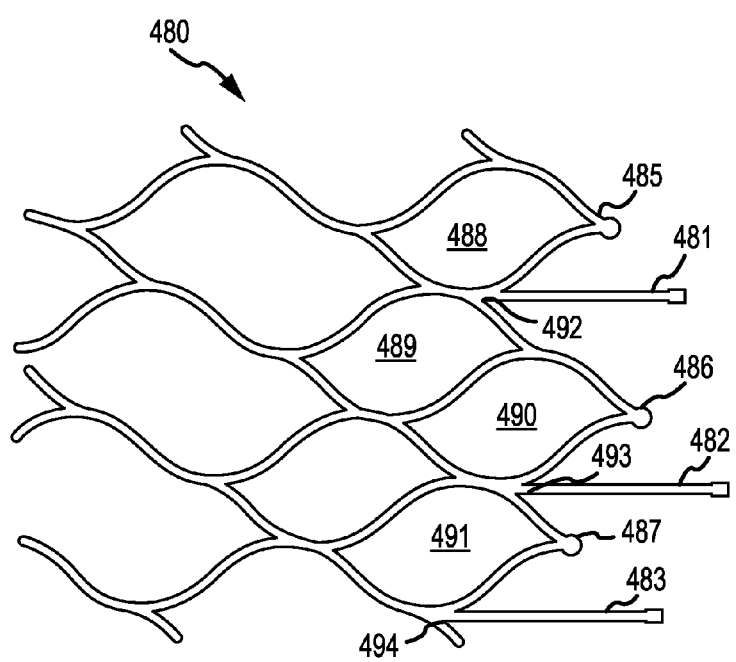
FIG. 47A illustrates a two-dimensional plane view of a distal end of clot retrieval devices according some implementations.
Figure 47B:
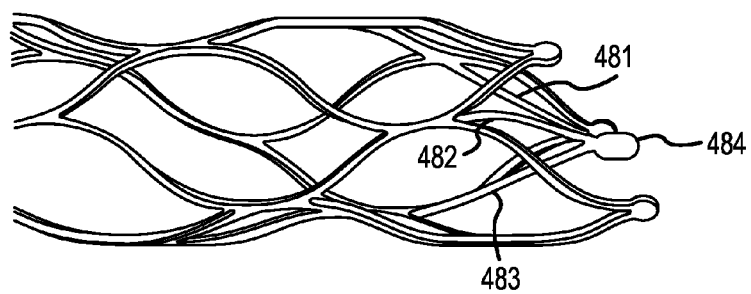
FIG. 47B illustrates a three-dimensional view of the distal end depicted in FIG. 47A.

FIGS. 47A and 47B illustrate a distal segment of an obstruction retrieval device 480 according to one implementation. FIG. 47A depicts the device 480 in a two-dimensional layout as if it were cut along its length and laid out on a flat surface. While FIG. 47A depicts the device 480 in its as-cut configuration, the three-dimensional representation of FIG. 47B shows the device 480 in a post-cut manufactured state.

With reference to FIG. 47A, the distal segment of device 480 comprises a plurality of distal cell structures 488-491 with a set of antennas 481, 482 and 483 extending distally from the juncture regions 492-494 of cell structures 488-491. In some implementations tabs 485-487, or other enhanced dimension features, are provided at one or more ends of the distal most cell structures for the purpose of identifying the distal end of the device under fluoroscopy by virtue of their enhanced dimensional characteristics and/or as a result of being endowed with a radiopaque material. As shown in FIG. 47A, in some implementations the distal-most cell structures are smaller than the adjacent cell structures in the main body portion of the device 480.

As shown in FIG. 47B, at a point in time after the device 480 has been formed, such as being cut by a laser, the distal ends of antennas 481, 482 and 483 are joined together at the juncture 484 so as to provide the internal cavity of device 480 with a closed-end. In effect, the closed-end forms a basket that facilitates the collection of particulates, such as embolic material, that may become dislodged during a retrieval procedure. In some implementations the juncture 484 is formed by soldering together the distal ends of the antennas 481-483. In some implementations the distal ends of the antennas 481-483 are positioned within an encasement, such as a coil spring or other perforated structure, with a solder or other bonding agent being applied within and/or about the encasement to effectuate a bonding together of the distal ends of the antennas 481-483. In some implementations the encasement comprises a rounded atraumatic distal tip. In some implementations the encasement comprises a radiopaque material.

Figure 48A:
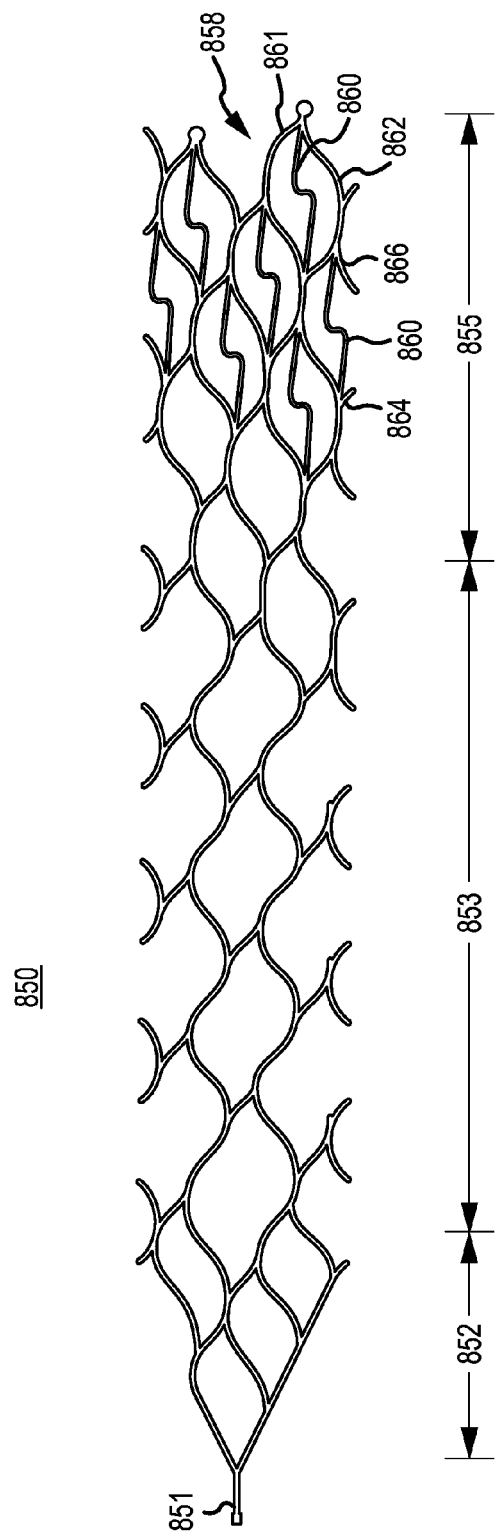
FIG. 48A illustrates a two-dimensional plane view of clot retrieval devices according some implementations.
Figure 48B:
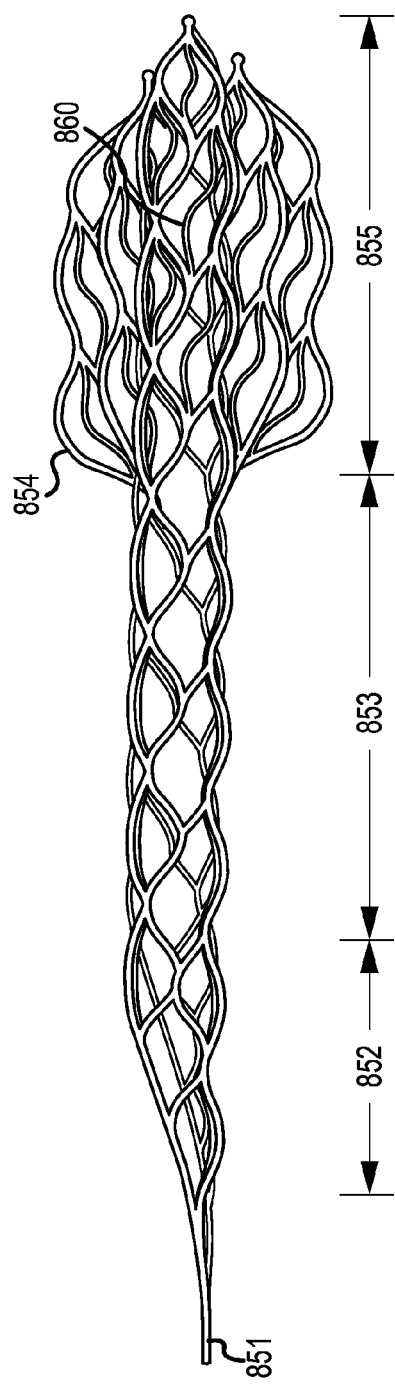
FIG. 48B illustrates a three-dimensional view of the clot retrieval device depicted in FIG. 48A.

FIGS. 48A and 48B illustrate an obstruction retrieval device 850 according to one implementation. FIG. 48A depicts the device 850 in a two-dimensional layout as if it were cut along its length and laid out on a flat surface. While FIG. 48A depicts the device 850 in its as-cut configuration, the three-dimensional representation of FIG. 48B shows the device 480 in a post-cut manufactured state. The device includes a proximal antenna 851, a proximal taper portion 852, a main body portion 853 and a distal portion 855. In the as-cut manufactured state the main body portion 853 and the distal portion 855 have the same, or substantially same, diameter. At a point in time after the device 850 has been cut, such as by laser cutting, the device 850 is formed so that the unconstrained configuration of the distal portion 855 has a diameter that is greater than that of the unconstrained main body portion 853. The post as-cut form of the device 850 may be achieved with the use of mandrels or other tools and methods known in the art. In some implementation the ratio of the unconstrained diameter of the distal portion 855 (absent the transition portion 854) and the main body portion 853 is between about 1.2/1.0 and about 2.0/1.0. For example, according to one implementation the average unconstrained diameter of the main body portion 853 is about 2.0 millimeters and the average unconstrained diameter of the distal portion 855, absent the transition portion 864, is about 4.0 millimeters. According to some implementations the ratio of the unconstrained length of the distal portion 855 (absent the transition portion 854) and the unconstrained length of the main body portion is between about 0.2 to about 0.7. For example, according to one implementation the unconstrained length of the main body portion 855 is between about 15 to 25 millimeters and the unconstrained length of the distal portion (absent the transition portion 854) is between about 5 to 10 millimeters.

According to some implementations, as depicted in FIG. 48A, the cell structures in the main body portion 853 are larger in size than those in the distal portion 855. The lower strut density in the main body portion 853 facilitates an integration of the retrieval device 850 within an obstruction. The higher strut density in the distal portion 855 facilitates the entrapment of dislodge particles as discussed in more detail below. Additionally, in some implementations the retrieval device is constructed in a manner that results in a radial force being exerted by the main body portion 853 that is greater than the radial force exerted by the distal portion 855 when the retrieval device 850 is deployed within a duct of a patient. In such an implementation, the main body portion 853 is situated to capture an obstruction while the distal portion 855 more gently acts against a wall of the duct distal to the obstruction to entrap portions of the obstruction that become dislodged during and after its capture. As such, according to one method the retrieval device 850 is placed at the treatment site of a patient by use of a delivery catheter, as previously disclosed herein. The retrieval device 850 is positioned at a distal end of the delivery catheter so that the main body portion 853 is positioned at the site of the obstruction to be retrieved. When sheathed within the delivery catheter the main body portion 853 and the distal portion 855 have the same, or substantially the same, diameter. Thereafter, the delivery catheter is withdrawn proximally to cause the constrained retrieval device to expand at the treatment site so that the main body portion 853 is at least partially forced into the obstruction and so that at least a portion of the distal portion 855 more gently rests against the duct wall distal to the obstruction. Upon the obstruction being captured within the main body portion 853 of device 850, the device may be removed from the patient in a manner consistent with one or more of the methods previously disclosed herein. During such removal, as the retrieval device is pulled proximally the distal portion 855 sweeps along the duct wall to entrap portions of the obstruction that may have become dislodged. By virtue of its enhanced diametric dimension, the distal portion 855 maintains contact with the duct wall during all or a portion of the removal procedure.

As discussed above, a lower strut density in the main body portion 853 facilitates an integration of the retrieval device 850 within an obstruction. However, in some implementations the retrieval device is constructed in a manner that results in a radial force being exerted by the main body portion 853 that is greater than the radial force exerted by the distal portion 855 when the retrieval device 850 is deployed within a duct of a patient. To achieve this variation in a radial force, in some implementations the width dimension of the struts in the main body portion 853 of the retrieval device are cut to have a larger width dimension of at least some or all of the struts in the distal portion 855.

As shown in FIGS. 48A and 48B, in some implementations the strut density in the distal segment 855 is further enhanced by the inclusion of non-linear struts 860 in at least some of the cell structures. In some implementations the non-linear struts extend between the proximal end 864 and distal end 866 of cell structures. In some implementations the non-linear struts 860 extend between the proximal end 864 and distal end 866 of cell structures with the non-linear strut 861 having substantially the same length as the upper strut 861 and/or lower strut 862 in the as-cut configuration. Such a construction enhances the ability of the cell structure struts to nest resulting in a lower achievable constrained diameter of the retrieval device. In some implementations the non-linear struts 861 extend between the proximal end 864 and distal end 866 of cell structures with the upper, lower and non-linear struts 860, 862 and 861, respectively, having substantially the same length in the as-cut configuration. So as not to greatly impact the radial force produced in the distal segment 855, in some implementations the non-linear struts 860 have a width dimension less than the width dimension of the upper and lower struts 861 and 862. In some implementations the ratio of the width dimension of struts 860 and the width dimension of each of the upper and lower struts 861 and 862, respectively, is between about 0.70 and 0.80. For example, according to one implementation each of the upper and lower struts, 361 and 362, have a width dimension of about 0.0035 inches while strut 360 has a width dimension of about 0.0025 inches.

Figure 49:
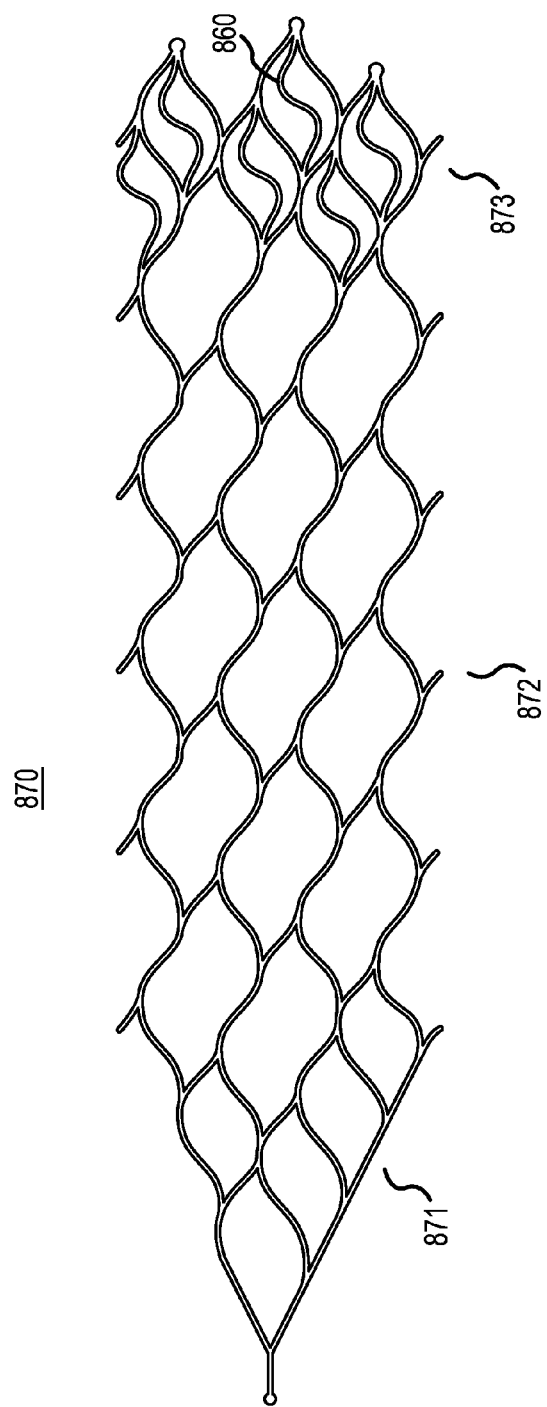
FIG. 49 illustrates a two-dimensional plane view of clot retrieval devices according some implementations.

FIG. 49 illustrates a variation to the as-cut configuration shown in FIG. 48A. As shown in FIG. 49, the retrieval device 870 comprises a proximal distal portion 871, a main body portion 872 and a distal portion 873, the distal portion being shorter in length than that depicted in FIG. 48A.

Figure 50:
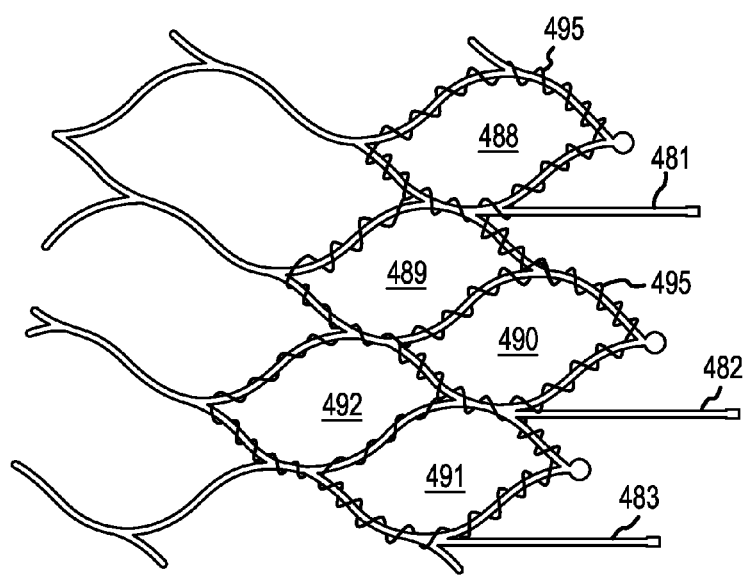
FIG. 50 illustrates a two-dimensional plane view of distal segment of a retrieval device according some implementations.

FIG. 50 illustrates a distal segment of a retrieval device similar to that shown in FIGS. 47A and 47B having one or more radiopaque wires or ribbons 495 wound about the struts that form cell structures 488-492. Throughout the remainder of the disclosure the term "wire" is used broadly to include wires, ribbons, or like structures. Although the entirety of the cell struts that form cell structures 488-492 may be wound with one or more radiopaque wires 495 as shown in FIG. 50, in other implementations only a selected number of struts may possess radiopaque wire windings. An advantage of incorporating the radiopaque wire windings into the distal segment of the retrieval device is that it enhances the visibility of the distal end of the device under fluoroscopy. In addition, when a sufficient number of distal member struts are endowed with wire windings, such as shown in FIG. 50, the wire windings enhance the stiffness of the distal segment. An advantage of increasing the stiffness of the distal segment is that it inhibits prolapse of the distal segment as the retrieval device is advanced through a delivery catheter or treatment duct of a patient. In one implementation the one or more wires comprise platinum. However, it is to be appreciated that any of a number of other radiopaque materials may be used. The one or more wires may comprise a core structure, such as stainless steel, that is clad or otherwise coated with a radiopaque material. The one or more wires may also comprise a polymeric structure impregnated, doped or otherwise coated with a radiopaque material. In some implementations the cross-sectional area of the one or more wires varies to provide a variation in radiopacity and/or stiffness within the distal segment. In some implementations the diameter or width dimension of the one or more wires 495 is in the range of between about 20% to about 50% less than the width dimension of the struts which form the distal segment.

Although not shown in FIG. 50, in some implementations small recesses are provided in at least some of the struts of cell structures 488-492 for the purpose of guiding the placement of the wire windings to designated locations. Preferably, the recesses are sized to receive only a portion of the wire so that only a portion of the wire resides within the recess and a portion of the wire resides outside the recess.

FIGS. 51A through 51D illustrate other aspects of a clot retrieval device 550 which are in some ways similar to the retrieval device 850 depicted in FIGS. 48A and 48B. FIGS. 51A-51D depict the device 550 in a two-dimensional layout as if it were cut along its length and laid out on a flat surface. The device includes a proximal antenna 561, a proximal taper portion 551, a main body portion 552a and a distal portion 552b. In the as-cut manufactured state the main body portion 552a and the distal portion 552b have the same, or substantially same, diameter. At a point in time after the device 550 has been cut, such as by laser cutting, the device 550 is formed so that the unconstrained configuration of the distal portion 552b has a diameter that is greater than that of the unconstrained main body portion 552a. The post as-cut form of the device 550 may be achieved with the use of mandrels or other tools and methods known in the art. In some implementation the ratio of the unconstrained diameter of the distal portion 552b and the main body portion 552a is between about 1.2/1.0 and about 2.0/1.0. For example, according to one implementation the average unconstrained diameter of the main body portion 552a is about 2.0 millimeters and the average unconstrained diameter of the distal portion 552b is about 4.0 millimeters. According to some implementations the ratio of the unconstrained length of the distal portion 552b and the unconstrained length of the main body portion 552a is between about 0.2 to about 0.7. For example, according to one implementation the unconstrained length of the main body portion 552a is between about 15 to 25 millimeters and the unconstrained length of the distal portion is between about 5 to 10 millimeters.

Figure 51A:
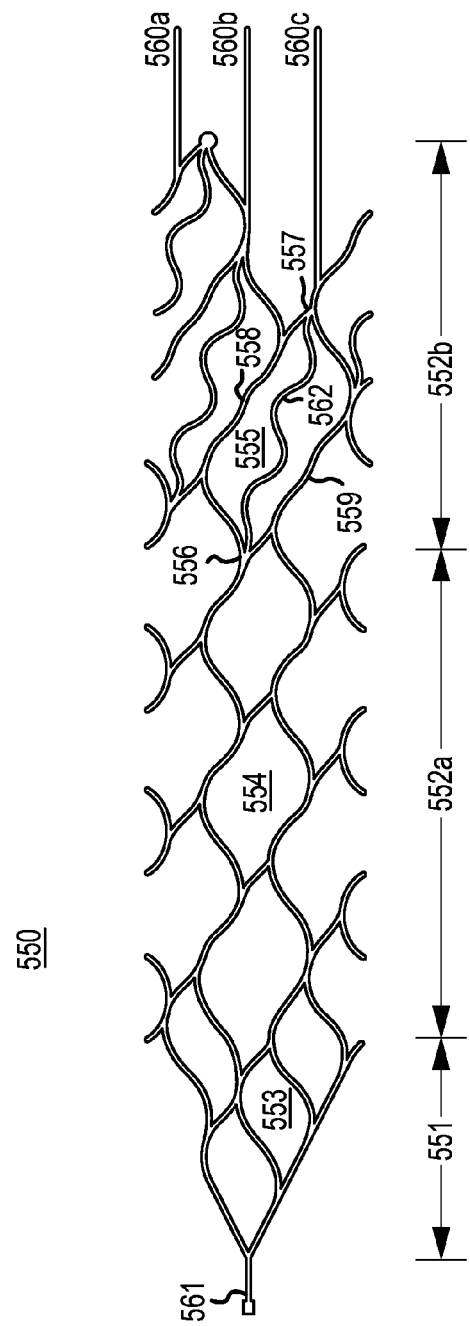
FIGS. 51A-D illustrate two-dimensional plane views of retrieval devices according to some implementations.
Figure 51B:
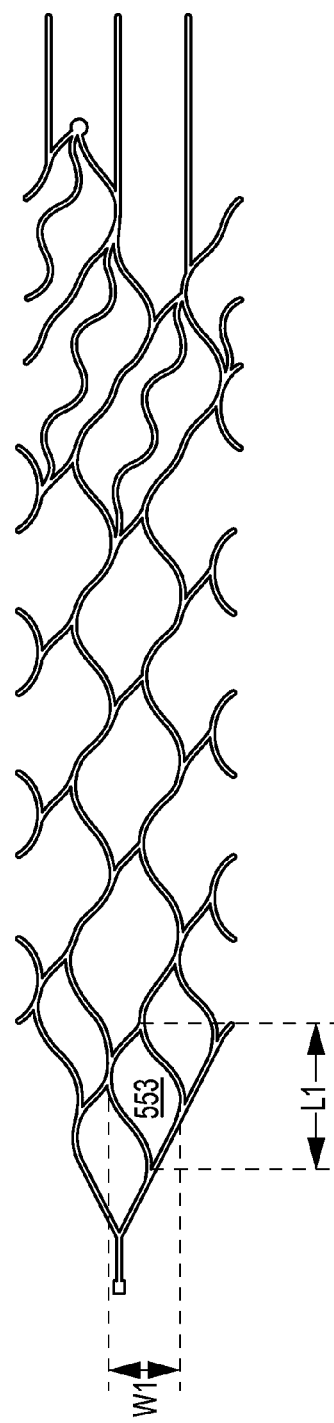
Figure 51C:
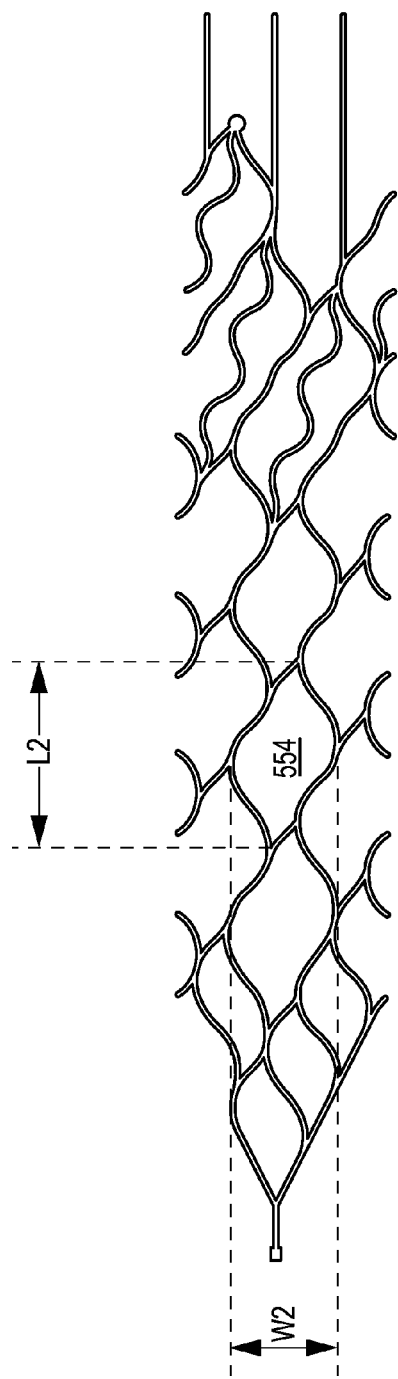
Figure 51D:
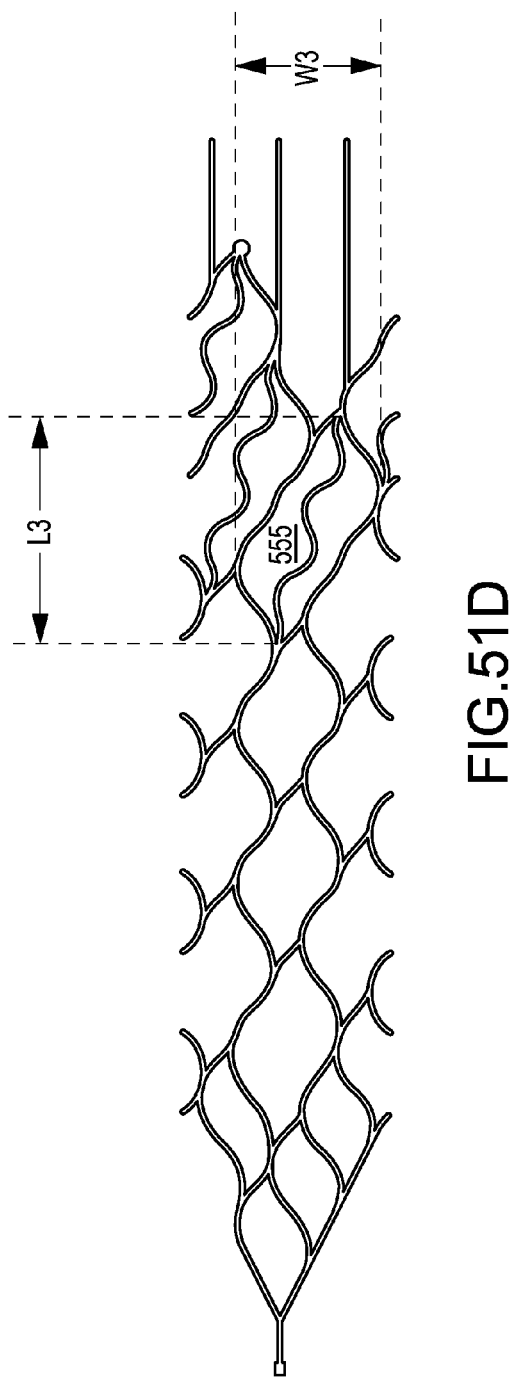

According to some implementations, cell structures in the proximal taper portion 551, main body portion 552 and distal portion 552b are of different sizes. In the example of FIG. 51A, the cell sizes are multiples of one another with cell structure 554 comprising an area approximately equal to two of cell structure 553 and cell structure 555 comprising an area approximately equal to three of cell structures 553. It is important to note that cell sizes that are multiples of one another are not required. FIG. 51B illustrates the length dimension L1 and width dimension W1 of cell structure 553. FIG. 51C illustrates the length dimension L2 and width dimension W2 of cell structure 554. FIG. 51D illustrates the length dimension L3 and width dimension W3 of cell structure 555.

According to some implementations cell structures 553, 554 and 555 each have an average length to width ratio greater than one when the retrieval device is in an unexpanded state and when the retrieval device is in an expanded state. The ability of the cell structures 553, 554, and 555 to maintain an average length to width ratio of greater than one inhibits the cells from collapsing lengthwise as the device 550 travels through a delivery catheter or duct of a patient. In other words, the cell structures of device 550 are inhibited from collapsing lengthwise on themselves in an accordion like fashion due to their length to width ratios being greater than one.

Another aspect is reflected in the length L3 of the cell structures 555 in the distal portion 552b of the device. Because the distal portion 552b assumes an expanded diameter that is greater than the expanded diameter of the remaining portions of the device, the length dimension L3 is selected to be sufficiently long in comparison to its width dimension W3 so as to ensure that the cell structures 555 maintain their length dimension to be greater than their width dimensions when the retrieval device 550 transitions from an unexpanded to an expanded state.

In some implementations the average length to width ratio of the cell structures in the distal portion 552b of the cylindrical main body portion are greater than the average length to width ratio of the cell structures in the proximal portion 552a of the cylindrical main body portion, the average length to width ratio of the cell structures in the proximal portion 552a of the cylindrical main body portion being greater than the average length to width ratio of the cell structures in the proximal end portion 551, and with the average length to width ratio of the cell structures in the proximal end portion being greater than one when the self-expandable member is in the unexpanded and expanded configuration.

In some implementations the retrieval device 550 is constructed in a manner that results in a radial force being exerted by the main body portion 552a that is greater than the radial force exerted by the distal portion 552b when the retrieval device 550 is deployed within a duct of a patient. In such an implementation, the main body portion 552a is situated to capture an obstruction while the distal portion 552b more gently acts against a wall of the duct distal to the obstruction to entrap portions of the obstruction that become dislodged during and after its capture. As such, according to one method the retrieval device 550 is placed at the treatment site of a patient by use of a delivery catheter, as previously disclosed herein. The retrieval device 550 is positioned at a distal end of the delivery catheter so that the main body portion 552a is positioned at the site of the obstruction to be retrieved. When sheathed within the delivery catheter the main body portion 552a and the distal portion 552b have the same, or substantially the same, diameter. Thereafter, the delivery catheter is withdrawn proximally to cause the constrained retrieval device to expand at the treatment site so that the main body portion 552a is at least partially forced into the obstruction and so that at least a portion of the distal portion 552b more gently rests against the duct wall distal to the obstruction. Upon the obstruction being captured within the main body portion 552a of device 550, the device may be removed from the patient in a manner consistent with one or more of the methods previously disclosed herein. During such removal, as the retrieval device is pulled proximally the distal portion 552b may sweep along the duct wall to entrap portions of the obstruction that may have become dislodged. By virtue of its enhanced diametric dimension, the distal portion 552b maintains contact with the duct wall during all or a portion of the removal procedure.

As discussed above, a lower strut density in the main body portion 552a (as compared to the strut density in the proximal taper portion 551) facilitates an integration of the retrieval device 550 within an obstruction. However, in some implementations the retrieval device is constructed in a manner that results in a radial force being exerted by the main body portion 552a that is greater than the radial force exerted by the distal portion 552b when the retrieval device 550 is deployed within a duct of a patient. To achieve this variation in a radial force, in some implementations the width dimension of the struts in the main body portion 552a of the retrieval device are cut to have a larger width dimension of at least some or all of the struts in the distal portion 552b.

As shown in FIG. 51A, in some implementations the strut density in the distal segment 552b is further enhanced by the inclusion of non-linear struts 562 in at least some of the cell structures. In some implementations the non-linear struts 562 extend between the proximal end 556 and distal end 557 of cell structures. In some implementations the non-linear struts 562 (or intermediate struts) extend between the proximal end 556 and distal end 557 of cell structures with the non-linear strut 562 having substantially the same length as the upper strut 558 and/or lower strut 559 in the as-cut configuration. Such a construction enhances the ability of the cell structure struts to nest resulting in a lower achievable constrained diameter of the retrieval device. So as not to greatly impact the radial force produced in the distal segment 552b, in some implementations the non-linear struts 562 have a width dimension less than the width dimension of the upper and lower struts 558 and 559. In some implementations the ratio of the width dimension of struts 562 and the width dimension of each of the upper and lower struts 558 and 559, respectively, is between about 0.70 and 0.90. For example, according to one implementation each of the upper and lower struts, 558 and 559, have an as-cut width dimension of about 0.0035 inches while strut 562 has an as-cut width dimension of about 0.0025 inches.

Although not shown in FIGS. 51A-51D, in some implementations the cell structures in the distal segment 552b have wire windings selectively woven through their struts in order to endow the distal segment with a desired radiopacity and/or stiffness as discussed above in relation to FIG. 50.

In some implementation, a plurality of antennas 560a, 560b and 560c extend distally to the distal-most circumferential row of cell structures in the distal segment 552b. In a manner like that disclosed above in conjunction with the device of FIGS. 47A and 47B, the distal ends of antennas 560a, 560b and 560c are joined together so as to provide the internal cavity of device 550 with a partially closed-end. In effect, the closed-end forms a basket that facilitates the collection of particulates, such as embolic material, that may become dislodged during a retrieval procedure. In some implementations the juncture of antennas 560a, 560b and 560c is formed by soldering together the distal ends of the antennas. In some implementations the distal ends of the antennas are positioned within an encasement, such as a coil spring or other perforated structure, with a solder or other bonding agent being applied within and/or about the encasement to effectuate a bonding together of the distal ends of the antennas. In some implementations the encasement comprises a rounded atraumatic distal tip. In some implementations the encasement comprises a radiopaque material.

Figure 52A:
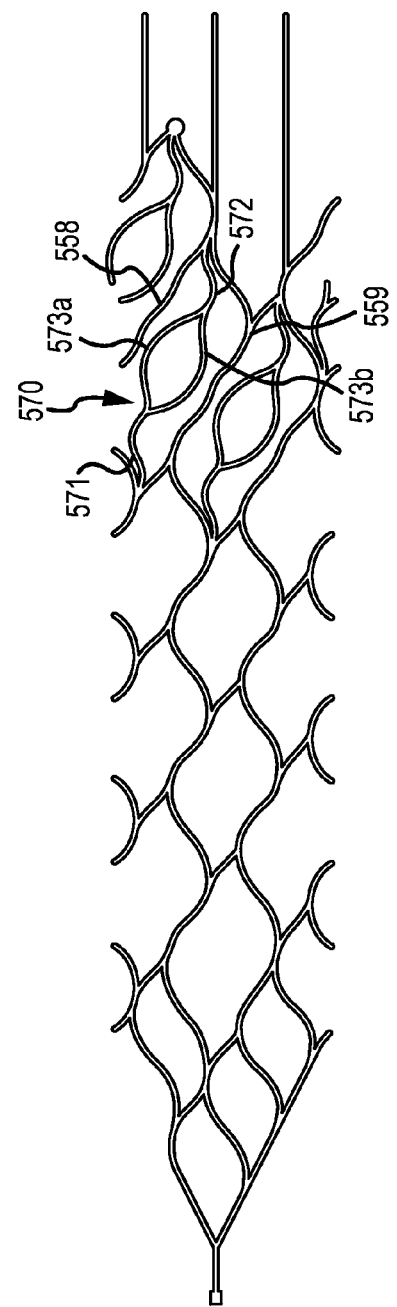
FIGS. 52A and 52B illustrate two-dimensional plane views of retrieval devices according to some implementations.

FIG. 52A illustrates a retrieval device similar to that disclosed in FIGS. 51A-51D. A difference lies in the construction of the non-linear/intermediate struts 570 that are disposed in the distal segment cell structures 555. As shown in FIG. 52A, the intermediate strut 570 comprises first and second curvilinear elements 571 and 572, respectively, between which are bifurcation struts 573a and 573b. An advantage of the configuration of strut 570 is that it provides additional coverage, as compared to strut 562, to assist in entrapping embolic debris. In some implementations the non-linear struts extend between the proximal end 556 and distal end 557 of cell structures 555. In some implementations the non-linear strut 570 extends between the proximal end 556 and distal end 557 of cell structures with the combined length of elements 571, 572 and 573a being approximately the same length as the upper strut 558 and/or the combined length of elements 571, 572 and 573b being substantially the same length as the lower strut 559 in the as-cut configuration. So as not to greatly impact the radial force produced in the distal segment 552b, in some implementations the non-linear struts 570 have a width dimension less than the width dimension of the upper and lower struts 558 and 559. In some implementations the ratio of the width dimension of struts 570 and the width dimension of each of the upper and lower struts 558 and 559, respectively, is between about 0.70 and 0.90. For example, according to one implementation each of the upper and lower struts, 558 and 559, have an as-cut width dimension of about 0.0035 inches while strut 360 has an as-cut width dimension of about 0.0025 inches.

Figure 52B:
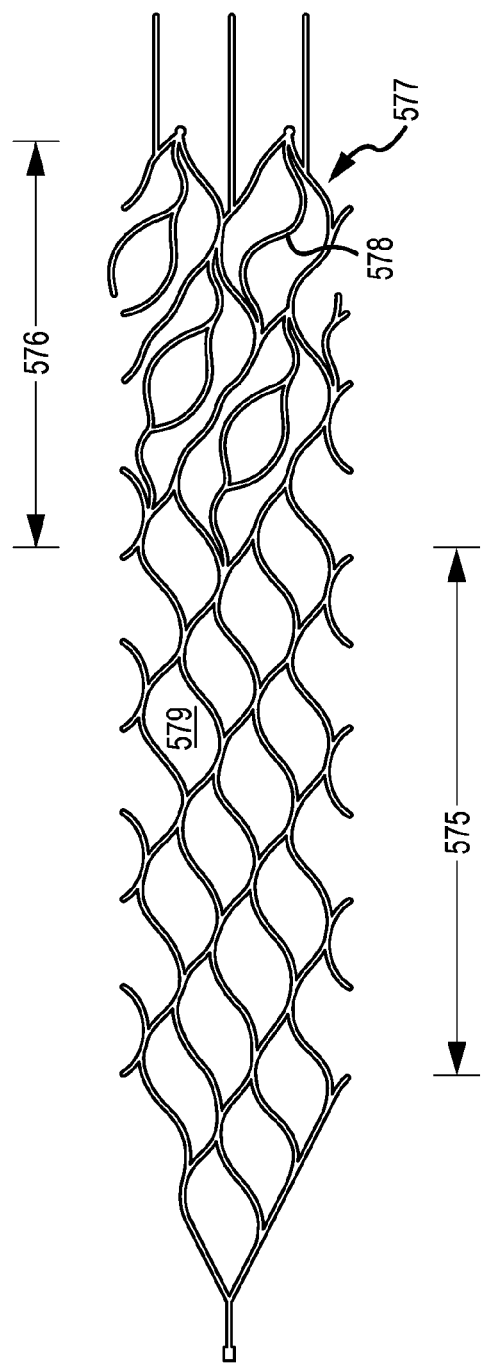

FIG. 52B illustrates a variation to the retrieval device shown in FIG. 52A with differences existing in the size of the cell structures 579 in the proximal section 575 of the cylindrical body portion and the inclusion of cell structure 577 in the distal section 576 of the cylindrical body portion. As shown in FIG. 52B, cell structures 579 are smaller in size to the similarly situated cell structures in the retrieval device of FIG. 52A as a result of additional struts being added (those depicted by dashed lines) to essentially reduce the size of the cell structures by half. As noted above, another difference lies in the inclusion of cell structure 577 at the distal end of the retrieval device to provide a the device with a substantial uniform circumferential end. In one implementation an intermediate strut 578 extends between the opposite ends of cell structure 577 in a manner similar to that described above with respect to intermediate struts 562.

Figure 53:
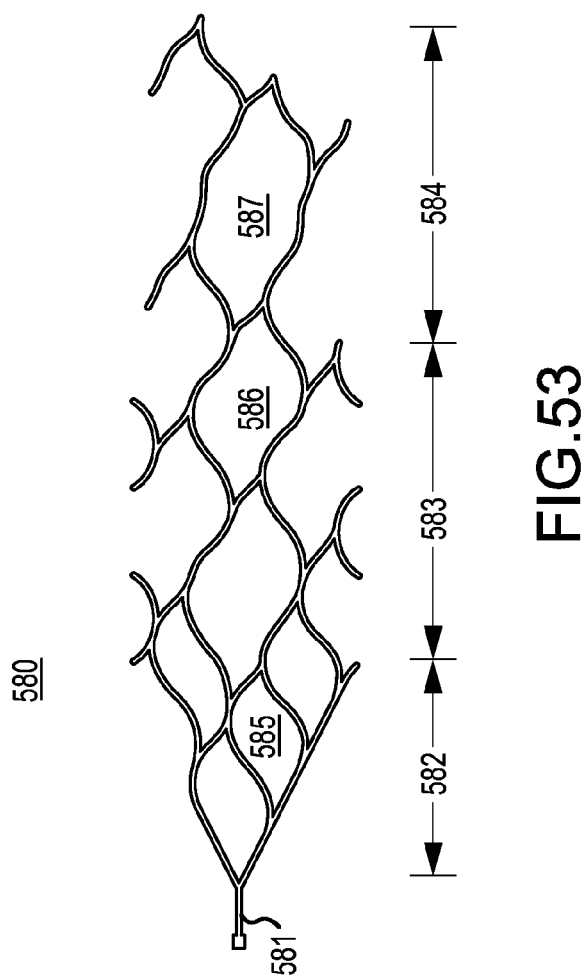
FIG. 53 illustrates a two-dimensional plane view of a retrieval device according to some implementations.

FIG. 53 illustrates a retrieval device 580 that comprises different size cell structures along its length, similar to that disclosed above in conjunction with the device 550 illustrated in FIGS. 51A-51D. FIG. 53 depicts the device 580 in a two-dimensional layout as if it were cut along its length and laid out on a flat surface. The device includes a proximal antenna 581, a proximal taper portion 582, a main body portion 583 and a distal portion 584. In the as-cut manufactured state the main body portion 583 and the distal portion 584 have the same, or substantially same, diameter. At a point in time after the device 580 has been cut, such as by laser cutting, the device 580 is formed so that the unconstrained configuration of the distal portion 584 has a diameter that is greater than that of the unconstrained main body portion 583. The post as-cut form of the device 580 may be achieved with the use of mandrels or other tools and methods known in the art. In some implementation the ratio of the unconstrained diameter of the distal portion 584 and the main body portion 583 is between about 1.2/1.0 and about 2.0/1.0. For example, according to one implementation the average unconstrained diameter of the main body portion 583 is about 2.0 millimeters and the average unconstrained diameter of the distal portion 584 is about 4.0 millimeters.

As illustrated in FIG. 53, the cell structures in the proximal taper portion 582, main body portion 583 and distal portion 584 are of different sizes. In the example of FIG. 53, the cell sizes are multiples of one another with cell structures 586 comprising an area approximately equal to two of cell structure 585 and cell structure 587 comprising an area approximately equal to three of cell structures 585. It is important to note that cell sizes that are multiples of one another are not required. As with cell structures 553, 554 and 555 in device 550 described above, cell structures 585, 586 and 587 each have an average length to width ratio greater than one when the retrieval device 580 is in an unexpanded state and when the retrieval device 580 is in an expanded state. As discussed above, the ability of the cell structures to maintain an average length to width ratio of greater than one inhibits the cells from collapsing lengthwise as the retrieval device travels through a delivery catheter or duct of a patient. In other words, the cell structures of device 580 are inhibited from collapsing lengthwise on themselves in an accordion like fashion due to their length to width ratios being greater than one.

Another aspect is reflected in the length of the cell structures 587 in the distal portion 584 of the device. Because the distal portion 584 assumes an expanded diameter that is greater than the expanded diameter of the remaining portions of the device, the length dimension of cell structure 587 is selected to be sufficiently long in comparison to its width dimension so as to ensure that the cell structure maintains its length dimension to be greater than its width dimensions when the retrieval device 580 transitions from an unexpanded to an expanded state.

In some implementations the retrieval device 580 is constructed in a manner that results in a radial force being exerted by the main body portion 583 that is greater than the radial force exerted by the distal portion 584 when the retrieval device 580 is deployed within a duct of a patient. In such an implementation, the main body portion 583 is situated to capture an obstruction while the distal portion 584 more gently acts against a wall of the duct distal to the obstruction to entrap portions of the obstruction that become dislodged during and after its capture. As such, according to one method the retrieval device 580 is placed at the treatment site of a patient by use of a delivery catheter, as previously disclosed herein. The retrieval device 580 is positioned at a distal end of the delivery catheter so that the main body portion 583 is positioned at the site of the obstruction to be retrieved. When sheathed within the delivery catheter the main body portion 583 and the distal portion 584 have the same, or substantially the same, diameter. Thereafter, the delivery catheter is withdrawn proximally to cause the constrained retrieval device to expand at the treatment site so that the main body portion 583 is at least partially forced into the obstruction and so that at least a portion of the distal portion 584 more gently rests against the duct wall distal to the obstruction. Upon the obstruction being captured within the main body portion 583 of device 580, the device may be removed from the patient in a manner consistent with one or more of the methods previously disclosed herein. During such removal, as the retrieval device is pulled proximally the distal portion 584 may sweep along the duct wall to entrap portions of the obstruction that may have become dislodged. By virtue of its enhanced diametric dimension, the distal portion 584 maintains contact with the duct wall during all or a portion of the removal procedure.

Although not shown in FIG. 53, in some implementations the cell structures in the distal segment 584 have wire windings selectively woven through their struts in order to endow the distal segment with a desired radiopacity and/or stiffness as discussed above in relation to FIG. 50.

Figure 54:
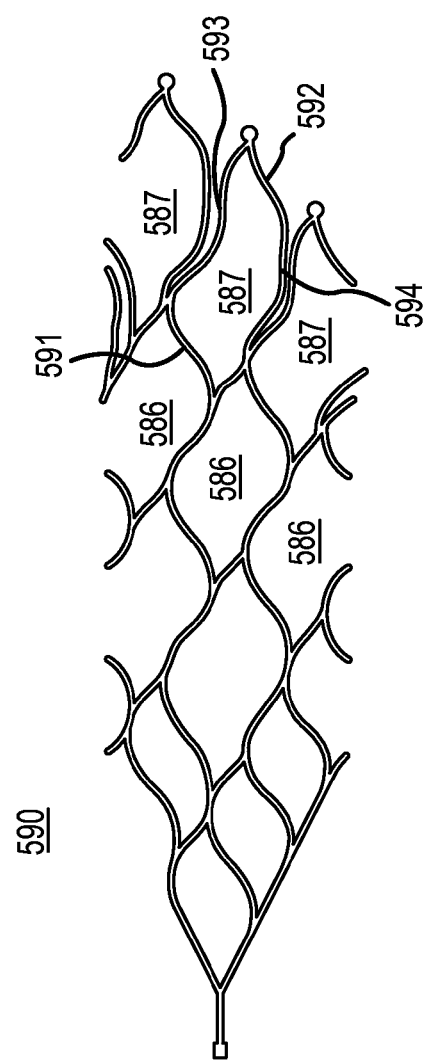
FIG. 54 illustrates a two-dimensional plane view of a retrieval device according to some implementations.
Figure 55:
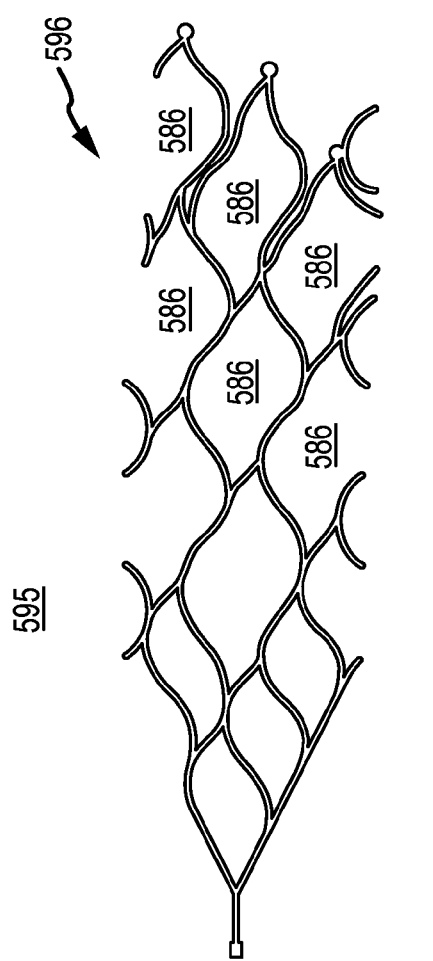
FIG. 55 illustrates a two-dimensional plane view of a retrieval device according to some implementations.

The retrieval device 590 illustrated in FIG. 54 is similar to device 580 with a difference being the manner in which the cell structures 587 are interconnected. Cell structures 587 have a proximal side 591, a distal side 592, a top side 593 and a bottom side 594. As shown in FIG. 54, cell structures 587 are coupled with the adjoining cell structures 586 along at least a portion of the proximal side 591. However, the top and bottom sides 593 and 594 of cell structures 587 are unattached. As mentioned above, it is desirable that the length to width ratio of cell structures 587 remain greater than one when the retrieval device 590 is moved through a delivery catheter or duct of a patient. By de-coupling the top and bottom sides of the cell structures, forces that would normally be applied to the cell structures during expansion to cause them to appreciably expand in width are largely removed. This assists in ensuring that the length to width ratio of cell structures 587 remains greater than one when the device 590 assumes an expanded state. As shown in FIG. 55, as a result of the de-coupling of the distal-most circumferential row of cell structures, the selection of smaller sized cell structures is accommodated. For example, as shown in FIG. 55 the distal-most circumferential row of cell structures 596 may comprise cell structures that are the same or similar to proximally situated cell structures 586. It is appreciated, however, that the size and shape of the distal-most circumferential row of cell structures need not mimic those of the proximally situated cell structures.

Figure 56A:
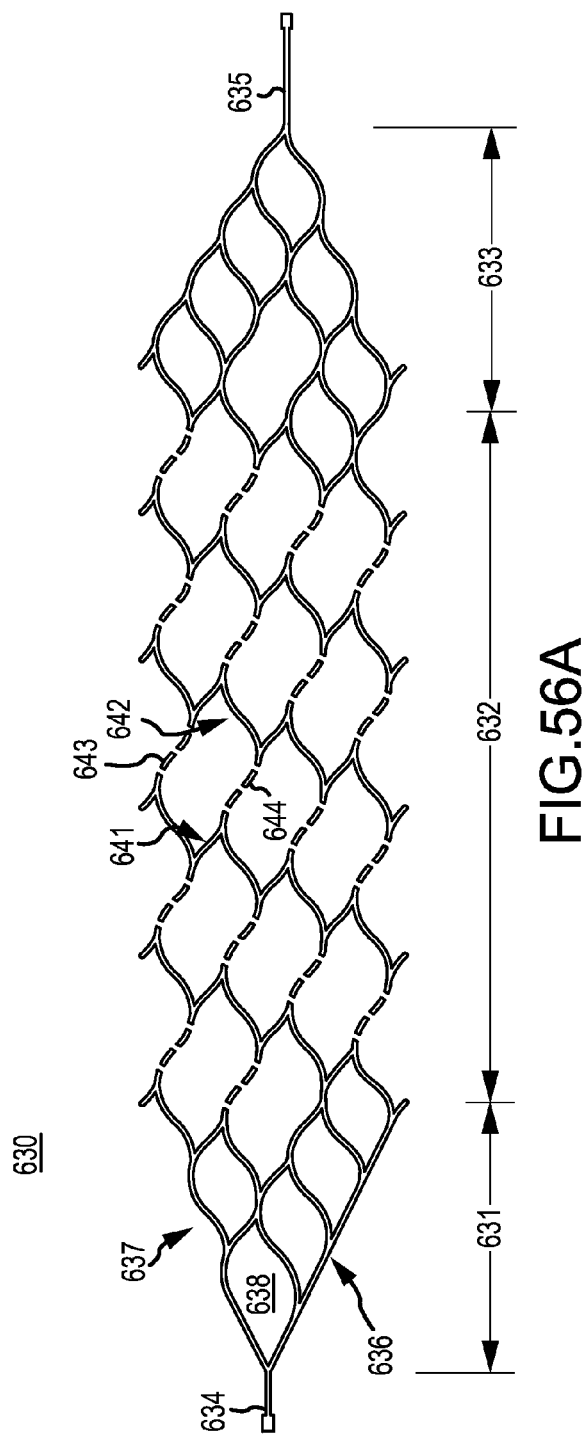
FIGS. 56A and 56B illustrates a two-dimensional plane view of retrieval devices according to some implementations.

Turning now to FIG. 56A, a retrieval device 630 is shown having a similar construction as the device 800 depicted in FIG. 45A, albeit with fewer cell structures and for use in smaller diameter vessels/ducts. FIG. 56A is a two dimensional view of a retrieval device 630 according to another implementation. The retrieval device 630 comprises an expandable member that has a proximal tapered end portion 631, a cylindrical main body portion 632 and a distal tapered end portion 633. The outer-most cell structures in the proximal tapered end portion have outer wall segments that form on one side a non-undulating rail segment 636 and on the other side an undulating rail segment 637. Each of the rail segments 636 and 637 extend from a proximal-most end of the expandable member to a position at or near the proximal end of the cylindrical main body portion 632. A proximal antenna 634 extends proximally from a proximal-most cell structure 638 while a distal antenna 635 extends distally from the distal end of distal tapered section 633. The cell structures 640 in the cylindrical main body portion 632 comprise facing proximal and distal flexure elements 641 and 642, respectively, which generally comprise convex and/or concave like structures, such as for example V-like and U-like structures. The proximal and distal flexure elements 641 and 642 are interconnected by a pair of diagonally extending and circumferentially spaced-apart struts 643 and 644.

Figure 56B:
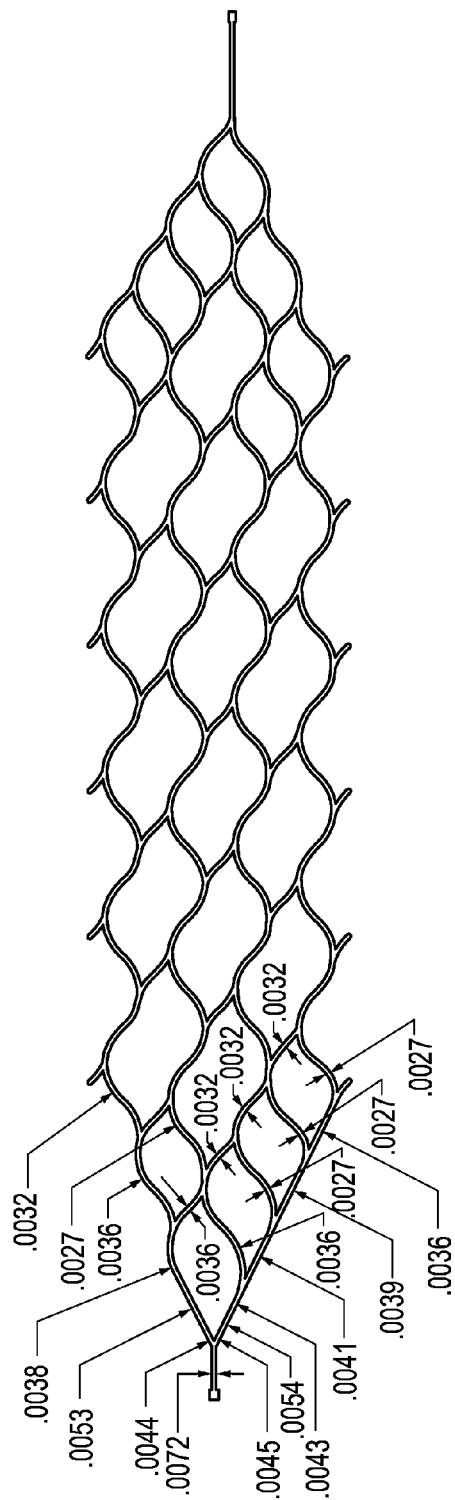

FIG. 56B shows the as-cut width dimensions in inches of the various struts in the proximal tapered end portion 631 according to one implementation, each of the dimensions having a tolerance of ±0.0004 inches. According to one implementation the struts in the proximal tapered end portion 631 have an as-cut thickness dimension of about 0.0045±0.0004 inches.

As previously discussed, it is desirable that the cylindrical main body portion 632 possess sufficient radial strength to cause at least a partial integration of its struts into an obstruction targeted for full or partial removal. However, the radial strength of the cylindrical main body portion 632 must be sufficiently low to avoid undue damage to the vessel or duct under treatment. In order to achieve a desired radial strength the cross-sectional area and/or width and/or thickness of the struts that form the cylindrical main body portion 632 must be properly dimensioned.

Another feature of consideration is that of flexibility. The cylindrical main body portion 632 should possess sufficient flexibility to permit the retrieval device 630 to be advanced and retracted though the tortuous anatomy of a patient. However, the cylindrical main body portion 632 should also possess sufficient stiffness to permit it to be pushed through a delivery catheter and a duct of a patient without it collapsing on itself. It has been discovered that stiffness also plays a factor in the ability of the retrieval device to be withdrawn into a delivery catheter at a point in time after it has been deployed. As discussed above, upon a misplacement of the retrieval device within a duct of a patient, and sometimes upon removal of the retrieval device from the patient, the retrieval device is fully or partially withdrawn back into the delivery catheter. It has been discovered that in the absence of a requisite amount of stiffness within the cylindrical main body portion it is difficult to withdraw the retrieval device back into the delivery catheter after it has been deployed. Tests have shown that in some situations when all the struts within the cylindrical main body portion have a uniform cross-section, insufficient stiffness results when the struts are sized to achieve a proper amount of radial force.

It has been discovered that the cross-section of flexure elements 641 and 642 most significantly impact radial force in the cylindrical main body portion 632 while the cross-section of diagonally disposed struts 643 and 644 contributing little if any to the radial force produced within the cylindrical main body portion 632. According to some implementations, in order to achieve the right combination of radial strength and stiffness within the cylindrical main body portion 632, the cross-section of flexure elements 641 and 642 is different than the cross-section of struts 643 and 644. Because in many instances the retrieval device is cut from a tube of uniform thickness, the width dimensions of the flexure elements 641, 642 and diagonally disposed struts 643, 644 are varied to achieve the desired radial force and stiffness characteristics. However, it is to be appreciated that dimensions other than width may be varied to achieve the same or similar results.

According to some implementations all or substantially all of the struts in the cylindrical main body portion 632 are of the same thickness with the flexure elements 641 and 642 having a first average width dimension and the diagonally disposed struts 643 and 644 having a second average width dimension that is greater than the first average width dimension. The second average width dimension is sufficiently large to compensate for the lack of stiffness that would otherwise exists if the second average width dimension was the same as the first average width dimension. In some implementations the as-cut second average width dimension is in the range of about 1.1 to about 2.0 times greater than the as-cut first average width dimension. In other implementations the as-cut second average width dimension is in the range of about 1.2 to about 1.5 times greater than the as-cut first average width dimension. According to one experiment the as-cut first average width dimension was about 0.0032 inches and the as-cut second average width dimension was about 0.0040 inches. The results showed that the average deflection stiffness of the cylindrical main body portion 632 increased by about a 40% to 50% as a result of increasing the width dimension of the diagonally disposed struts 643 and 644 from 0.0032 inches to 0.0040 inches. This occurs without an appreciable increase in radial force.

Figure 57:
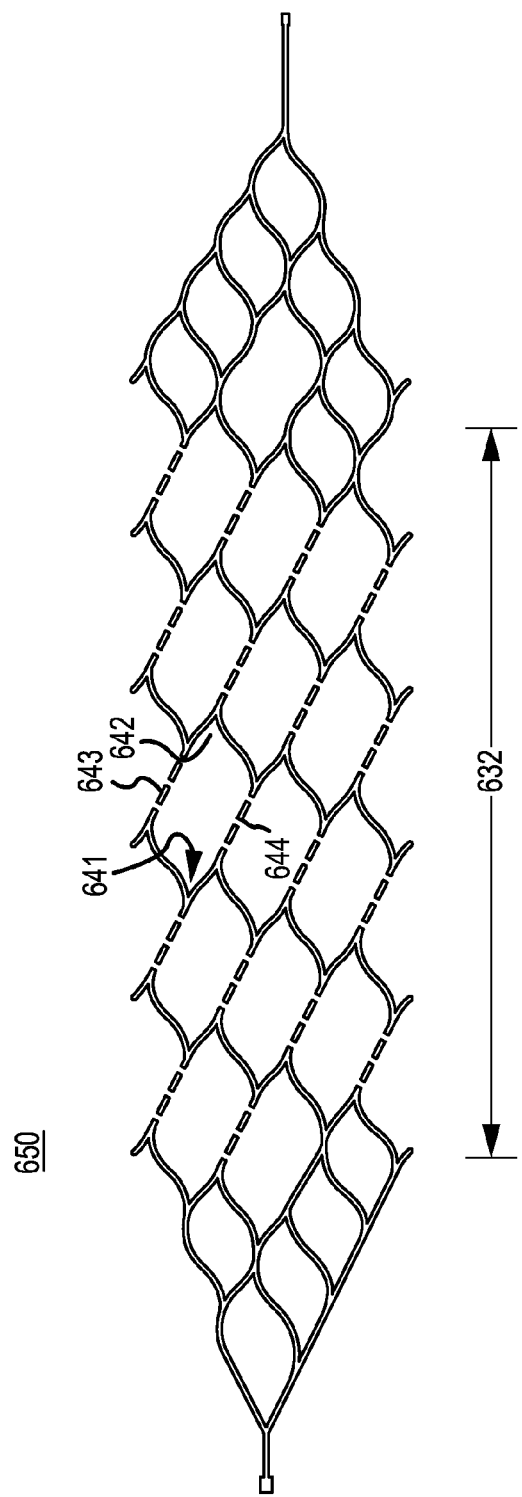
FIG. 57 illustrates a two-dimensional plane view of a retrieval device according to some implementations.

FIG. 57 is illustrates a retrieval device 650 similar to retrieval device 630 with a difference being in the construction of the diagonally disposed struts 643 and 644. As shown in the figures, struts 643 and 644 in retrieval device 630 are curvilinear while struts 643 and 644 in retrieval device 650 are straight.

According to some implementations the width dimensions of the diagonally disposed struts 643 and 644 are uniform along their length. With respect to the example dimensions above, it would mean that the entire length of struts 643 and 644 would have an average width dimension of 0.0040 inches. In other implementations struts 643 and 644 comprise middle segments that are disposed between opposite proximal and distal end segments, with the proximal end segments being coupled to the proximal flexure element and the distal end segments being coupled to the distal flexure element. Using the same example dimensions above, the flexure elements 641 and 642 along with the proximal and distal segments of struts 643 and 644 may have an average width dimension of 0.0032 inches while the middle segment of struts 643 and 644 may have an average width dimension of 0.0040 inches. In other implementations struts 643 and 644 comprise middle segments that are disposed between opposite proximal and distal tapered end segments, with the proximal tapered end segments being coupled to the proximal flexure element 641 and the distal tapered end segments being coupled to the distal flexure element 642. Using the same example dimensions above, the flexure elements 641 and 642 may have an average width dimension of 0.0032 inches with the middle segment of struts 643 and 644 having an average width dimension of 0.0040 inches, the average width dimension of the proximal and distal tapered end segments transitioning from 0.0032 inches to 0.0040 inches.

As disclosed above in the description of the device depicted in FIG. 50, a process of weaving/winding a wire or ribbon about the struts of the retrieval device may be used for the purpose of enhancing the radiopacity of the device and also for affecting the stiffness of the device. In the implementations disclosed above, the discussion was limited to incorporating such a feature into the distal segment of retrieval devices. What follows is a description that involves the use of such wire windings in other portions of the device.

Figure 58B:
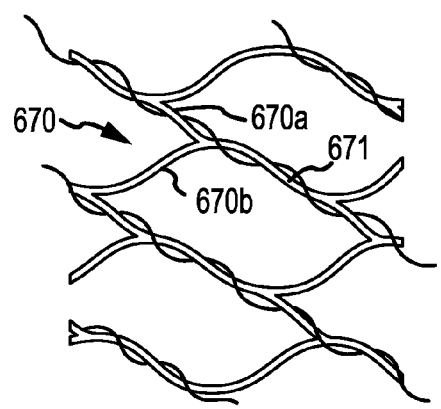
FIG. 58B illustrates an enlarged view of cell structures depicted in FIG. 58A.

FIG. 58A illustrates a retrieval device 630 that has a similar construction to the retrieval device 650 shown in FIG. 56. The retrieval device 660 comprises wires that are wound about selective struts for the purpose of enhancing the radiopacity of the device 660 and/or to affect the stiffness of one or more portions of the device. In the exemplary implementation of FIG. 58A three radiopaque wires (or ribbons) 661, 662 and 663 are woven along the length of the retrieval device to enhance the radiopacity of the device along essentially its entire length and to enhance the stiffness of at least the cylindrical main body portion 666. In the implementation of FIG. 58A the wires 661-663 are woven about the diagonally downward oriented struts (as viewed from left to right) in the cylindrical main body portion 666 so that only the short legs 670a of the flexure elements 670 possess wire windings. As shown in detail in FIG. 58B, the long legs 670b of the flexure elements 670 are free or substantially free of wire windings. A virtue of this winding configuration is that it enables the wires to be applied to the retrieval device, and particularly the cylindrical main body portion 666, in a manner that disproportionally affects stiffness and radial force. For example, the average deflection stiffness of the cylindrical main body portion 666 may be moderately to significantly increased without there being a corresponding increase in the radial force exerted by the cylindrical main body portion when it is in an unexpanded state. Prototypes have shown that the average deflection stiffness of the cylindrical main body portion 666 may be increased by up to 50% with there being relatively little to no increase in the radial force.

According to one exemplary implementation, the struts in the cylindrical main body portion 666 have an as-cut thickness dimension of about 0.0045 inches with each of struts 670a, 670b and 671 having width dimensions of about 0.0032, 0.0032 and 0.0040 inches, respectively. In one implementation the wires comprise platinum with a width and/or diameter of between about 0.0020 inches and 0.0025 inches with there being an average of about one to ten windings per strut, and most generally one to five windings per strut. It is to be appreciated that a single wire or any multiple thereof may be used in lieu of the three wire configurations depicted in FIG. 58A. Moreover, it is important to note that, in the case of enhancing radiopacity that the wire or wires may comprise any radiopaque material or combination of materials as discussed above in conjunction with FIG. 50. In the event that wire windings are applied only for the purpose of affecting stiffness, the wire or wires may comprise any material suitable for such purpose, such as for example metallic, polymeric and composite materials. In some implementations the cross-sectional area of the one or more wires varies to provide a variation in radiopacity and/or stiffness along the length of the device.

According to some implementations, the cylindrical main body portion 666 has a first average deflection stiffness in the absence of the one or more wires or ribbons 661-663 and a second average deflection stiffness with presence of the one or more wires or ribbons 661-663, the dimensional and material characteristics of the one or more wires or ribbons 661-663 and the number of windings per unit length of the diagonally extending and circumferentially spaced-apart struts in the cylindrical main body portion selected to cause the second average deflection stiffness to be greater than the first average deflection stiffness by a factor of between about 1.2 to about 1.8 with there being a disproportionally lower increase in the radial force exerted by the cylindrical main body portion when it is in an unexpanded state.

Figure 59B:
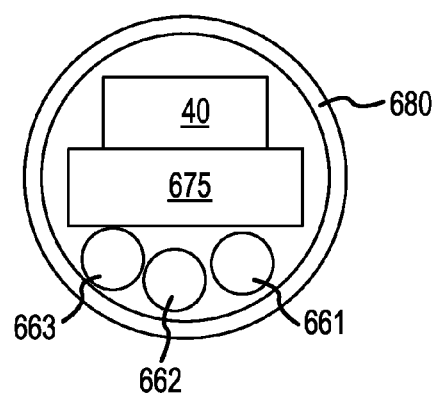
FIG. 59B illustrates a cross-sectional view of the joint member depicted in FIG. 59A.

According to some implementations the proximal and distal end segments of wires 661-663 are coupled to the retriever device 660 as depicted in FIG. 59 and FIG. 60, respectively. It is important to note that other attachment/coupling configurations are also possible. FIG. 59A illustrate the proximal attachment of wires 661-663 at the location where the distal end of elongate wire 40 (see for example FIG. 1A) is attached to the proximal antenna 675. In one embodiment, the distal end of wire 40 has a flat profile with a width of about 0.005 inches with the width and thickness of the proximal antenna 675 being about 0.0063 and about 0.0035 inches, respectively. FIG. 59B illustrates a cross-sectional view of the resulting joint where in one implementation the proximal ends of wires 661-663 reside on a bottom side of proximal antenna 675 and the distal end of elongate wire 40 resides on a top side of proximal antenna 675.

In one implementation, the distal end of elongate wire 40, the proximal ends of wires 661-663 and the proximal antenna 675 are coupled together within a coil structure 680. In one implementation the coil structure 680 has a closely wrapped distal segment 680a, and a loosely wrapped proximal segment 680b that includes one or more gaps 680c. In one implementation, the length of proximal antenna 675 and the coil 680 are substantially equal. Upon the coil 680 being placed over the overlapping components a bonding agent is introduced into the internal cavity of the coil 680 to bond the elongate wire 40, proximal antenna 675 and wires 661-663 together with at least a portion of the coil. In one implementation, the end segments of wires 661-663 reside entirely within distal coil segment 680a. The bonding agent may be an adhesive, solder, or any other suitable bonding agent. When the bonding agent is a solder, a preceding step in the process may involve coating the various components with tin or another suitable wetting agent. In one implementation the solder is gold and is used to enhance the radiopacity of the joint so that the joint may serve as a proximal radiopaque marker. This implementation is particularly applicable in situations where wires 661-663 are non-radiopaque. In addition to the use of gold, all or portions of the coil may be made of a radiopaque material to further enhance the radiopacity of the joint. In other implementations, in lieu of the use of a single coil 680, two or more coils in abutting relationship are used with, for example, a distal closely wound coil and a proximal loosely wound coil with gaps situated proximal to the closely wound coil.

Figure 60A:
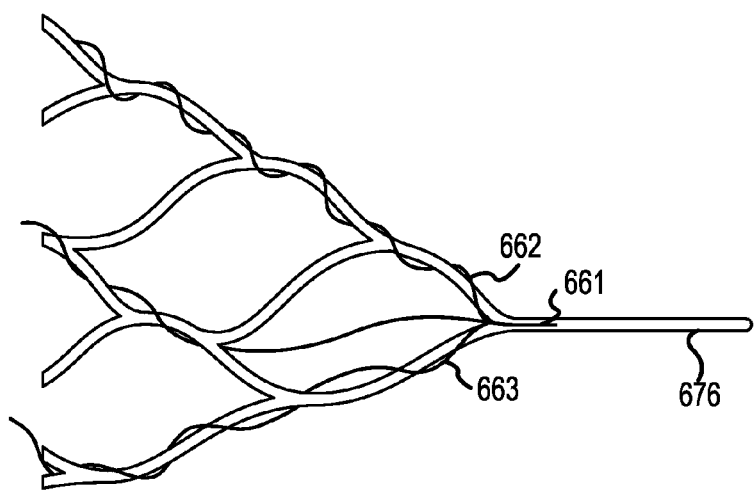
FIGS. 60A and 60B show wire attachment configurations according to some implementations.
Figure 60B:
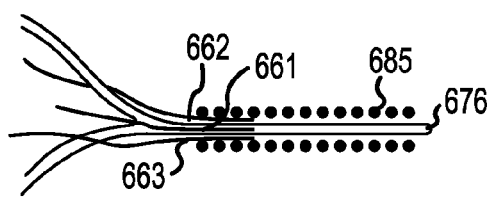

FIGS. 60A and 60B illustrate several methods by which the distal end segments of wires 661-663 may be attached to the distal antenna 676. In the implementation of FIG. 60A the distal ends of wires 661-663 are bonded directly to the distal antenna by use of a bonding agent such as solder or glue. FIG. 60B shows another implementation where the distal ends of wires 661-663 are interposed between the distal antenna 676 and a coil 685 that surrounds it. In such an implementation a bonding agent may be introduced into the interior of the coil 685 to effectuate a bonding together the coil 685, distal antenna 676 and wires 661-663.

While the above description contains many specifics, those specifics should not be construed as limitations on the scope of the disclosure, but merely as exemplifications of preferred embodiments thereof. For example, dimensions other than those listed above are contemplated. For example, retrieval devices having expanded diameters of any where between 1.0 and 100.0 millimeters and lengths of up to 5.0 to 10.0 centimeters are contemplated. Moreover, it is appreciated that many of the features disclosed herein are interchangeable among the various implementations. Those skilled in the art will envision many other possible variations that are within the scope and spirit of the disclosure. Further, it is to be appreciated that the delivery of a vascular treatment device of the implementations disclosed herein is achievable with the use of a catheter, a sheath or any other device that is capable of carrying the device with the expandable member in a compressed state to the treatment site and which permits the subsequent deployment of the expandable member at a vascular treatment site. The vascular treatment site may be (1) at the neck of an aneurysm for diverting flow and/or facilitating the placement of coils or other like structures within the sack of an aneurysm, (2) at the site of an embolic obstruction with a purpose of removing the embolic obstruction, (3) at the site of a stenosis with a purpose of dilating the stenosis to increase blood flow through the vascular, etc.

What is claimed is:

1. An embolic obstruction retrieval device comprising; an elongate self-expandable member having a radially expanded configuration and a radially unexpanded configuration, the self-expandable member comprising a plurality of generally longitudinal undulating elements with adjacent undulating elements being interconnected in a manner to form a plurality of diagonally disposed cell structures, the self-expandable member having a proximal end portion and an elongate cylindrical main body portion comprising a proximal section and a distal section, the cell structures in the elongate cylindrical main body portion extending circumferentially around a longitudinal axis of the self-expandable member, the cell structures in the proximal end portion extending less than circumferentially around the longitudinal axis of the self-expandable member, in the expanded configuration the distal section of the elongate cylindrical main body portion having an average diameter greater than the average diameter of the proximal section of the elongate cylindrical main body portion, the retrieval device having a proximal antenna extending proximally from a proximal-most end of the proximal end portion of the self-expandable member; wherein the cell structures in the distal section of the elongate cylindrical main body portion comprise a proximal-most apex and a distal-most apex, at least some of the cell structures in the distal section of the elongate cylindrical main body portion comprising an intermediate strut that extends between the proximal-most and distal-most apices, the at least some of the cell structures in the distal section of the elongate cylindrical main body portion comprise a first strut that extends between the proximal-most and distal-most apices to form a bottom side of the cell structure and a second strut circumferentially spaced-apart from the first strut that extends between the proximal-most and distal-most apices to form a top side of the cell structure, the width of the intermediate strut being less than the width of each of the first and second struts.

2. The embolic obstruction retrieval device of claim 1, wherein the average length of the cell structures in the distal section of the elongate cylindrical main body portion is greater than the average length of the cell structures in the proximal section of the elongate cylindrical main body portion, the average length of the cell structures in the proximal section of the elongate cylindrical main body portion being greater than the average length of the cell structures in the proximal end portion, the average length to width ratio of the cell structures in the proximal end portion and elongate cylindrical main body portion being greater than one when the self-expandable member is in the radially unexpanded and radially expanded configuration.

3. The embolic obstruction retrieval device of claim 1, wherein the cell structures in the proximal end portion and the elongate cylindrical main body portion comprise strut elements, at least some of the struts of the cell structures in the distal section of the elongate cylindrical main body portion having one or more radiopaque wires or ribbons wound thereabout.

4. The embolic obstruction retrieval device of claim 1, wherein the elongate cylindrical main body portion comprises a first circumferential row of cell structures and a second distal-most circumferential row of cell structures, each of the second distal-most circumferential row of cell structures comprising a proximal side, a distal side, a top side and a bottom side, each of the proximal sides being coupled with an adjoining cell structure in the first circumferential row of cell structures and each of the distal, top and bottom sides being unattached to any adjoining cell structures.

5. The embolic obstruction retrieval device of claim 1, wherein the overall length of the intermediate strut is approximately equal to the overall length of at least one of the top and bottom sides.

6. The embolic obstruction retrieval device of claim 1, wherein the elongate cylindrical main body portion has a distal-most circumferential row of cell structures and comprises a plurality of circumferentially spaced-apart antennas extending distally therefrom and being joined together to form a partially closed end to the retrieval device at or near the distal end of the elongate cylindrical main body portion.

7. The embolic obstruction retrieval device of claim 1, further comprising a first proximally extending elongate flexible wire connected to the proximal antenna.

8. An embolic obstruction retrieval device comprising; an elongate self-expandable member having a radially expanded configuration and a radially unexpanded configuration, the self-expandable member comprising a plurality of generally longitudinal undulating elements with adjacent undulating elements being interconnected in a manner to form a plurality of diagonally disposed cell structures, the self-expandable member having a proximal end portion and an elongate cylindrical main body portion comprising a proximal section and a distal section, the cell structures in the elongate cylindrical main body portion extending circumferentially around a longitudinal axis of the self-expandable member, the cell structures in the proximal end portion extending less than circumferentially around the longitudinal axis of the self-expandable member, the average length to width ratio of the cell structures in the distal section of the elongate cylindrical main body portion being greater than the average length to width ratio of the cell structures in the proximal section of the elongate cylindrical main body portion, the average length to width ratio of the cell structures in the proximal section of the elongate cylindrical main body portion being greater than the average length to width ratio of the cell structures in the proximal end portion, the average length to width ratio of the cell structures in the proximal end portion being greater than one when the self-expandable member is in the unexpanded and expanded configuration, the retrieval device having a proximal antenna extending proximally from a proximal-most end of the proximal end portion of the self-expandable member, wherein each of the cell structures in the distal section of the elongate cylindrical main body portion comprises a proximal-most apex and a distal-most apex, at least some of the cell structures in the distal section of the elongate cylindrical main body portion comprising an intermediate strut that extends between the proximal-most and distal-most apices the at least some of the cell structures in the distal section of the elongate cylindrical main body portion comprise a first strut that extends between the proximal-most and distal-most apices to form a bottom side of the cell structure and a second strut circumferentially spaced-apart from the first strut that extends between the proximal-most and distal-most apices to form a top side of the cell structure, the width of the intermediate strut being less than the width of each of the first and second struts.

9. The embolic obstruction retrieval device of claim 8, wherein in the expanded configuration, the average diameter of the distal section of the elongate cylindrical main body portion is greater than the average diameter of the proximal section of the elongate cylindrical main body portion.

10. The embolic obstruction retrieval device of claim 8, wherein the cell structures in the proximal end portion and the elongate cylindrical main body portion comprise strut elements, at least some of the struts of the cell structures in the distal section of the elongate cylindrical main body portion having a radiopaque wire or ribbon wound thereabout.

11. The embolic obstruction retrieval device of claim 8, wherein the elongate cylindrical main body portion comprises a first circumferential row of cell structures and a second distal-most circumferential row of cell structures, each of the second distal-most circumferential row of cell structures comprising a proximal side, a distal side, a top side and a bottom side, the proximal side being coupled with an adjoining cell structure in the first circumferential row of cell structures and the distal, top and bottom sides being unattached to any adjoining cell structure.

12. The embolic obstruction retrieval device of claim 8, wherein the overall length of the intermediate strut is approximately equal to the overall length of at least one of the top and bottom sides.

13. The embolic obstruction retrieval device of claim 8, wherein the elongate cylindrical main body portion has a distal-most circumferential row of cell structures and comprises a plurality of circumferentially spaced-apart antennas extending distally therefrom and being joined together to form a partially closed end at or near the distal end of the elongate cylindrical main body portion.

14. The embolic obstruction retrieval device of claim 8, further comprising a first proximally extending elongate flexible wire connected to the proximal antenna.

15. An embolic obstruction retrieval device comprising; an elongate self-expandable member having a radially expanded configuration and a radially unexpanded configuration, the self-expandable member comprising a plurality of generally longitudinal undulating elements with adjacent undulating elements being interconnected in a manner to form a plurality of diagonally disposed cell structures, the self-expandable member having a proximal end portion and an elongate cylindrical main body portion, the cell structures in the elongate cylindrical main body portion extending circumferentially around a longitudinal axis of the self-expandable member, the cell structures in the proximal end portion extending less than circumferentially around the longitudinal axis of the self-expandable member, the cell structures in the elongate cylindrical main body portion comprising proximal and distal facing V-like structures that are interconnected by a pair of diagonally extending and circumferentially spaced-apart struts, the proximal and distal V-like structures having a first average width dimension and the pair of diagonally extending and circumferentially spaced-apart struts having a second average width dimension that is greater than the first average width dimension, the retrieval device having a proximal antenna extending proximally from a proximal-most end of the proximal end portion of the self-expandable member, wherein the second average width dimension is in the range of 1.2 to 1.5 times greater than the first average width dimension.

16. The embolic obstruction retrieval device of claim 15, wherein the diagonally extending and circumferentially spaced-apart struts are substantially straight.

17. The embolic obstruction retrieval device of claim 15, wherein the diagonally extending and circumferentially spaced-apart struts are curvilinear.

18. An embolic obstruction retrieval device comprising; an elongate self-expandable member having a radially expanded configuration and a radially unexpanded configuration, the self-expandable member comprising a plurality of generally longitudinal undulating elements with adjacent undulating elements being interconnected in a manner to form a plurality of diagonally disposed cell structures, the self-expandable member having a proximal end portion and an elongate cylindrical main body portion comprising a proximal section and a distal section, the cell structures in the elongate cylindrical main body portion extending circumferentially around a longitudinal axis of the self-expandable member, the cell structures in the proximal end portion extending less than circumferentially around the longitudinal axis of the self-expandable member, the cell structures in the elongate cylindrical main body portion comprising proximal and distal facing V-like structures that are interconnected by a pair of diagonally extending and circumferentially spaced-apart struts, the diagonally extending and circumferentially spaced-apart struts comprising first end segments, second end segments, and a middle segment disposed between the first and second end segments, the first end segments being coupled to the proximal V-like structure and the second end segments being coupled to the distal V-like structure, the proximal and distal V-like structures having a first average width dimension, the middle segments of the diagonally extending and circumferentially spaced-apart struts having a second average width dimension that is greater than the first average width dimension, the first and second end segments of the diagonally extending and circumferentially spaced-apart struts having a third average width dimension that is greater than the first average width dimension and less than the second average width dimension, the retrieval device having a proximal antenna extending proximally from a proximal-most end of the proximal end portion of the self-expandable member.

19. The embolic obstruction retrieval device of claim 18, wherein the first and second end segments of the diagonally extending and circumferentially spaced-apart struts comprise tapers.

20. The embolic obstruction retrieval device of claim 18, wherein the diagonally extending and circumferentially spaced-apart struts are substantially straight.

21. The embolic obstruction retrieval device of claim 18, wherein the diagonally extending and circumferentially spaced-apart struts are curvilinear.

22. The embolic obstruction retrieval device of claim 18, wherein the second average width dimension is in the range of 1.1 to 2.0 times greater than the first average width dimension.

23. The embolic obstruction retrieval device of claim 18, wherein the second average width dimension is in the range of 1.2 to 1.5 times greater than the first average width dimension.

* * * * *